United States Patent [19]

Stover et al.

[11] Patent Number: 5,679,515
[45] Date of Patent: Oct. 21, 1997

[54] MYCOBACTERIAL REPORTER STRAINS AND USES THEREOF

[75] Inventors: Charles Kendall Stover, Mercer Island; Mark Jeffrey Hickey, Seattle, both of Wash.

[73] Assignee: PathoGenesis Corporation, Seattle, Wash.

[21] Appl. No.: 316,950

[22] Filed: Oct. 3, 1994

[51] Int. Cl.$^6$ .............................. C12Q 1/68; C12Q 1/66; C12Q 1/18; C12N 1/20
[52] U.S. Cl. .................. 435/6; 435/6; 435/8; 435/32; 435/252.3; 435/253.1; 435/320.1
[58] Field of Search .................... 435/8, 253.1, 320.1, 435/6, 32, 252.3

[56] References Cited

U.S. PATENT DOCUMENTS 5,283,179  2/1994  Wood .......................................... 435/8
5,476,768  12/1995  Pearson et al. ............................. 435/6

FOREIGN PATENT DOCUMENTS

WO 92/01783  2/1992  WIPO .
9316172  8/1992  WIPO .
WO 93/16172  8/1993  WIPO .
WO 93/19603  10/1993  WIPO .

OTHER PUBLICATIONS

Letters in Applied Microbiology, No. 19, No. 5, issued Nov. 1994, Gordon et al., "The application of luciferase as a reporter of environmental regulation of gene expression in mycobacteria", pp. 336–340, see p. 337.
Antimicrobial Agents and Chemotherapy, vol. 39, No. 3, issued Mar. 1995, Cooksey et al., "Bioluminescence Method to Evaluate Antimicrobial Agents against *Mycobacterium avium*", pp. 754–756, see p. 754.
Molecular Microbiology, vol. 15, No. 6, issued Feb. 1995, "L5 luciferase reporter mycobacteriophages: a sensitive tool for the detection and assay of live mycobacteria", pp. 1055–1067, see pp. 1056–1062.
Andrew, P.W. et al. "Construction of a Bioluminescent Mycobacterium and Its Use for Assay of Antimycobacterial Agents", *Journal of Clinical Microbiology* 31:2251 (1993).
Brasier, A.R. et al., "Optimized Use of the Firefly Luciferase Assay as a Reporter Gene in Mammalian Cell Lines.", *BioTechniques* Nov.–Dec.; 7(10):1116 (1989).
Cooksey, R.C., et al., "A Rapid Method for Screening Antimicrobial Agents for Activities against a Strain of *Mycobacterium tuberculosis* Expressing Firefly Luciferase." *Antimicrobial Agents and Chemotherapy* 37:1348 (1993).
DiLella, A.G. et al., "Utility of firefly luciferase as a reporter gene for promoter activity in transgenic mice." *Nucleic Acids Res.* May 11;16(9):4159 (1988).
Engebrecht, J. et al., "Measuring Gene Expression with Light." *Science* Mar 15;227(4692):1345 (1985).

Hanberger, H. et al., "Post–Antibiotic Effect of Beta–Lactam Antibiotics on Gram–Negative Bacteria in Relation to Morphology, Initial Killing and MIC." *Eur. J. Clin. Microbiol. Infect. Dis.* Nov;10(11):927 (1991).
Isaksson, B. et al., "Postantibiotic effect of aminoglycosides on staphylococci." *J. Antimicrob. Chemother.* Aug;32(2):215 (1993).
Isaksson, B. et al., "Synergic post–antibiotic effect of amikacin in combination with beta–lactam antibiotics on Gram–negative bacteria." *J. Antimicrob. Chemother.* Jul;28(1):25–34 (1991).
Jacobs, Jr., W.R. et al., "Rapid Assessment of Drug Susceptibilities of *Mycobacterium tuberculosis* by Means of Luciferase Reporter Phages." *Science* 260:819 (1993).
Jassim, S.A.A. et al., "In vivo Bioluminescence: A Cellular Reporter for Research and Industry." *J. Biolumin. Chemilumin.* Apr.–Jun.;5(2):115 (1990).
Kawamura, I. et al., "Enhanced protection of cyclophosphamide–treated mice against infection with *Pseudomonas aeruginosa* after treatment with Z–100, a polysaccharide–rich extract from Mycobacterium tuberculosis Aoyama B.", *Immunopharmacol. Immunotoxicol.* 12(3):331 (1990).
Korpela, M. et al., "Stable–light–emitting *Escherichia coli* as a Biosensor." *J. Biolumin. Chemilumin* July;4(1):551 (1989).
Limb, D.I. et al., "Comparison of techniques for antimicrobial susceptibility testing of mycobacteria." *J. Clin. Pathol.* May;46(5):403 (1993).
Schmetterer, G. et al., "Expression of Luciferases from *Vibrio harveyi* and *Vibrio fischeri* in Filamentous Cyanobacteria." *J. Bacteriol.* July;167(1):411 (1986).
Stewart, *Lett. Appl. Microbiol.* 10:1 (1990).
Stover et al., *Nature*, 351:456 (1991).
Stover et al., "Development of BCG Vaccines as a Live Recombinant Vaccine Vehicle." In *Vaccines 91*. Cold Spring Harbor Laboratory Press, Cold Spring Harbor, N.Y. (1991).
Wood, K.V. et al., "Introduction to Beetle Luciferases and their Applications." *J. Biolumn Chemilumin* July;4(1):289 (1989).
Jacobs et al., Science, vol. 260: 819–822, 1993.
DiLella et al., Nucleic Acids Research, vol. 16, No. 9: 4159, 1988.

*Primary Examiner*—Douglas W. Robinson
*Assistant Examiner*—Thanda Wai
*Attorney, Agent, or Firm*—Townsend and Townsend and Crew

[57] ABSTRACT

This invention relates to a method of quantifying bacteria in vivo or in vitro using bacterial reporter strains. In particular this invention provides a method utilizing mycobacterial reporter strains that permits rapid screening for in vivo antimycobacterial activity of various compositions. In addition this invention provides for particular mycobacterial reporter strains expressing the FFlux gene at levels sufficiently high to allow detection in tissue homogenates without lysis or concentration of the bacteria.

38 Claims, 3 Drawing Sheets

MYCOBACTERIAL REPORTER STRAINS AND USES THEREOF

FIELD OF THE INVENTION

This invention relates to a method of quantifying bacteria in vivo or in vitro using bacterial reporter strains. The in vivo use of the method is particularly well suited for screening compounds for anti-bacterial activity. In particular, this invention provides for mycobacteria reporter strains comprising a vector that results in a high level of expression of the reporter gene thereby facilitating the use of a simplified assay for quantification of mycobacteria in tissues produced by in vivo infection.

BACKGROUND OF THE INVENTION

*Mycobacterium tuberculosis* (MTB) infects over ten million people each year and kills over three million, making it the infectious agent causing the greatest mortality worldwide. Most of the current drugs used for therapy or prevention of mycobacterial infections are very old and newer treatments (e.g., quinolones and macrolides) have only emerged as adjuncts to developments for other applications. It is clear that current options for the chemotherapy of mycobacterial infections are inadequate and new more effective drugs are desperately needed. The need is made even more urgent by the surge in MTB associated with AIDS and the increased prevalence of MTB strains resistant to front line antimycobacterial drugs such as rifampin and isoniazid, and multiple drug resistant strains of MTB (MDR-MTB).

Efforts to develop new drugs for the treatment of *Mycobacterium tuberculosis* (MTB) infections are seriously impeded by the inherent difficulties associated with laboratory study of MTB. With an extremely slow doubling time of 18 to 24 hours and the necessity to work under stringent biosafety level 3 (BSL-3) conditions, almost all facets of MTB research and treatment are slowed. In particular, the identification of particular (e.g., drug resistant) strains in clinical samples and the screening of potential anti-mycobacterial compounds are expensive and time-consuming processes.

Currently, drug susceptibility of MTB is measured in in vitro culture-based assays. These assays typically determine compound activity on MTB by measuring bacterial growth on agar plates or in broth. These approaches are time consuming and adapt poorly to high throughput screening. Somewhat quicker in vitro assays for testing drug susceptibilities in the clinical setting (e.g. BACTEC) have recently been developed. These assays, however, still take 5 to 10 days, require radioactivity, are expensive, and thus are neither amenable to high throughput screening of compound libraries, nor convenient for identification of lead compounds from complex natural product mixtures.

Studies on MTB are also complicated by the fact that it is an intracellular pathogen. Potential antibiotics or lead compounds with activity against in vitro-grown MTB will not affect intracellular mycobacteria if the compound can't enter or is neutralized by the host cell. Thus, studies on in vitro-grown MTB are misleading as it is likely that the biochemistry, physiology and drug, susceptibilities of the tubercle bacilli will change substantially in bacterial culture, cell culture and in vivo. Accordingly, some potential anti-mycobacterial agents may only act on intracellular bacilli as these compounds may target mechanisms that are necessary for in vivo intracellular growth and survival but not essential for survival in culture. Such compounds would escape detection with current in vitro, culture-based assays.

To address this problem, potential drugs are often assayed on cell cultures (e.g. mycobacterium infected macrophage). However, like other available methods, assaying infected macrophages is time consuming and inconvenient for routine large scale compound screening as it requires lysing the infected macrophage following drug treatment and subsequent determination of MTB colony forming units. For all the reasons discussed above, a strategy for rapidly measuring mycobacterial viability, in vitro (e.g., in bacterial culture or in cell culture) and in vivo would be of great use and would likely have a significant impact on the development of new antimycobacterial drugs.

Strategies employing reporter gene assays hold particular promise as alternatives to drug susceptibility assays that measure growth by turbidity, colony formation, or nutrient utilization (Cooksey et al. *Antimicrob Agents Chemother.*, 37: 1348–1352 (1993); Andrew et al., *J. Clin. Microbiol.*, 31:2251–2254 (1993); Jacobs et al., *Science*, 260:819–822 (1993). Due to its rapidity and sensitivity, reporter gene technology holds great promise to supplement and perhaps supplant the traditional, cumbersome MTB drug sensitivity assays. Assays based on the FFLUX gene encoding firefly luciferase are particularly sensitive and FFLUX has been used as a reporter gene in mycobacteria (Cooksey et al. (1993) supra., Jacobs et al. (1993), supra.).

Recently, an elegant strategy to employ mycobacterial phage in delivery of the luciferase reporter gene was developed for potential use as a more rapid and sensitive diagnostic test of MTB infection and for drug susceptibility testing of MTB clinical isolates (Jacobs et al. (1993), supra.). While the reporter phage strategy is promising for these clinical applications, it is not optimal for assays in which large chemical libraries must be screened. The introduction of reporter phage into screening assays adds an extra level of unnecessary complexity, and the phage itself, even if it is lysogenic, exerts its own effects on the MTB host cell that could potentially confound results. Furthermore, reporter phage may not be useful in assays employing MTB-infected macrophage as the phage may not reliably infect intracellular MTB.

A preferred strategy for compound screening would utilize recombinant mycobacterial reference strains that contain stable expression vectors for the expression of easily assayed reporter gene products. While an in vitro drug susceptibility assay utilizing cultured recombinant mycobacteria expressing FFlux from a plasmid expression vector has been described (Cooksey et al. (1993) supra.), the constructs utilized did not optimize expression of FFlux. The mycobacteria therefore had to be lysed, a time consuming and tedious step, in order to assay the reporter gene product. In addition, this reference only provided for an in vitro (bacterial culture) assay for screening antimycobacterial agents.

In vitro assays do not permit the evaluation of antimycobacterial vaccines or other prophylactic compounds as assays for prophylaxis can only be done in vivo. In addition, as explained above, in vitro assays are not optimally suited for the screening of antimycobacterial agents as they provide no means for evaluating the ability of potential therapeutic compounds to reach a target cell without being degraded, cleared from the blood, eliciting an antigenic response or otherwise adversely effecting the host.

Current in vivo evaluation of therapeutic potential requires long-term MTB infections and periodic laborious plating of organ homogenates at various dilutions to determine colony forming units (CFUs) per organ. These assays typically take at least 3 to 4 weeks. Clearly, an assay that permits rapid in vivo screening of potential therapeutic or prophylactic compositions is greatly desired. Such an assay would ideally be inexpensive, simple, and easily applied to the high throughput screening of compounds. The present invention provides these and other benefits.

SUMMARY OF THE INVENTION

The present invention provides a method of quantifying mycobacteria in vivo. The method generally comprises the steps of infecting an animal with a mycobacterium transfected with a vector, where the vector includes an FFlux reporter gene operably linked to a promoter such that the reporter gene is expressed at a level sufficient to allow detection of the reporter gene in tissue homogenates without lysis or concentration of the mycobacteria, and then detecting the amount of the reporter gene in a tissue of the animal where the amount of the reporter gene indicates the amount of mycobacteria present.

In one embodiment the method further comprises the step of administering an antimycobacterial composition to the animal after infecting it with the bacterium and before detecting the reporter gene. This method permits a determination of the in vivo efficacy of the anti-mycobacterial composition.

In another embodiment the method further comprises the step of administering a prophylactic composition to the animal before infecting it with the mycobacteria thereby determining the efficacy of the prophylactic composition against the mycobacteria.

In any of these methods, the vector may comprise a promoter selected from the group consisting of BCG:hsp60 and BCG:hsp70-tac. A particularly preferred vector for the practice of these methods is pMH30-lux. The most preferred vectors express the FFlux reporter gene at levels at least 3 times greater, more preferably at least 4 times greater, and most preferably at least 5 times greater than BCG:pMV261-lux. The level of expression of the reporter gene is preferably measured by the level of luminescence produced by the bacteria in the presence of luciferin. Thus, the preferred vectors of produce a luminescence level at least three times greater, more preferably four times greater and most preferably five times greater than a luminescence level produced by a BCG:pMV261-lux reporter strain, when the luminescence level is measured by contacting the mycobacteria and the BCG:pMV261-lux reporter strain with luciferin and detecting the resulting luminescence in a luminometer where the contacting and the detecting are under identical conditions for the mycobacteria and the BCG:pMV261-lux. When bacterial cultures of the preferred reporter strains are assayed in the EG&G Berthold model LB96P luminometer according to the preferred method as described herein they express the reporter gene at levels of at least 1.2 RLU/bacterium (cfu), more preferably at least 1.6 RLU/bacterium, and most preferably at least 2.0 RLU/bacterium.

One particularly preferred FFlux is an FFlux in which an ATA codon is replaced with an ATC codon.

The animal utilized in the methods described above may also be an immunocompromised animal.

The high levels of expression of the reporter genes permit rapid evaluation of the in vivo efficacy of therapeutic or prophylactic compositions. In a preferred embodiment, detection of differences in therapeutic efficacy may be detected within 1 to 14 days, more preferably 1 to 7 days, and most preferably within 1 to 3 days of administration of a therapeutic composition. Similarly, detection of differences in prophylactic efficacy may be detected within 1 to 14 days, more preferably 1 to 7 days, and most preferably within 1 to 3 days of administration of the mycobacteria transfected with the vector comprising the FFlux reporter gene.

In a preferred embodiment, the detecting step of the methods described above comprises removing a tissue from the animal; homogenizing the tissue to produce a homogenate; adding a solution comprising luciferin to the homogenate to produce luminescence; and detecting the luminescence. In a particularly preferred embodiment the homogenization is in a solution comprising a buffer and a non-ionic detergent.

Mycobacteria transfected with the vector comprising an FFlux reporter include *Mycobacterium tuberculosis, Mycobacterium intracellulare, Mycobacterium avium, Mycobacterium kansasii, Mycobacterium scrofulaceum, Mycobacterium bovis bacille* Calmette-Guérin (BCG) and *Mycobacterium leprae*. Most preferred are *Mycobacterium avium, Mycobacterium tuberculosis* and *Mycobacterium bovis bacille* Calmette-Guérin (BCG). Thus, particularly preferred mycobacteria reporter strains include MTB:pMH30-lux, BCG:pMH30-lux, and MAC:pMH30-lux.

In one particularly preferred embodiment, the mycobacteria are *Mycobacterium bovis bacille* Calmette-Guérin (BCG); the vector is pMH30-lux; the reporter gene is FFlux in which an ATA codon is replaced with an ATC codon; and the detecting comprises detecting the protein encoded by the mycobacteria in the presence of luciferin.

The present invention also provides means of quantifying mycobacteria in vitro. In one embodiment the method involves the detection of mycobacteria in cells, most typically in cell culture, while in another embodiment this method involves the detection of mycobacteria in bacterial culture. These methods involve providing, in vitro, a cell or a mycobacterial culture containing one or more mycobacteria wherein the mycobacteria are transfected with a vector comprising an FFlux reporter gene operably linked to a promoter selected from the group consisting of BCG:hsp60 and BCG:hsp70-tac; and detecting the amount of the reporter gene in the cell or the bacterial culture where the amount of the reporter gene indicates the amount of intracellular mycobacteria or mycobacteria in culture, and the detection is accomplished without lysis of the mycobacteria.

These methods may further comprise the step of administering an antimycobacterial composition to either the cell or the bacterial culture before detecting the reporter gene, the method thereby determining the efficacy of the antimycobacterial composition against said mycobacteria.

When the method utilizes a cell, the detecting step may comprise lysing the cell in a solution comprising a buffer and a detergent to produce a lysate; adding a solution comprising luciferin to the lysate to produce luminescence; and detecting the luminescence.

When the method utilizes a bacterial culture, the detecting step may comprise adding an aliquot of the bacterial culture to a solution comprising a buffer to produce a bacterial sample; adding a solution comprising luciferin to the bacterial sample to produce luminescence; and detecting the luminescence.

In either of these methods, the vector may be pMV261-lux, pMH30-lux or pMV361-lux. The reporter gene may be an FFlux in which an ATA codon is replaced with an ATC codon. The mycobacteria may be *Mycobacterium tuberculosis, Mycobacterium intracellulare, Mycobacterium* avium, *Mycobacterium kansasii, Mycobacterium scrofulaceum, Mycobacterium bovis bacille* Calmette-Guérin (BCG) or *Mycobacterium leprae*. Particularly preferred mycobacteria include MTB:pMV261-lux, MTB:pMH30-lux, MTB:pMV361-luxBCG:pMV261-lux, BCG:pMH30-lux or BCG:pMV361-lux. In a preferred embodiment, detection of differences in therapeutic efficacy may be detected within 1 to 14 days, more preferably 1 to 7 days, and most preferably within 1 to 3 days of administration of a therapeutic composition.

This invention also provides for vectors expressing an FFlux reporter gene at a level sufficient to allow detection of the reporter gene without lysis or concentration of the mycobacterium and for mycobacterial reporter strains transfected with these vectors. The vectors and therefore the reporter strains may include an FFlux in which an ATA codon is replaced with an ATC codon. The FFlux may be operably linked to a BCG:hsp70-tac promoter or to a BCG:hsp60 promoter.

The vectors may be the pMV261-lux, pMH30-lux, and pMV361-lux vectors and the reporter strains may include these vectors. In a preferred embodiment, the vectors, and therefore the reporter strains express the FFlux reporter gene at a level sufficient to allow detection of the reporter gene in organ homogenates without lysis or concentration of the mycobacteria. A particularly preferred reporter strain comprises the vector pMH30-lux. The most preferred reporter strains include vectors that express the FFlux reporter gene at levels at least 3 times greater more preferably at least 4 times greater, and most preferably at least 5 times greater than BCG:pMV261-lux when assayed in a luminometer as described above. When in vitro bacterial cultures of the preferred reporter strains are assayed in the EG&G Berthold model LB96P luminometer according to the preferred method as described herein they express the reporter gene at levels of at least 1.2 RLU/bacterium or cfu, more preferably at least 1.6 RLU/bacterium, and most preferably at least 2.0 RLU/bacterium.

Particularly preferred vectors and reporter strains permit detection of differences in therapeutic efficacy within 1 to 14 days, more preferably 1 to 7 days, and most preferably within 1 to 3 days of administration of a therapeutic composition.

Preferred mycobacteria for use in the reporter strains of this invention include mycobacteria *Mycobacterium tuberculosis, Mycobacterium intracellulare, Mycobacterium avium, Mycobacterium kansasii, Mycobacterium scrofulaceum, Mycobacterium bovis,* bacille Calmette-Guérin (BCG) and *Mycobacterium leprae*, however, most preferred are *Mycobacterium tuberculosis* and *bacille Calmette-Guérin* (BCG).

The reporter strains, vectors, and assays of this invention allow quantification of extremely small numbers of bacteria. Typically, as few as 100 bacteria can be detected in vitro.

DETAILED DESCRIPTION

Definitions

Figure 1A:
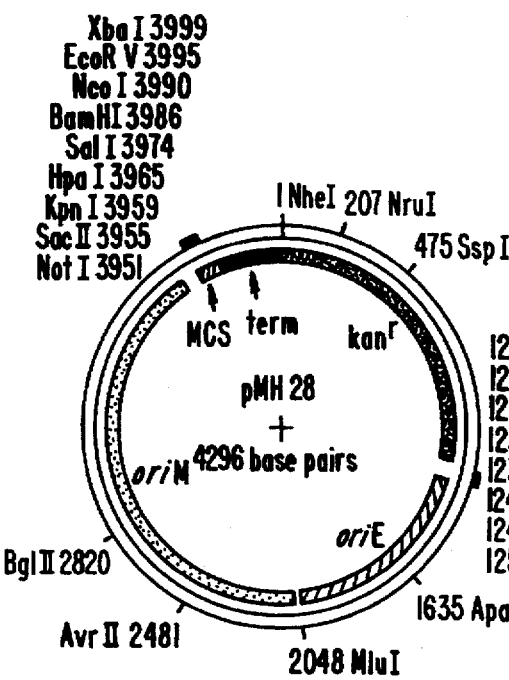
FIG. 1A, FIG. 1B, and FIG. 1C show the pMH28 (Sequence ID No. 15), pMH29 (Sequence ID No. 16) and pMH30lux (Sequence ID No. 12) plasmids used in the preparation of the pMV261-lux (Sequence ID No. 17), the pMH30-lux (Sequence ID No. 12), or the pMV361-lux (Sequence ID No. 18) vectors of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the term "mycobacteria" means any bacteria of the genera Mycobacterium (family Mycobacteriaceae, order Actinomycetales) and includes *Mycobacterium tuberculosis* (MTB), *Mycobacterium avium* complex (MAC), *Mycobacterium kansasii, Mycobacterium scrofulaceum, Mycobacterium bovis* and *Mycobacterium leprae*. Mycobacteria also includes strains of mycobacteria that have been modified chemically, by selective breeding, or by recombinant methods. Thus, for example, mycobacteria also includes attenuated strains such as the *Mycobacterium bovis bacille* Calmette-Guérin (BCG) strains. These species and groups and others are described in Baron, S., ed. *Medical Microbiology*, 3rd Ed. (1991) Churchill Livingstone, New York, which is incorporated herein by reference.

The "biological sample" used in the assays of the invention is any biological tissue, organ or fluid in which bacteria are to be quantified. The biological sample may consist of whole organs or fractions thereof such as spleen, liver, and the like, fluids such as blood or sputum, or other tissues.

The term "quantify", as used herein refers to determination of the number of bacteria in a particular sample. The determination may be an absolute determination or a relative determination as by comparison to a control or reference quantification. Thus, typically, bacterial numbers will be quantified in one treatment relative to a control. It will be appreciated that quantification may also refer to the simple detection of the presence or absence of bacteria.

Colony forming unit (cfu) is a means of quantifying the number of bacteria in a sample. The bacteria are uniformly distributed throughout the sample by means well known to those of skill in the art such as vortexing or sonicating. The suspension is then smeared on culture media, the media are incubated ant the number of resulting colonies are counted. Mycobacteria tend to clump and so great care must be taken to disperse the clumps before screening. This is preferably accomplished by sonication. In mycobacteria, a colony forming unit corresponds to a single bacterium.

The term "in vivo" or "in vivo assay" when used in reference to bacteria or reporter strains herein refers to a measurement or treatment evaluating some aspect of the bacteria or reporter strains in an animal or in a tissue sample that is isolated from an infected animal. It is expected that the levels of bacteria or reporter strains in a tissue isolated from an infected animal are indicative of the level of infection of the animal. One of skill will thus appreciate that in this context, that the bacteria or reporter strains present in the tissue are as a result of the infection and not added to the tissue subsequent to its isolation from the animal. In this context "in vivo" is distinguished from in vitro which is used herein to refer to bacteria either in bacterial culture or in cell culture. In the latter case, the bacteria may be located inside a cell, e.g., a cultured macrophage, but because the cell itself is not within an organism the bacteria is regarded as being in vitro. Thus in vivo drug susceptibility assays refers to assays in which susceptibility of bacteria in an animal to particular therapeutic or prophylactic agents is assayed.

The term "therapeutic agent" as used herein refers to an agent that may be utilized in the treatment of an animal once the animal is already infected with a bacterium. Typical therapeutic agents include, but are not limited to antibiotics such as ethambutol, rifampin, and the like. The term "therapeutic agent" is distinguished from the term "prophylactic agent" which is used herein to refer to a composition that aids in preventing infection of an animal by a bacterium in the first place. Typical prophylactic agents include, but are not limited to vaccines and the like. One of skill will appreciate that a therapeutic agent may possess prophylactic activity and conversely, a prophylactic composition may possess therapeutic activity.

The term "vector" as used herein refers to a nucleic acid sequence comprising a gene under the control of a promoter. The vector typically contains all of the elements necessary for expression of the gene in the host cell. Thus in addition to a promoter the vector typically contains an initiation site and a termination codon. Vectors may also contain elements that aid their replication, manipulation and selection such as origins of replication, multiple cloning sites, selectable markers and the like. The vectors may be circularized and take the form of phagemids, plasmids, cosmids and the like.

The term "operably linked" as used herein refers to linkage of a promoter upstream from a DNA sequence such that the promoter mediates transcription of the DNA sequence.

Nomenclature of the form "rBACT:vector" is used herein to refer to recombinant bacterial reporter strains. In this nomenclature the "r" indicates that the reporter strain in a recombinantly produced reporter strain. The "BACT" identifies the particular bacterial strain, while the "vector" identifies the vector that the strain carries which expresses the particular reporter gene. Thus a recombinant *Mycobacterium tuberculosis* strain carrying the pMH30-lux vector will be designated rMTB:pMH30-lux. Similarly, a recombinant BCG strain carrying the pMV261-lux vector will be designated BCG:pMV261 -lux.

Figure 1B:
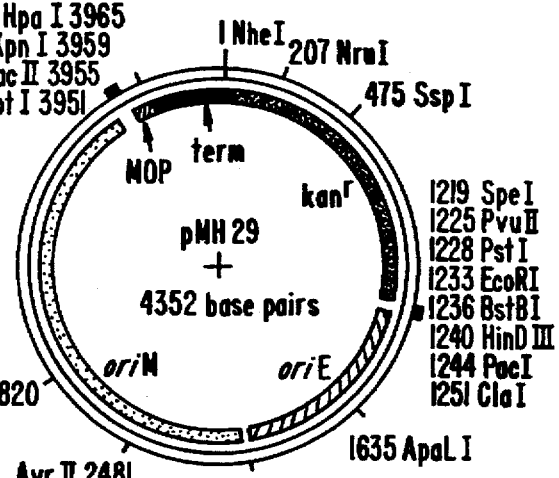
Figure 1C:
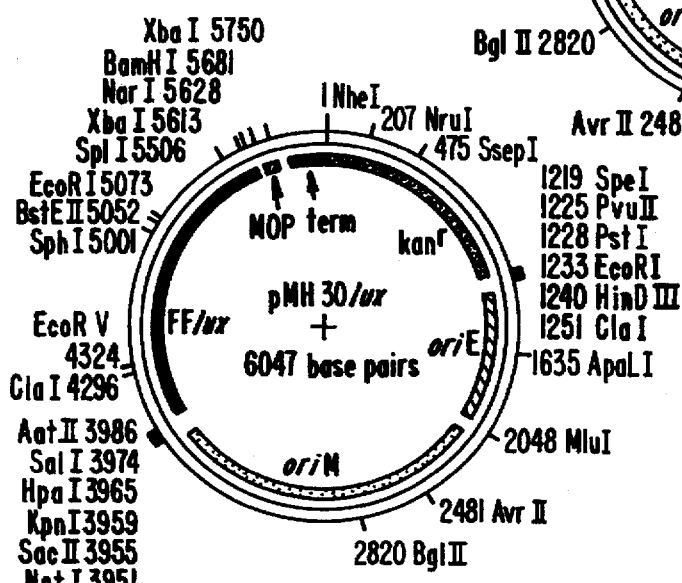

The following nomenclature, which corresponds substantially to current usage, is used herein to designate promoters. The expression "hsp" refers to the heat shock promoter. The term "BCG:hsp60 promoter" refers to the BCG heat shock promoter as found in the pMV261 shuttle vector (see Sequence ID No. 13 and Stover et al. *Nature*, 351:456–460 (1991). Similarly, the term "BCG:hsp70-tac promoter" refers to the synthetic BCG heat shock promoter, comprising an *E. coli* consensus promoter sequence with BCG hsp70 transcriptional and translational sequences, as found in the pMH29 shuttle vector (see Sequence ID No. 16 and FIG. 1). In FIG. 1, the BCG:hsp70-tac promoter is indicated by MOP and is located between the BamHI and the XbaI restriction sites.

The term "FFlux" as used herein refers to the gene that encodes luciferase. More particularly it refers to the firefly luciferase. As used herein the term FFlux may also include modifications of the gene such as nucleotide additions, deletions, and substitutions that still result in the gene encoding a functional luciferase. Thus, for example, specific codon substitutions, such as ATC for ATA may be made to optimize expression in a particular host, but which do not alter the resulting protein. A functional luciferase refers to a luciferase that will produce luminescence in the presence of luciferin and ATP.

The term "recombinant" when used with reference to a bacterium indicates that the bacterium expresses a peptide or protein which is encoded by DNA whose origin is exogenous to the bacterium. Thus, recombinant bacteria express genes that are not found within the native (non-recombinant) form of the bacteria.

The term "immunosuppressed" or "immunocompromised" when used in reference to the test animals described herein refers to animals whose immune system does not function with the same efficacy as it would in a normal, healthy animal. Typically immunosuppressed are characterized by a reduced ability or an inability to mount a humoral or cell mediated immune response against an antigen. Immunosuppression may result as a consequence of infection, treatment with various drugs such as cyclophosphamide, FK506, cyclosporin and the like, or through genetic manipulations, either recombinant or through selective breeding.

Bacterial Reporter Strains.

The present invention provides for a method of quantifying bacteria in vivo and in vitro. This invention is premised on the unexpected discovery that it is possible to produce bacteria carrying recombinantly introduced reporter genes where the reporter gene product is expressed at levels sufficiently high that they are detectable in simple homogenates of infected tissues. Reporter genes are genes that express an easily assayable product. Detection of the assayable product indicates the presence, absence or quantity of the reporter gene which, in turn, indicates the presence, absence, or quantity of the organism bearing the reporter gene. Reporter genes are well known to those of skill in the art. They include, but are not limited to genes expressing bacterial chloramphenicol acetyl transferase (CAT), beta-galactosidase (β-gal), various bacterial luciferase genes encoded by *Vibrio harveyi*, *Vibrio fischeri*, and *Xenorhabdus luminescens*, the firefly luciferase gene FFlux, and the like. However, while many reporter genes are known, the present invention is premised, in part, on the surprising discovery that the FFlux reporter gene may be expressed at unusually high levels in a host pathogen while still maintaining the ability of the host pathogen to infect an animal and propagate in vivo.

Bacteria carrying reporter genes are referred to herein as "reporter strains". Thus a mycobacterium carrying a reporter gene is a "mycobacterial reporter strain", while a pneumococcus carrying a reporter gene is a "pneumococcal reporter strain". As indicated above, reporter strains may be utilized to quantify the number of bacteria carrying the reporter gene in a particular sample. In will be appreciated by one of skill in the art that numerous pathogens are suitable for modification as reporter strains and the selection of a particular pathogen depends on the particular disease state for which therapeutic or prophylactic compositions are being screened. Thus, for example, one may practice the claimed methods with reporter strains of Candida, Streptococcus, Corynebacteria, Helicobacter, Clostridium, Herpes, Hepatitis and the like.

Mycobacteria are particularly preferred pathogens for the production of reporter strains. As explained above, screening of antimycobacterial compositions is problematic because of the slow growth rate of the bacteria, because of the stringent containment requirements necessary for work with pathogenic mycobacteria, and because in vivo mycobacterial drug susceptibility is likely to differ from that indicated by in vitro (e.g. bacterial culture or cell culture) assays. Mycobacteria suitable for the production of reporter strains may be obtained from a number of commercial sources.

A reporter strain that expresses high levels of a reporter gene product that is amenable to detection in a sensitive assay system overcomes these problems. The combination of high expression levels of reporter gene product and a sensitive assay allows the detection of relatively few bacteria. Thus, for example, in the present invention, the unusually high level of expression of FFlux in mycobacteria combined with the sensitive assays available for luminescence (e.g., detection with a luminometer) permits the detection of fewer than 100 mycobacteria in a sample. This high sensitivity makes it possible to detect differences in bacterial number after relatively short culture conditions thereby permitting assays having rapid throughput. In addition, a high sensitivity assay facilitates the use of attenuated (non-pathogenic) bacterial strains such as the attenuated *Mycobacterium bovis bacille* Calmette-Guérin (BCG) strains whose typically slow growth renders them unsuitable for high throughput screening. Finally, a mycobacterial reporter strain that is capable of extended (e.g. over 14 days) growth in vivo and that expresses a reporter gene capable of detection in tissue homogenates provides a system for evaluating the in vivo efficacy of various prophylactic and therapeutic compositions.

While, any mycobacterium may be transfected with the vectors of the present invention to produce mycobacterial reporter strains that express the FFlux gene product (luciferase) at levels sufficient to permit detection in tissue homogenates without lysis or concentration of the mycobacteria, *Mycobacterium tuberculosis* and *Mycobacterium bovis bacille* Calmette-Guérin (BCG) strains are particularly preferred for use as reporter strains. *Mycobacterium tuberculosis* strains are preferred because they are the predominant pathogenic mycobacterium. In addition, it is drug resistant strains *Mycobacterium tuberculosis* that are rapidly appearing and which present the most serious health threat. BCG is a useful reporter strain where there is concern about the safety of the assays. BCG is an attenuated strain of an intracellular mycobacterium that is not pathogenic. Thus the use of BCG avoids the serious containment issues present with *Mycobacterium tuberculosis* while providing a good model for MTB drug susceptibility. The use of BCG in drug susceptibility assays has previously been problematic in that it is a particularly slow growing mycobacterium and its infectivity is low. However the use of the BCG mycobacterial reporter strains of the present invention (e.g. rBCG:pMH30-lux, rBCG:pMV261-lux, and rBCG:pMV361-lux) renders the BCG detectable at extremely low concentrations. This permits data to be taken after much shorter periods of in vitro culture or in vivo infection.

The strategy, of using recombinant bacteria and mycobacteria expressing reporter genes to determine drug susceptibilities in vitro (e.g., in bacterial culture) has been previously described (Cooksey et al. (1993) supra.; Jacobs et al. (1993) supra.). Briefly, a recombinant mycobacterial culture expressing a reporter gene, such, as FFlux is grown to log phase and compounds (drugs) are added at various concentrations to the growing bacteria. Reporter gene assays are performed on aliquots from control (untreated) cultures and drug-treated cultures to assess reporter gene expression. A compound's inhibitory activity is measured by the inhibition of reporter gene expression instead of directly measuring viable bacteria or turbidity.

In contrast to the previous art, however, the present invention is premised on the unexpected discovery that it is possible to provide FFlux-expressing bacterial reporter strains capable of infecting an animal, surviving and propagating in vivo while expressing the FFlux reporter gene product at levels high enough to enable detection in tissue or organ homogenates thereby facilitating the evaluation of in vivo efficacy of therapeutic or prophylactic compositions. In particular, the present invention provides for FFlux-expressing mycobacterial reporter strains capable of infecting an animal and being subsequently detected in tissue homogenates without lysis or concentration of the mycobacterium. This permits assays far simpler than previous mycobacterial reporter gene assays which required lysis of the mycobacterium through methods such as repetitive freeze-thaw cycles, sonication, phage-induced lysis, and so forth (see, for example, Cooksey et al. 1993 supra.).

Drug susceptibility assays utilizing the FFlux-expressing mycobacterial reporter strains of the present invention have been validated against standard drug susceptibility assays (BACTEC) with a number of antimycobacterial drugs exhibiting different modes of activity. The reporter strains generally show susceptibilities comparable to those determined by BACTEC and are well suited to assaying the efficacy of various therapeutic or prophylactic compositions. As will be explained below, the mycobacterial reporter strain assays of this invention provide assays that are much cheaper, faster, less labor intensive, obviate the use of radioactivity, and can be easily used for high throughput screening.

Assay Utilizing Bacterial Reporter Strains

A. In Vivo Assays

One embodiment of the present invention comprises a method of quantifying bacteria in vivo. As defined above, the term in vivo or an in vivo assay refers to the presence of bacteria in an animal or in a tissue removed from an animal infected with the bacteria as opposed to in bacterial culture or in cell culture. A preferred embodiment comprises a method of quantifying mycobacteria in vivo. In a particularly preferred embodiment, this invention provides a method of screening various compositions for therapeutic (e.g., antibiotic) or for prophylactic activity against mycobacteria in vivo.

The use of bacterial reporter strains for in vitro studies has been previously described (see, e.g., Cooksey et al. (1993) supra.). However, the use of bacterial reporter strains for the quantification of levels of a particular pathogen in vivo has not been previously described. Indeed there are a number of reasons whereby one of skill in the art would not expect an in vivo assay utilizing bacterial reporter strains to function. It is expected that when a bacteria or other pathogen is transformed so that it express a protein that is not normally expressed, metabolic resources, which would otherwise be utilized for different functions, are diverted to the production of the recombinant protein. Particularly, when the protein is expressed at high levels, at this diversion of metabolic resources is expected to result in a lowered growth rate or infectivity. In addition, the overexpression of foreign proteins is often lethal to the host cell. Additionally, the intracellular environment is a complex mixture of compounds many of which might be expected to inhibit or even degrade the reporter gene product thereby preventing its detection. Finally one of skill in the art would not expect that a reporter gene would be detectable in a complex mixture such as a tissue homogenate. Thus it was a surprising discovery of the present invention that bacterial reporter strains may be produced which express a reporter gene product at levels sufficient to permit detection in a tissue homogenate without lysis or concentration of the bacteria.

In general, the in vivo assays of the present invention involve infecting an animal with an FFlux-expressing bacterial reporter strain, e.g., a bacterium (preferably a mycobacterium) transfected with a vector that expresses the FFlux reporter gene. A biological sample (e.g., organs, blood, or various fluid or tissue samples) is later isolated from the organism and the reporter gene product is detected in the isolated tissue thereby allowing quantification of the level of infection of the tissue by the pathogen.

Methods of infecting an organism with a particular pathogen are well known to those of skill in the art. The method of infection may reflect the normal mode of infection of the particular pathogen. Thus, for example, where a pathogen is normally internalized in a food source the organism may be infected through an oral route. Similarly, where a pathogen achieves entry into the host through a wound, the pathogen may be applied topically to the skin surface or to a laceration. The mode of administration may also be chosen simply for convenience or to avoid a particular organ system. Methods of administration include, but are not limited to presentation as an aerosol, topical application, anal or oral administration, and injection (e.g., intraperitoneal, intramuscular, subdermal, or intravenous) and the like.

Where it is desired to assay for the in vivo efficacy of a potential therapeutic composition, the animal is infected with the reporter strain, and then the potential drug is administered immediately or following an initial adaptation period. Then a biological sample, (e.g. organs, various tissue samples or blood) is collected and the reporter gene product in the sample is quantified thereby quantifying the reporter strain. Comparison of the levels of the reporter strain in the tissues of a test animal with levels of the reporter strain in a control animal which received the same treatment without the potential therapeutic composition provides a measure of the efficacy of the therapeutic composition. More effective compositions will result in a lower reporter strain infection than less effective compositions. One of skill will appreciate that samples may be obtained at a fixed time point after administration of the therapeutic agent, or alternatively, biological samples may be obtained over a course of time to establish the time course of infection. One of skill will also appreciate that the therapeutic may be administered throughout the assay, administered only for an initial period of the assay, or administered over several separate time intervals.

In another embodiment, this invention provides for a means of assaying for the in vivo efficacy of a prophylactic composition (e.g., a vaccine). In this embodiment, the organism is administered the prophylactic composition one or more times. The animal is then either immediately or after a period of adaptation challenged with the particular reporter strain. After allowing a period of time for an infection to develop, one or more biological samples are obtained and the level of reporter strain in the sampled tissues is quantified by measuring the level of reporter gene product. Again, comparison to control animals that receive the same treatment, but not the prophylactic composition, provides a measure of the efficacy of the prophylactic composition. One of skill will appreciate that the prophylactic composition may also be administered through the period of the assay (i.e., continuing after challenge with the reporter strain). Again, the assay may be designed for sampling at a single time point or multiple sampling over a period of time to establish a time course of infection.

Administration of a therapeutic may result in long term changes that effect the ability of a pathogen to infect an organism (so called post-treatment effects). For example, the temporary administration of antibiotics to an infected organism may facilitate the development of an immune response which may suppress or eliminate the infection and may alter the animal's susceptibility to infection by the same or related pathogens. Antibiotics may have other effects that impact the progress of infection after cessation of the administration of the antibiotic.

Thus this invention also provides methods for assaying that reveal the post treatment effects of various therapeutic agents. In this case, the agent is administered to the animal infected with the reporter strain for a period of time and then stopped. Biological samples are taken over a period of time to monitor infection levels of the reporter strain. The animal may also be subsequently challenged with the same or different reporter strains to evaluate long term changes in susceptibility. By allowing earlier in vivo detection and by maintaining sensitivity to small changes in bacterial concentration, the assays of the present invention, particularly those using the mycobacterial reporter strains of the present invention, permit following the infection over a longer period of time than conventional assays. This facilitates the examination of post-treatment effects.

Most healthy animals mount some immune response in response to challenge by a pathogen. This native immune response may limit the time period over which the above-described assays are useful and reduces the rate or levels of infection of the animal's tissues. The useful period of in vivo infection by the reporter strain may be increased by the use of immunocompromised animals that are unable to mount an effective immune response. In addition such immunocompromised animals, by allowing higher rates of infection by the pathogen, permit the detection of different drug susceptibilities much sooner than in animals that are not immunosuppressed. Thus detection of a response of mycobacterial reporter strains might be as rapid as 1 day or less. In addition, the use of immunocompromised animals allows the detection of drug susceptibilities to progress for longer periods of time after infection by the reporter strain. Thus, for example, in the case of mice infected with the mycobacterial reporter strains of the present invention a healthy mouse shows an immune response in 10 to 14 days with a decrease in infection levels. In contrast mice immunosuppressed with cyclophosphamide show no immune response for periods in excess of 3 weeks. The longer in vivo period makes assays in immunosuppressed animals particularly suitable for investigation of post treatment effects of various therapeutics.

Mice, or other animals, may be immunocompromised by a number of means well known to those of skill in the art. Particularly preferred are animals immunocompromised by the use of drugs, e.g., cyclophosphamide, FK506, cyclosporin and the like, or bred or transgenic animals that have been engineered to possess compromised immune systems, e.g. gamma interferon knockout mice, gamma interferon receptor knockout mice, nude mice, SCID mice and the like.

The in vivo assays for testing prophylactic and antimycobacterial activity of the present invention represent a significant advance over traditional in vivo assays which typically required long term (4–8 week) drug treatments, and plating and culturing of organ homogenate dilutions for an additional 3-week incubation and colony counting. Typically, when the assays are performed in mice utilizing mycobacteria containing the pMV261-lux, the pMH30-lux, or the pMV261 vectors, the assay mice are infected intravenously with a mycobacterial reporter strain and treated with drugs for 7 to 14 days. Organ homogenates are assayed for luminescence at intervals in 7–14 day experiments and are compared with an untreated control groups infected with an identical dose. However it is possible to run shorter experiments as differences between various drugs are observed in 3 to 7 days, frequently 1 to 3 days and occasionally in under 1 day.

The in vivo assays of the present invention may be practiced with almost any vertebrate. Suitable test animals are well known to those of skill in the art. The animals are preferably non-human animals capable of being infected by the particular bacterial reporter strain. These animals include vertebrates such as non-human primates, ovine, canine, bovine, rattus and murine species as well as rabbit and the like. Preferred non-human animals are selected from the rodent family including rat, guinea pig and mouse, most preferably mouse.

The mode of administration of the therapeutic or prophylactic composition to be screened reflects the mode or action or chemical susceptibilities of the composition, the condition it is to be used to treat, the species of test animal, and experimental convenience. The bases of selecting modes of administration of test compositions are well known to those of skill in the art. Suitable modes of administration include, but are not limited to, parenteral administration, such as intravenous administration or administration into a body cavity or lumen of an organ, topical, oral, anal, or local administration, such as by aerosol or transdermally. The composition may also be administered subcutaneously or intramuscularly as by injection.

In Vitro Assays

As used herein, the term in vitro in reference to therapeutic or prophylactic susceptibility assays refers to assays in which the therapeutic or prophylactic composition is applied either to a culture of the pathogen itself, or to a cell culture containing the pathogen. Thus, for example, in vitro drug susceptibility studies of mycobacteria, may be performed by applying the drug to mycobacteria in bacterial culture or to a cell cultures that contains cells (e.g., macrophages) infected with mycobacteria.

A.) Bacterial Culture Assays

The present invention provides for methods of screening for antimycobacterial activity in compositions using an in vitro, bacterial culture assay. In general, these assays comprise culturing the mycobacteria reporter strains, exposing the cultured mycobacteria to a drug, and then subsequently assaying the reporter gene to determine differences in mycobacterial growth between the drug-treated test mycobacteria and untreated control cultures (see, for example, Cooksey et al. (1993) supra.). However, in contrast to previous bacterial culture assays, the present invention provides for mycobacterial culture assays that utilize a mycobacterial reporter strain that expresses the reporter gene at levels sufficient to allow detection of the reporter gene in without lysis or concentration of the mycobacteria. Mycobacteria possess a tough cell wall rendering lysis tedious and time consuming. By allowing elimination of this step the assays of this invention are less labor intensive, less expensive, and easily modified for high throughput screening.

In a preferred embodiment mycobacterial reporter strains comprising the pMV261-lux, pMH30-lux, or pMV361-lux vectors are cultured using techniques well known to those of skill in the art (see, e.g., *The Mycobacteria*: A Source Book, Kubica and Wayne, eds, Marcel Deckker, N.Y. (1984); Good et al. *Clin. Chest Med.* 10:315–322 (1984), *Heifets Ann. Rev. Respir. Dis.*, 137:1217–1222 (1988), and Sommers et al. in *Color Atlas and Textbook of Diagnostic Microbiology, Third Edition*, J. B. Lippincott Co., Philadelphia, Pa. (1988) which are incorporated herein by reference). Any mycobacterium may be utilized, but particularly preferred mycobacterial reporter strains include MTB, BCG and MAC. The "test" cultures are treated (exposed to) with the composition to be screened for antimycobacterial activity for 1 to 14 days. Where rapid screening is desired the drug treatment may run from 1 to 10 days or even more preferably from 1 to 5 days.

Samples of the cultures are taken, and assayed for luminescence as described below. The measure of luminescence is a function of the concentration of the mycobacterial reporter strain which, in turn, reflects the antimycobacterial activity of the test composition. Comparison of the treated cultures with untreated cultures provides a measure of the efficacy of the antimycobacterial composition. therapeutic agent.

B) Cell Culture Assays

The present invention provides for methods of screening for antibacterial activity of compositions using an in vitro, cell culture assay. This assay, while not providing the information available from an in vivo assay, allows evaluation of the efficacy of potential antibacterial compositions against intracellular bacteria. In a preferred embodiment, the assay utilizes a mycobacterial reporter strain. Cultured cells (usually macrophages) are infected with a low multiplicity of infection (e.g., 0.1–1.0 mycobacterium/macrophage) with a mycobacterial reporter strain, preferably recombinant BCG, MTB or MAC reporter strains (more preferably mycobacterial reporter strains comprising strains of BCG, MTB, or MAC transfected with the pMV261-lux, pMH30-lux, or pMV361-lux vector) and treated with drugs for 1 to 14 days. Where rapid screening is desired the drug treatment may run from 1 to 10 days or even more preferably from 1 to 5 days. Luminescence is assayed at intervals and curves may be constructed to determine the kinetics of intracellular antimycobacterial activity. Alternatively, luminescence may be assayed at a single pre-determined endpoint. As with bacterial culture assays reporter gene expression in drug-treated infected cultures is compared with untreated control cultures to determine inhibition of reporter gene expression as a measure of drug activity on cell viability. The use of mycobacterial reporter strains in the infected macrophage assay allows direct measurement of a drug activities on intracellular mycobacteria without lysing infected cells and subsequent agar plating for determination of colony forming units (CFUs).

One of skill in the art will appreciate that assays using cell cultures infected with reporter strains may be performed utilizing any cell type that may be infected by the particular reporter strain utilized. In the case of mycobacterial reporter strains, suitable cell types include any cell that can be infected by mycobacteria, including macrophages and macrophage-type cells. Mycobacterium-infectable cells may be easily identified by exposing the putative mycobacterium-infectable cell to mycobacteria and then later examining the cell microscopically to detect the presence of intracellular mycobacteria. Preferred mycobacterium-infectable cells are "macrophage-type" cells including monocytes, macrophages, human U937 cells and Murine J cells. These and other cell lines that can be infected by mycobacteria are available from private and commercial sources, such as American Type Culture Collection ("Catalogue of Cell Lines and Hybridomas," 6th edition (1988) Rockville, Md., USA); National Institute of General Medical Sciences 1990/1991 Catalog of Cell Lines (NIGMS) Human Genetic Mutant Cell Repository, Camden, N.J.; and ASHI Repository, Bingham and Women's Hospital, 75 Francis Street, Boston, Mass. 02115.

Detection of FFlux Reporter Strains

One of skill in the art will appreciate that the FFlux gene encodes firefly luciferase, an enzyme that reacts with the substrate luciferin and adenosine triphosphate (ATP) to produce luminescence (light). The luminescence may be detected by a variety of means known to those of skill in the art including solid state detectors, video cameras, photomultipliers, photosensitive chemistries and the like. Instruments called luminometers have been designed expressly for detection and quantification of luminescence and are the preferred means of FFlux reporter gene detection.

The in vivo propagation of reporter strains may be detected in biological samples isolated from an animal. The in vitro propagation of reporter strains may be detected in bacterial cultures of the reporter strain or extracts of those cultures, or in cell cultures (i.e., macrophage cultures) comprising cells infected by the reporter strains or in compositions or extracts derived from those cell cultures. The high level of expression of the FFlux reporter gene in the reporter strains of the present invention permits greatly simplified assays (quantification) of reporter gene products from any of these sources.

A) Assaying Reporter Strains in Bacterial Culture

The detection of FFlux reporter strains in bacterial culture has been previously described (see Cooksey et al., (1993) supra.), however it was a surprising discovery of the present invention, that mycobacteria expressing the product of the FFlux gene at high levels may be detected without lysis or concentration of the bacteria.

Thus, this invention provides a method of detecting FFlux-expressing reporter strains (preferably FFlux-expressing mycobacterial reporter strains) where the method simply involves suspending the bacteria in a buffer, adding luciferin and detecting the resulting illumination using a luminometer. Many suitable buffers are known to those of skill in the art. A preferred buffer is 100 mM $Na_3$-citrate at pH 5.1. Typically, the luciferin substrate is made up according to standard methods in the same buffer as the sample. In a preferred embodiment, the luciferin will be made up as a 1 mM solution of the sodium salt of luciferin in a buffer, e.g. in 100 mM $Na_3$-citrate at pH 5.1. Many luminometers include a provision for autoinjecting the sample with luciferin. In this case, the bacterial suspension is simply inserted in the luminometer and read directly.

In a particularly preferred embodiment, the assay involves taking one or more 10 µl sample of the bacterial culture(s) in log phase growth and adding each sample to 90 µl of buffer (preferably 100 mM $Na_3$-citrate at pH 5.1) in a well of an opaque 96 well microtiter plate to produce one or more 100 µl test samples. The samples are preferably analyzed in a 96 well microtiter plate luminometer (e.g., EG&G Berthold model LB96P luminometer). The luminometer injects 100 µl of luciferin made up as a 1 mM solution of the sodium salt of luciferin in 100 mM $Na_3$-citrate at pH 5.1. The luminometer is operated according to standard procedures (e.g. the model LB96P luminometer is run with a 15 second integration period and 0.5 second background sampling) provide a measure of luminescence in relative lux units (RLUs).

The RLU reading is normalized to the number of colony forming units or bacteria resulting in a luminescence expressed as RLU/cfu or RLU/bacterium. Means of determining bacterial count or colony forming units are well known to those of skill in the art. When determining colony forming units with mycobacteria, care must be taken to disperse the bacteria, e.g. through sonication or vigorous vortexing, and eliminate clumping prior to plating for the determination of CFUs.

Mycobacterial reporter strains comprising the pMV261-lux, pMH30-lux, or pMV361-lux vectors are particularly suited to the practice of this method. The BCG, MTB and MAC mycobacterial strains transfected with pMV261-lux, pMH30-lux, or pMV361-lux provide exceptionally good results.

B) Assaying Reporter Strains in Cell Culture

It is also possible to quantify FFlux-expressing reporter strains infecting cells grown in cell (e.g., macrophage) culture. Again, it was a surprising discovery of the present invention that reporter strains expressing FFlux at unusually high levels could be detected without lysis or concentration of the mycobacterium. As with bacterial culture assays, this makes feasible a much simpler assay.

The assay of reporter strains in cell culture is similar to the assay of reporter strains in bacterial culture. In general the assay involves washing the cultured cells with a buffer (e.g. 1X Hanks) or with the tissue culture media. The cells are then lysed in a buffer containing a detergent, preferably a non-ionic detergent such as Triton X-100. Luciferin is added to the lysate resulting in luminescence produced by reaction with the luciferase present in the mycobacteria. The amount of luminescence is assayed by any of a variety of means known to those of skill in the art, most preferably by use of a luminometer.

In a particularly preferred embodiment, mycobacterium infected macrophage cells are rinsed with culture medium. The cells are then lysed using phosphate buffered saline (PBS) pH 7.4 containing 1% Triton X-100. An aliquot of 10 µl of the lysate is added to 90 µl PBS-TX100 in a well of an opaque 96 well microtiter plate. The lysate is assayed in a luminometer as described above for the assay of bacterial cell cultures.

While it is preferred to lyse the host cell itself to facilitate transport of the luciferin to the mycobacteria, often this step is not required and intact cells may be assayed directly.

C) Assaying Reporter Strains in Organ Homogenates

While the means of generally detecting various reporter genes are well known to those of skill in the art, it was a surprising discovery of the present invention, that mycobacteria expressing the product of the FFlux gene at high levels may be detected in simple tissue homogenates. Thus, this invention provides for a novel and simple assay for detecting reporter strains in tissue homogenates which greatly facilitates the in vivo assays.

In general, in vivo detection of reporter strains involves obtaining a biological sample (e.g. a tissue or organ) from an animal infected with the reporter strain. The biological sample contains the mycobacterial reporter strain as a consequence of the infection and quantification of the reporter strain in the sample is a measure of the level of infection of the animal. The sample (tissue) is homogenized by any of a number of means known to those of skill in the art (e.g. a blender, a tissue grinder, etc.). The tissue is preferably homogenized in a buffer, for example phosphate buffered saline pH 7.4. The buffer may additionally contain a non-ionic detergent (e.g., Triton X-100) which may lyse the host cells. The detergent also, decreases the viscosity and prevents congealing of the homogenate.

In a particularly preferred embodiment, the homogenate is adjusted to provide 5% wt/volume of tissue to buffer/detergent which is then diluted to 0.5% (wt/vol) in the assay buffer. The detergent is present at about 1%. Luciferin is added to the sample solution and the resulting luminescence is quantified according to any of a number of methods well known to those of skill in the art, most preferably by the use of a luminometer.

In a preferred embodiment, the homogenate is assayed for luminescence in a 96 well microtiter plate format. For example, for an assay utilizing an EG&G Berthold model LB96P luminometer, a 10 μl aliquot of the homogenate is added to 90 μl of phosphate buffered saline (PBS) 7.4 containing 1% Triton X-100 to make a sample solution of 0.5% wt/volume to tissue to buffer/detergent. The assay is initiated when 100 μl of a 1 mM solution of luciferin (or the sodium salt of luciferin) in a buffer (e.g. 100 mM $Na_3$-citrate at pH 5.1) is added to the sample solution. With the model LB96P, the readings are made with an integration period of 15 seconds, a background measurement time of 0.5 seconds and a background warning level of 500 RLU/sec.

This method of detection is particularly suitable for use with the mycobacterial strains transfected with the pMH30-lux vector of this invention. It was particularly surprising that the mycobacterial reporter strains of the present invention were detectable in homogenates without lysis or concentration of the mycobacteria. The rapidity, ease, and accuracy of this detection method represents a substantial improvement over previous approaches.

D) Identifying Suitable FFlux-Expressing Reporter Strains

As indicated above, FFlux-expressing reporter strains may be assayed in bacterial cultures and cell cultures without lysis or concentration of the bacteria if the FFlux reporter gene is expressed at high levels. Similarly, without being bound to a particular theory, it is believed that it is the high level expression of the FFlux gene in a bacterial reporter strain that renders the in vivo (tissue homogenate) assays feasible. Identification of suitable reporter strains thus requires identifying FFlux-expressing bacterial reporter strains that express the FFlux gene product (luciferase) at a level high enough to permit the described assays. In general, this is accomplished by producing a bacterial culture of the reporter strain and then assaying it as described to determine if it is above a certain minimum expression level as discussed below. Once the expression levels have been demonstrated to be sufficiently high, the reporter strain is administered to an animal to determine if the strain is capable of infecting the animal and propagating in vivo.

Suitable expression levels may be determined by reference to the Connaught strain of BCG transfected by the pMH261-lux vector as described herein. The BCG:pMH261-lux reporter strain may be produced as described herein. Then the reporter strain whose FFlux expression level it is desired to evaluate is assayed in parallel with the BCG:pMH261-lux "reference strain" in whatever assay format is desired. Assays utilizing luminometers to quantify the luminescence produced by the reporter strain in the presence of luciferin are most preferred. In these assays reporter strains suitable for the in vivo assays of the present invention will express FFlux gene product at levels of at least 3.0 times BCG:pMV261-lux, more preferably at least 4.0 times BCG:pMV261-lux, and most preferably at least 5.0 times BCG:pMV261-lux. Thus, for example if BCG:pMH261-lux shows an expression level of 0.4 RLU/bacterium in a particular luminometer assay format, reporter strains suitable for the practice of this invention will show expression levels of at least 1.2 RLU/bacterium, more preferably at least 1.6 RLU/bacterium, and most preferably at least 2.0 RLU/bacterium.

Alternatively, suitable expression levels may be specified in terms of the luminescence per bacterium as determined under specific assay conditions in a specific luminometer. Luminometers generally give luminescence values in "relative light units" (RLUs) which are then normalized to "colony forming units" (CFUs). Since a CFU is equivalent to a single mycobacterium, it is convenient to describe expression levels of mycobacterial reporter strains in terms of RLUs/mycobacterium. RLU's however are not absolute units of measure, and the number of RLUs determined for a particular reporter will vary with the luminometer used for the measurement, the geometry of the assay (e.g. microtiter plate vs test tube, etc.) and the composition of the assay solution (e.g. tissue homogenate or culture broth or buffer, etc.). Expression levels, however may be reliably compared, however, when assayed under the same conditions, by the same model luminometer.

Thus, in a preferred embodiment, the FFlux-expressing reporter strains of the present invention will preferably show an activity of at least 1.2, more preferably at least 1.6, and most preferably at least 2.0 RLU/CFU (=RLU/bacterium) when assayed as follows: An aliquot of bacterial reporter strains growing in Middlebrook 7H9 (or similar) medium at log phase (i.e. at a density of $5\times10^6$ to $1\times10^8$ cells/ml) is taken. To 90 μl of 100 mM $Na_3$-citrate at pH 5.1 are added 10 μl of the 7H9 bacteria-containing broth to produce 100 μL of sample solution which is placed in a well of a 96 well white opaque microtiter plate. The sample is read in a an EG&G Berthold model LB96P luminometer which injects 100 μl of luciferin to provide a total reaction volume of 200 μL. The sample is read for 15 seconds (integration period) with a background measurement time of 0.5 seconds and a background warning level of 500 RLU/sec.

While the above assay is described in terms of a 96 well plate format in an EG&G Berthold model LB96P luminometer the assay may be performed in any of a number of other luminometers. However, since the absolute sensitivity of different brand and model luminometers differ, the RLU/cfu or RLU/bacterium values must be corrected for the difference in sensitivity between the luminometer used for the assay and the LB96P luminometer described above. This is accomplished by multiplying the RLU/cfu value obtained on the test luminometer by the ratio: LB96P sensitivity/test luminometer sensitivity. Thus, for example, if the LB96P luminometer sensitivity is twice that of the test luminometer, the luminometer assay values (RFU/cfu) must be multiplied by 2 when comparing them to the values given above.

The sensitivity of the luminometer is typically provided in the documentation of the machine. Alternatively, the sensitivity may be determined experimentally. This is accomplished using techniques well known to those of skill in the art (see, e.g., Jago et al. *J. Bioluminescence and Chemiluminescence*, 3:131–145 (1989) which is incorporated herein by reference. The instruments may be calibrated in terms of RLUs generated per ATP consumption or in terms of RLUs generated amount of luciferin. Calibration of the instrument in terms of RLUs per ATP merely requires running the assay with an abundance of luciferase and luciferin, adding various ATP concentration standards and measuring the resulting luminescence (RLUs). The sensitivity is then expressed as RLU/ATP. (See Jago et al. supra. for the details of performing the assay.) In general, although evaluations performed with different firefly luciferase preparations will provide different estimates of absolute sensitivity, the relative performance of the various machines will be maintained. Id. Thus conversion factors determined as described will be reliable.

Construction of Reporter Strains

In addition to the various assays described above, this invention provides for reporter strains suitable for the practice of these assays and for vectors suitable for the production of the reporter strains. In particular, this invention provides for reporter strains developed to provide optimal expression of the FFlux gene in mycobacteria and the development of an assay to measure luminescence in crude organ homogenates. These mycobacterial reporter strains contain a vector that express a reporter gene at level sufficient to allow detection of the reporter gene in organ homogenates without lysis or concentration of the bacteria containing the reporter strain.

Generally the design of a vectors that express reporter genes at high levels in a particular host relies on the identification of a promoter, either constitutive or inducible, that characteristically expresses genes under its control at high levels in the particular host. A number of high expression level promoters are known to those of skill in the art. These include, for example the tac promoter, the hsp promoters (e.g., hsp70), the T7 promoter, the alpha antigen promoter and others. In the case of mycobacteria, a mycobacterial heat shock promoter (hsp) is often preferred. Where particularly high levels of expression are desired a multiple copy non-integrating vector is often preferred.

In addition to an strong promoter, often the sequence of the nucleic acid comprising the reporter gene may be altered to optimize expression in a particular host. These alterations may include the modification of certain codons to reflect particular codon usage of the reporter strain. Thus, certain codons are found more frequently in particular species and conversion of a codon encoding a particular amino acid to the particular codon more frequently found in a particular host may increase the level of expression of the particular codon.

In the present invention, three vectors were prepared that show unusually high levels of expression of the FFlux (firefly luciferase) gene in transfected mycobacterial hosts. These vectors, designated pMV261-lux (Sequence ID No. 17), pMH30-lux (Sequence ID No. 12), or pMV361-lux (Sequence ID No. 18) may be constructed from vector pT3/T7-luc (Clonetech, Palo Alto, Calif., USA) by PCR amplification. First an FFlux expression cassette is produced. The cassette consists of a primer-added BamHI site immediately 5' to the second codon (GAA) of FFlux and a primer-added SalI site 3' to the FF-lux stop codon. A PCR primer directed mutation is also made at the sixth isoleucine codon of the native FFlux gene to change the ATA codon which is very rare in mycobacteria and other bacteria, to a more frequent ATC codon. This mutation is made because rare codons at the 5' end of genes can substantially decrease gene expression in mycobacteria and other bacteria. The resulting PCR fragment is digested with BamHI and Sal I to generate cohesive termini contained within the PCR primers used to amplify the FFlux gene and subsequently inserted into BamHI-SalI digested extrachromosomal mycobacteria-*E. coli* shuttle expression vectors pMV261, and pMH29 downstream from the BCG hsp60 promotor and a synthetic BCG:hsp70-tac promotor respectively to generate vectors designated pMV261-lux and pMH30-lux. A NotI-SalI lux expression cassette taken from pMV261-lux is also inserted into the integrative mycobacteria-*E. coli* shuttle vector pMV306 carrying the mycobacterial L5-phage integrase and attP phage attachment sequence to generate pMV361-lux. Following construction of pMV261-lux, pMH30-lux and pMV361-lux *E. coli*, FFlux expression is confirmed by performing luminescence assays on *E. coli* kanamycin resistant transformants. The pMV261-LUX, pMH30-LUX and pMV361-LUX plasmids confirmed to express FFlux luminescence are then transfected into BCG Connaught strain and selected on Middlebrook 7H11 plates containing kanamycin at 15 μg/ml. Kanamycin resistant rBCG transformant colonies are selected and expanded in liquid culture.

Details of the construction described above are provided in Example 1. In addition Sequence Listing Nos. 11, 12, and 13 provide complete nucleotide sequences of plasmids pMV261-lux, pMH30-lux, or pMV361-lux respectively. One of skill in the art will appreciate that the vectors may be produced using the method provided in Example 1. Alternatively, one of skill, utilizing the sequence information provided for the pMV261-lux, pMH30-lux, or pMV361-lux vectors (plasmids), could produce the nucleic acids described by these listings using a number of methods well known to those of skill in the art. These may include variations of the amplification techniques illustrated in Example 1, including, for example, amplification techniques such as ligase chain reaction (LCR) (see Wu and Wallace, Genomics, 4:560 (1989), Landegren, et al., Science, 241: 1077 (1988) and Barringer, et al., Gene, 89:117 (1990)), transcription amplification (see Kwoh, et al., Proc. Natl. Acad. Sci. USA, 86:1173 (1989)), and self-sustained sequence replication (see Guatelli, et al., Proc. Natl. Acad. Sci. USA, 87:1874 (1990)). Using the disclosed sequences, the vectors may also be produced by direct chemical synthesis by methods such as the phosphotriester method of Narang et al. Meth. Enzymol. 68: 90–99 (1979); the phosphodiester method of Brown et al., Meth. Enzymol, 68:109–151 (1979); the diethylphosphoramidite method of Beaucage et al., Tetra. Let., 22: 1859–1862 (1981); and the solid support method of U.S. Pat. No. 4,458,066, all such references in this paragraph incorporated by reference herein.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is practically limited to sequences of about 100 to 150 bases, longer sequences may be obtained by the ligation of shorter sequences.

Once the vectors are produced, they may be used to transfect and transform a host pathogen. As described above, while any pathogenic reporter strain may be created, mycobacterial reporter strains are particularly preferred.

The particular procedure used to introduce the altered genetic material into the host cell for expression of the reporter gene sequences is not particularly critical. Any of the well known procedures for introducing foreign nucleotide sequences into host cells may be used. These include the use of calcium phosphate transfection, electroporation, retroviral mediated transfection, polybrene, protoplast fusion, electroporation, liposomes, microinjection, plasmid vectors, viral vectors and any of the other well known methods for introducing cloned genomic DNA, cDNA, synthetic DNA or other foreign genetic material into a host cell (see Sambrook et at., Molecular Cloning: A Laboratory Manual, Cold Spring Harbor laboratory, (1989)). It is only necessary that the particular genetic engineering procedure utilized be capable of successfully introducing into the host cell the intact vector.

Once transfected, the transformed reporter strains may be selected utilizing a selectable marker present on the vector (e.g. a drug resistance gene such as a Kanamycin resistance gene) and cultured by a variety of means known to those of skill in the art (see, e.g. Good et al. *Clin. Chest Med.* 10:315–322 (1984), Heifets *Ann. Rev. Respir. Dis.,* 137:1217–1222 (1988), and Sommers et al. in *Color Atlas and Textbook of Diagnostic Microbiology, Third Edition,* J. B. Lippincott Co., Philadelphia, Pa. (1988) which are incorporated herein by reference). Thus, for example, the recombinant BCG of the present invention may be cultured in Middlebrook 7H9 broth supplemented with 10% ADC, 0.5% glycerol and 20 µg/ml kanamycin.

Screening Kits

This invention also embraces kits for performing the assays described above or for producing the reporter strains of the present invention. Kits for performing the assays typically include one or more containers containing one or more of the reporter strains of the present invention. In a preferred embodiment, the assay kits comprise containers containing mycobacterial reporter strains comprising the pMV261-lux, pMH30-lux, or pMV361-lux vectors. The reporter strains may be in a form suitable for culture or for direct administration to the test animal or cell culture. In addition the kits may contain other materials suitable for the practice of the assays. Thus they may also contain luciferin, ATP, buffers, detergents such as Triton X-100, media for culture of the reporter strains, and the like. The reporter strain may be provided in a device suitable for application to an animal or to a cell culture. Thus the reporter strains may be contained in a disposable syringe or other application device.

In another embodiment, the kits may provide vectors suitable for the production of reporter strains. In a preferred embodiment, the kits typically include one or more containers containing the pMV261-lux, pMH30-lux, or pMV361-lux vectors. In addition the kits may contain various reagents to facilitate the production of reporter strains. These may include the pathogen to be transformed, culture media, buffers, drugs for selection of transformants, and the like.

Methods for using the assay and reporter strain production kits described above will generally be provided in an instruction manual for use of the kit.

EXAMPLES

The following examples are offered by way of illustration, not by way of limitation.

Example 1

Preparation of Reporter Strains

A) Preparation of Vectors

An FFlux expression cassette was constructed from vector pT3/T7-luc (Clonetech, Palo Alto, Calif., USA) by PCR amplification. The plasmid vector pMV206 (see Sequence ID No. 11 and Stover et al., *Development of Recombinant BCG Vaccines. In Vaccines 91.* Cold Spring Harbor Laboratory Press, Cold Spring Harbor, N.Y. (1991), which is incorporated herein by reference) was digested with restriction enzymes Pvu II and Cla I. The cohesive ends were filled in using DNA polymerase (Klenow fragment) and the vector was recircularized. The resulting DNA was then digested with restriction enzymes Mlu I and Spe I, yielding three fragments. Fragment 1 (Mlu/Spe) contained the oriM and kanR region of the vector and fragment 2 (Mlu/Spe) contained the oriE region. Fragment 3, a 14 bp linker with a NotI site flanked by two MluI sites, was discarded.

Oligonucleotides MCS2 5' and MCS2 3' (Table 1 and Sequence ID Nos. 1 and 2 respectively) annealed to generate multiple cloning site 2 (MCS2) and MCS2 was then ligated in excess into the Spe I site of fragment 2. The resulting product was digested with Spe I to remove adapters in the improper orientation. The fragment 2+MCS2 DNA was religated to fragment 1, giving pPA207SC. This vector had a second multiple cloning site, and the Not I site in the original multiple cloning site was now unique.

The T1T2 terminator sequence was amplified from *E. coli* chromosomal DNA by PCR using primers T1T2 5' Bam and T1T2 3' Xba (See Table 1 and Sequence ID Nos. 3 and 4 respectively). In all cases, the PCR cycling protocol was 60 sec: at 94° C., 60 sec at 55° C., and 60 sec at 72° C. for a total of 30 cycles. The amplification product was subsequently isolated using agarose gel electrophoresis. The product was then digested with restriction enzymes Bam HI and Xba I. Oligonucleotides pPA208.MCS-5' and pPA208.MCS-3' (Table 1 and Sequence ID Nos. 5 and 6 respectively) were annealed to generate a new multiple cloning site with Kpn I and Xba I half-sites at its ends, and joined to the T1T2 PCR product at the Xba I site. Plasmid pPA207SC was digested with restriction enzymes Bcl I and Kpn I giving two fragments. The smaller fragment, containing another multiple cloning site, was discarded, and the T1T2+MCS fragment was ligated in its place, yielding plasmid pMH28 (FIG. 1 and Sequence ID No. 15). This vector was digested with restriction enzymes Bam HI and Xba I, and oligonucleotides MOP 5' Xba and MOP 3' Bam (Table 1 and Sequence ID Nos. 7 and 8 respectively) were annealed and ligated into the sites, generating plasmid pMH29 (FIG. 1 and Sequence ID No. 16). The firefly luciferase open reading frame was amplified by PCR from a purified plasmid DNA template (pT3/T7luc from Clontech, Palo Alto, Calif., USA), with primers lux 5' BamHI and lux 3' Sal I (Table 1, and Sequence ID Nos. 9 and 10 respectively) using the protocol described above. The lux 5' BamHI primer added a ribosome binding site upstream of the initiator methionine (underlined in Table 1, above) and changes the isoleucine codon from ATA which is very rare in mycobacteria to a more frequent ATC codon (bolded in Table 1, above) in order to enhance expression. This mutation was made because it has been observed that rare codons at the 5' end of genes can substantially decrease gene expression in mycobacteria and other bacteria (Makoff et at., *Nucleic Acids Res.,* 17: 10191 (1989)).

The resulting PCR fragment was digested with restriction enzymes BamHI and SaLI, at sites provided by the PCR primers used to amplify the FFlux gene, and subsequently inserted into BamHI-SalI digested extrachromosomal mycobacteria-*E. coli* shuttle expression vectors pMV261 (see Sequence ID No. 13, and Stover et al. *Nature,* 351:456–460 (1991), which is incorporated herein by reference), and pMH29 (FIG. 1 and Sequence ID No. 16) down stream from the BCG hsp60 promotor and a synthetic BCG:hsp70-tac promotor respectively to generate vectors designated pMV261-LUX and pMH30-lux.

A NotI-Sal I lux expression cassette taken from pMV261-LUX was also inserted into the integrative mycobacteria-*E. coli* shuttle vector pMV306 (see Sequence ID No. 14 and Stover et al., *Development of Recombinant BCG Vaccines. In Vaccines 91.* Cold Spring Harbor Laboratory Press, Cold Spring Harbor, N.Y. (1991) which is incorporated herein by reference) carrying the mycobacterial L5-phage integrase and attP phage attachment sequence to generate pMV361-LUX.

Following construction of pMV261-LUX, pMH30-LUX and pMV361-LUX *E. coli,* FFLUX expression was confirmed by performing luminescence assays on *E. coli* kanamycin resistant transformants. The assays were performed using a 10 µl sample from the bacterial culture in 90 µl of 100 mM Na₃-citrate buffer, pH 5.1. The luminometer injected into this sample 100 µl of luciferin made up as a 1 mM solution in the same Na₃-citrate buffer. The pMV261-LUX, pMH30-LUX and pMV361-LUX plasmids confirmed to express FFlux luminescence were transfected by electroporation into the BCG Connaught strain and selected on Middlebrook 7H11 plates containing kanamycin at 15 µg/ml. Kanamycin resistant recombinant BCG (rBCG) transformant colonies were selected and expanded in liquid culture in Middlebrook 7H9 medium supplemented with 10% (v/v) ADC enrichment and 0.5% (v/v) glycerol, and culture aliquots were subsequently assayed for luminescence to confirm expression of FFLUX in rBCG transformants.

Plasmid pMV261 is an extrachromosomal multi-copy vector which has been successfully used to express foreign antigens in recombinant BCG vaccines, in some cases to levels exceeding 10% total cellular proteins. While it is reasonable to predict that high level reporter gene expression will be necessary to detect reporter gene product enzymatic activity directly in organ homogenates it is also reasonable to consider that high level expression of FFlux or any foreign gene may not be well tolerated by the host mycobacteria, resulting in attenuated growth or an inability to obtain recombinant clones. In fact data indicates that pMV261-FFlux constructs in BCG and MTB are somewhat attenuated in their ability to grow in vitro.

Compared to control extrachromosomal plasmids not expressing FFlux, very few FFlux expression vector transformants were obtained with pMV261-LUX and pMH30-LUX (2 and 1 respectively) after a 4 week plate incubation suggesting that expression of FFlux from these strong promotors on multicopy vectors is not well tolerated by BCG. Transformation of the single copy integrative vector pMV361-FFlux was much less problematic and numerous transformants were obtained. Recombinant BCG transformants containing extrachromosomal plasmids pMH30-lux and pMV261-lux also grew significantly more slowly in liquid culture than rBCG transformants containing the single copy pMV361-LUX vector, nevertheless luciferase assays on all liquid culture-grown isolates revealed that the rBCG:pMH30-lux transformant consistently expressed luminescence 3-fold greater than the two rBCG:pMV261-lux transformants and 10-fold greater than rBCG:pMV361-lux.

Because the extrachromosomal pMH30-lux and pMV261-lux vectors replicate autonomously and grew significantly slower than transformants containing the stably integrated pMV361-lux vectors the stability of the vectors and expression of luminescence was in the absence of kanamycin was investigated. Despite the significantly slower growth of the pMH30-lux and pMV261-lux transformants in comparison to the integrated pMV361-lux recombinant, growth rates, as measured by optical density and colony forming units were comparable for each rBCG construct with and without kanamycin and plating on media with and without kanamycin yielded identical colony forming units even after 20 generations of growth without kanamycin.

TABLE 1

Oligonucleotides used in the preparation of pMV261-lux, pMH30-lux, or pMV361-lux.

| Name | Sequence | Seq. ID. No. |
| --- | --- | --- |
| MCS2 5' | 5'-CTAG TCAGCTGCAGAATTCGAAGCTTAATTAATCGAT-3' | 1 |
| MCS2 3' | 5'-CTAG ATCGATTAATTAAGCTTCGAATTCTGCAGCTGA-3' | 2 |
| T1T2 5' Bam | 5'-ca GGATCC GATGGTAGTGTGGGGTCTCCCCATG 3'<br>Bam HI | 3 |
| T1T2 3' Xba | 5'-gc TCTAGA TATGACGACAGGAAGAGTTTGTAG 3'<br>Xba I | 4 |
| pPA208.MCS-5' | 5'-CTAGATATCCATGGATCCAGCGATGTCGACGTAGTTAACGGTAC-3' | 5 |
| pPA208.MCS-3' | 5'-CGTTAACTACGTCGACATCGCTGGATCCATGGATAT 3' | 6 |
| MOP 5' Xba | 5'-CTAGACCAGGCTTGACACTTTATGCTTCCGGCTCGTATAATGTGTG<br>GAATTGTGAGCGCTCACAATTCG 3' | 7 |
| MOP 3' Bam | 5'-GATCCGAATTGTGAGCGCTCACAATTCCACACATTATACGAGCCGG<br>AAGCATAAAGTGTCAAGCCTGG T 3' | 8 |
| lux 5' BamHI | 5' - gc GGATCC AGGAGGA ATCACTCA ATG GAA GAC GCC<br>AAA AAC ATC AAG AAA GGC CCG G | 9 |
| lux 3' Sal I | 5'-gcat GTCGAC GTCATCGCTGAATACAGTTAC 3' | 10 |

Example 2

Comparison of Mycobacterial Reporter Strains with BACTEC Assay

In order to assess the suitability of using Mycobacterial reporter strains expressing FFlux for screening drug susceptibility, the minimum inhibitory concentration (MIC) values of seven antimycobacterial agents were determined by the radiometric BACTEC method and by using a mycobacterial reporter strain of the present invention. A culture of *Mycobacterium bovis* BCG containing the vector pMV361-lux, designated BCG:361-lux was cultured for three days at 37° C. in Middlebrook 7H9 broth supplemented with 10% (v/v) ADC enrichment and 0.5% (v/v) glycerol. The culture was assayed spectrophotometrically at 540 nm and diluted to yield two stock bacterial suspensions containing $4\times10^6$ colony forming units per milliliter (cfu/ml) and 1×10 5 cfu/ml respectively. The lower concentration suspension was distributed into test tubes in 4 ml volumes for the reporter strain (lux) assay. The high concentration suspension was injected in 0.1 ml volumes into BACTEC 12B vials to obtain a final bacterial concentration of $1\times10^5$ cfu/ml.

Stock solutions (10 mg/ml) of isoniazid, ethambutol, streptomycin, amikacin (all from Sigma, St. Louis, Mo., USA) and ciprofloxacin (Miles Inc., Tarrytown, N.Y., USA) were prepared in sterile deionized water. Rifampin (Sigma) and clarithromycin (Abbott Laboratories, North Chicago, Ill., USA) were prepared in dimethyl sulfoxide (DMSO). All antibiotic stock solutions were distributed in 0.2 ml volumes and stored at $-20°$ C. When required, the stock was thawed at room temperature and diluted with sterile deionized water to a concentration of 640 µg/ml. Further two-fold dilutions were prepared to obtain final concentrations of each antibiotic above, below, and at the MIC value reported for wild-type *Mycobacterium tuberculosis* strains. These were distributed in 0.1 ml volumes to both the BACTEC vials and the lux assay tubes, which were then incubated at 37° C. Radiometric readings, expressed as Growth Index (GI) units were obtained for each BACTEC vial using the BACTEC 460TB instrument. Daily Lux readings were also obtained by assay of 0.1 ml aliquots from each tube in an opaque white 96-well microtiter plate. Control wells containing BCG:361-lux in the absence of antibiotic were included. In addition, 25 µl aliquots were removed from each Lux assay tube and transferred to a plate of Middlebrook 7H10 agar medium for a semi-quantitative assessment of bactericidal activity. Plates were incubated at 37° C. for 21 days.

Readings were obtained with both systems until definitive MIC values were calculable with the BACTEC method (after five days). With the BACTEC system, the MIC was defined as the lowest concentration of antibiotic for which the change in GI units between day 4 and day 5 was less than or equal to the change in GI units for a control vial inoculated with a 1:100 dilution of the standard BACTEC inoculum. For the Lux system, the MIC value was defined as the lowest concentration of antibiotic which gave a lux reading less than or equal to $\frac{1}{100}$ the value obtained for antibiotic-free growth control.

Figure 2A:
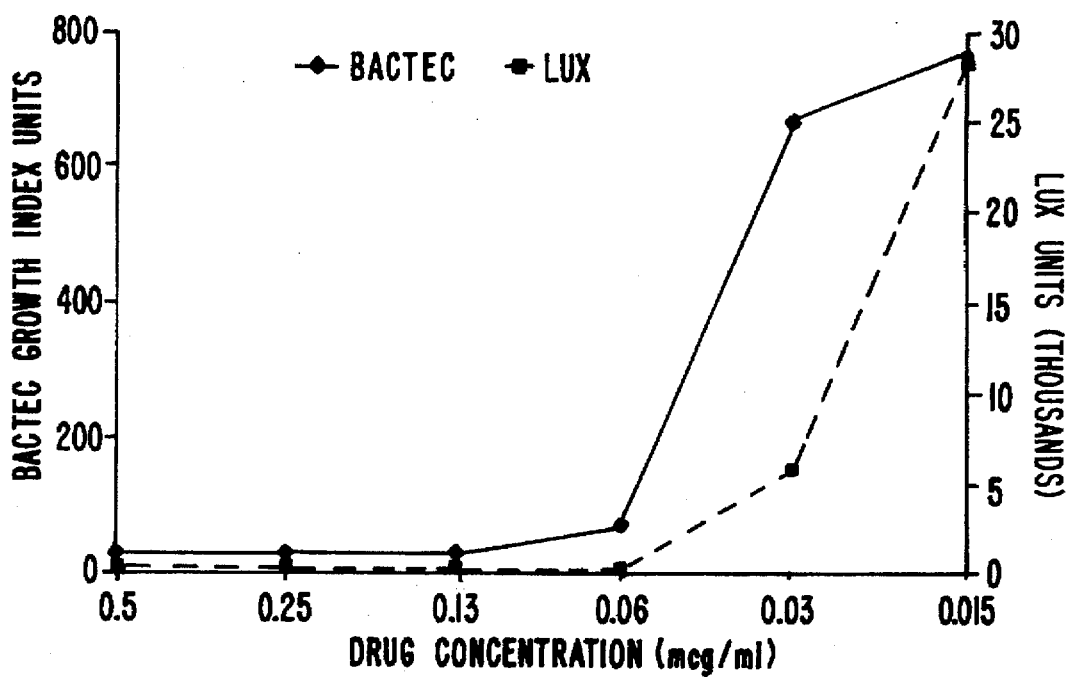
FIG. 2A and 2B show a comparison of the susceptibility of BCG to isoniazid as assayed by BACTEC and by the use of a recombinant BCG:pMV361-lux reporter strain. The similarity in BACTEC and BCG:pMV361-lux assays was comparable for ethambutol, rifampin, streptomycin, amikacin, ciprofloxin and clarithromycin.
Figure 2B:
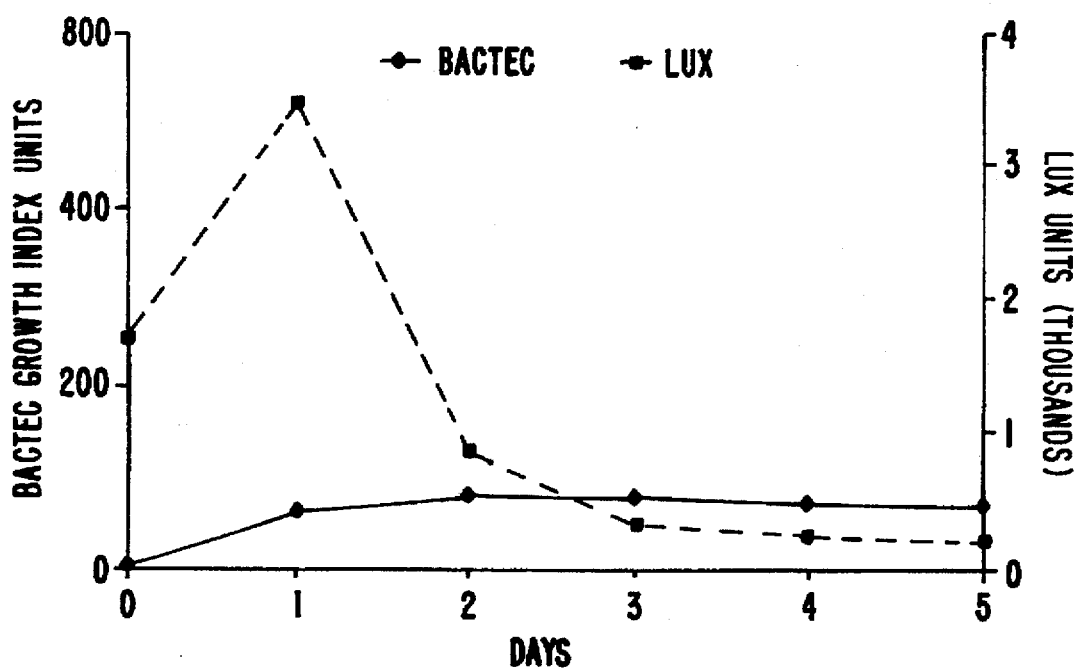

With the BACTEC method, MIC values can only be determined on the day the GI reading of the 1:100 control vial equals or exceeds a value of 20 (day 5 in this experiment). As can be seen from Table 2, there is very good agreement between MICs determined by the Lux and BACTEC systems on day 5, with a difference of not more than one two-fold dilution. In fact, MIC cutoffs could be determined one day faster with the Lux assay since results on days 4 and 5 were identical. However, MIC results determined by the lux assay on days 1, 2 and 3 were not reliable. FIG. 2 shows that the effects of drug concentration on the test strain on day 5 were equivalent when assessed both radiometrically and by luminometry as the curves appear very similar. At the Mic concentration, BACTEC GI values remain static or decrease slightly over time after day 1, whereas lux values decrease precipitously and then continue to fall more moderately until day 5.

As with the MIC determinations, MBCs assessed semi-quantitatively from the Lux assay tubes were identical on days 4 and 5 for all antibiotics and were very similar to the MIC values, except for clarithromycin, where the MBC value was above the highest concentration tested.

The reporter strain assay using BCG:361-lux is thus comparable to the traditional BACTEC method. Unlike the radiometric method, however, the Lux system is amenable to high throughput drug screening efforts due to the relatively low cost of materials and ease of handling. With the BACTEC system, expense is incurred not only with the initial purchase of the vials, but also in the eventual disposal of radioactive liquids. The MICs determined for the test strain were in the range expected for wild-type *M. tuberculosis*, indicating that this organism could be employed as a surrogate in screening strategies to identify novel antimycobacterial agents. Direct testing of *M. tuberculosis* would require all work to be performed in a specialized biosafety level 3 laboratory, whereas a screening effort utilizing BCG in this Lux assay could take place in a biosafety level 2 environment.

TABLE 2

Comparison of BACTEC and Lux assay data for six antimycobacterial agents.

| | Day | MIC BACTEC (µg/ml) | MIC Lux Assay (µg/ml) | MBC Lux Assay (µg/ml) |
|---|---|---|---|---|
| Isoniazid | 1 | | >0.5 | >0.5 |
| | 2 | | >0.5 | 0.13 |
| | 3 | | >0.5 | 0.13 |
| | 4 | | 0.06 | 0.13 |
| | 5 | 0.06 | 0.06 | 0.13 |
| Ethambutol | 1 | | >8 | >8 |
| | 2 | | >8 | 8 |
| | 3 | | >8 | 4–8 |
| | 4 | | 4 | 4 |
| | 5 | 2 | 4 | 4 |
| Streptomycin | 1 | | >2 | >2 |
| | 2 | | 1 | 0.5 |
| | 3 | | 0.5 | 0.5 |
| | 4 | | 0.25 | 0.25 |
| | 5 | 0.25 | 0.25 | 0.25 |
| Amikacin | 1 | | >2 | 2 |
| | 2 | | >2 | 0.5 |
| | 3 | | 0.5 | 0.5 |
| | 4 | | 0.25 | 0.25 |
| | 5 | 0.13 | 0.25 | 0.25 |
| Ciprofloxacin | 1 | | >2 | >2 |
| | 2 | | >2 | >2 |
| | 3 | | 0.5 | 2–1 |
| | 4 | | 0.5 | 0.5 |
| | 5 | 0.25 | 0.5 | 0.5 |
| Rifampin | 1 | | >0.25 | >0.25 |
| | 2 | | >0.25 | >0.25 |
| | 3 | | >0.25 | >0.25 |
| | 4 | | 0.06 | 0.13 |
| | 5 | 0.03 | 0.06 | 0.13 |
| Clarithromycin | 1 | | >0.5 | >0.5 |
| | 2 | | >0.5 | >0.5 |
| | 3 | | 0.5 | >0.5 |
| | 4 | | 0.25 | >0.5 |
| | 5 | 0.25 | 0.25 | >0.5 |

The bacterial inoculum for both assays was $10^4$–$10^5$ cfu/ml.

Example 3

Detection of Reporter Strains in Cell Culture Assays

A) Assay of Cell Culture

Recombinant BCG, MTB and MAC reporter strains were constructed for use in infected macrophage assays. Macrophages (THP-1 cells, American Type Culture Collection, Rockville, Md., USA) were cultured in RPMI 1640 supplemented with heat inactivated fetal bovine serum. Approximately 48 hours in advance of infection the THP-1 cells were transformed with PMA at 50 ng/ml). The cells were then applied to a 48 well plate at $4\times10^5$ cells/well in a volume of 1 ml/well. On the day of infection, the cell monolayer was washed on time with RPMI+10% FBS and 0.4 ml of the same media was added per well. Bacteria in log phase ($OD_{540}<1$) were dispersed by sonication using 0.10 second pulses for 20 seconds at an amplitude of 20 before using. The bacteria were infected with an MOI of 1:1 in volumes of 100 µl/well. The culture plate was placed in a 37° C.+5% $CO_2$ incubator and allowed to incubate for 4 hours. The cells were washed 5 times with 1X Hanks buffer or tissue culture media. The cells were then lysed using 0.2 ml PBS+1% Triton X-100 (BPS-TX100). Then 0.1 ml of this mixture was transferred to a Dynatech microtiter plate and the luminescence was measured as relative lux units (RLUs) in a luminometer as described below. This reading became timepoint 0.

Then fresh media was added to the wells containing unlysed control cells, while fresh media containing the test antibiotics isoniazid, rifampin, ethambutol, or amikacin was added to wells containing unlysed "test" cells. Both control and test cells were lysed daily to perform standard luminescence assays as described below.

Luciferin, obtained as a sodium salt (Sigma, St Louis, Mo., USA) was made up as a 100 mM stock in 100 mM $Na_3$-citrate at pH 5.1. The solution was stored frozen and kept in the dark until use. Prior to use, the solution was diluted to a final concentration of 1 mM with $Na_3$-citrate. The luciferin reagent was loaded into an EG&G Berthold model LB96P luminometer. This machine injects a standard volume of 100 µl of luciferin per well for assaying.

Assays were set up in a 96 well plate keeping the sample volume to 100 ml. In each well, 10 µl of cell lysate added to 90 µl of phosphate buffered saline pH 7.4 containing 1% Triton X-100. The luminometer was run integrating measurements over a 15 second sampling window, while the background measurement was integrated over a period of 0.5 sec.

All drug treatments demonstrated antimycobacterial activity within 10 days as measured by a reduction in luminescence of the treated samples compared to untreated controls.

Example 4

Detection of Reporter Strains in "Spiked" Organ Homogenates

Upon intravenous infection of mice with BCG, it is roughly estimated that approximately 5–10% of BCG end up in the spleen while 80–90% will end up in the liver. It is also known that BCG organ titers of $10^6$–$10^8$ colony forming units (cfu) per organ are readily achievable in spleens and livers. Based these estimates and the values of luminescence per colony forming unit (RLU/CFU) obtained for each of three rBCG-lux constructs, it appeared tenable that rBCG-lux luminescence could be measured in infected tissues. Because it was quite likely that a complex translucent mixture of enzymes, lipids, chromophores, and metabolites etc. could interfere (inhibit, or quench) with a standard luciferase assay, luciferase assay conditions were first investigated in mouse liver and spleen organ homogenates containing rBCG:pMH30-LUX added after tissue homogenization. Luminescence assays were performed in two luminometers, one employing a 96-well plate format and another using 12×75 mm tubes. All organ homogenate assays were performed in phosphate buffered saline (PBS) pH 7.4 using intact (unlysed) rBCG:pMH30-LUX derived from a log phase culture.

Inhibition of luminescence (measured as relative lux units) in the assay was approximately 80% in a 2.5% organ homogenate and 50% in a 0.5% homogenate for both spleens and livers in the 96-well format luminometer using a 100 µl assay containing undiluted spleen or liver homogenates equilibrated with assay buffer. This inhibition was significantly reduced as the organ homogenate was diluted. Luciferase assay inhibition was much less apparent or insignificant in a 100–200 µl assay performed in the tube format luminometer.

The effect of a non-ionic detergent such as Triton X-100 (TX-100) on the measurement of mycobacterial luminescence in organ homogenates was also investigated, as it was reasoned that TX-100 would lyse infected eukaryotic cells without lysing the mycobacteria. While the use of 1% TX-100 did not substantially enhance luminescence in these experiments, the use of the detergent was advantageous as it facilitated homogenization, reduced viscosity and eliminated congealing which increased over time in the absence of TX-100.

Aliquots from the rBCG-lux spiked organ homogenates maintained at room temperature or on ice were assayed at hourly intervals to determine the stability rBCG-lux in organ homogenates over time under normal laboratory conditions. Luminescence was remarkably consistent on spiked organ homogenates maintained on ice even after 4 hours and was reduced only 50% after 15 hours while luminescence from identical mixtures maintained at room temperature decreased approximately 50% within 4 hours. These data indicated that luminescence assay interference from organ homogenates was manageable, and that luminescence could be easily, reliably and consistently measured in a reasonable time frame after organ extraction and homogenization.

Example 4

Detection of Mycobacteria Reporter Strains in Infected Tissues

Mycobacterial reporter strain rBCG:pMH30-lux were grown in Middlebrook 7H9 broth supplemented with 10% ADC, 0.5% glycerol and 20 µg/ml kanamycin. Cultures were grown to reach an $OD_{540}$ of approximately 1.0 (log phase) on the day of injection. An aliquot and diluted 1:5 in 7H9 for determination of OD and lux activity. After these tests were done and immediately before injection, the bacteria were divided into 2 ml aliquots in polypropylene test tubes and dispersed by sonication for 20 sec. at 20% amplitude (cup horn). The bacteria were pooled and injected intravenously in the tail veins of mice using a 1 ml syringe with a 28 or 30 g needle. The injected volume was adjusted to approximately 150 µl to achieve a dosage of $1.5 \times 10^7$ BCG.

At 1, 4 and 24 hours following infection and treatment with drugs the animals were euthanized by cervical dislocation and the organs were removed aseptically and placed into a tared sterile Petri dish. Weights were recorded for all organs. The organs were then transferred into a sterile 50 ml tissue grinder and enough sterile PBS/1% Triton X-100 was added to make a 5% (wt./vol.) homogenate. If the organ weight was greater than 0.15 g, 3 ml of PBS-TX100 pH 7.4 was added initially. The tissue was ground with the pestle of the grinder for 1–2 minutes until the homogenate had no visible chunks. If necessary the volume was adjusted to make the 5% (wt/vol) final concentration of tissue to PBS-TX 100. The Triton X-100 was added to prevent congealing of the organ homogenate. This was found to improve the accuracy of the Lux assay and 1% of Triton X-100 did not inhibit the luminescence assay).

Spleens and livers were harvested and homogenized for luminescence assays at 1, 4, and 24 hours. The assay conditions determined in organ homogenate spiking experiments (see Example 4) were tested in infected organ homogenates. In contrast to organ homogenate spiking experiments, in which the rBCG-lux reporter strains was probably predominantly extracellular, TX-100 substantially enhanced (~5-fold) rBCG-lux luminescence in infected organ homogenates, suggesting that the non-ionic detergent lysed infected cells thereby enhancing the entry of the luciferin substrate into the rBCG-lux reporter strain. Luminescence was directly assayed and readily detected in infected organ homogenates without treatment to lyse the rBCG-lux reporter strain and without efforts to concentrate rBCG-lux bacteria from organ homogenates.

In the 96-well format luminometer, 10 µl of the 5% organ homogenate diluted with 90 µl of PBS-TX100 to make a 0.5% (wt/vol) final tissue concentration yielded approximately 500 RLUs. In the tube luminometer the same infected spleen homogenate yielded approximately 2000 RLUs. The rBCG-lux luminescence in infected organ homogenates transiently dropped between 0 and 24 hours. This observation was confirmed in subsequent experiments suggesting that rBCG-lux bacteria experience an environmental adjustment that is reflected in their ability to express luminescence. Thus it appeared that it would be possible and practical to assay infectious rBCG-lux organisms by luminescence in infected tissues providing the recombinant rBCG-lux strains would survive and grow in vivo.

Example 5

Survival Growth and Detection of Mycobacterial Reporter Strains In Vivo

To compare the three rBCG-lux strains in vivo and to investigate whether rBCG-lux strains were capable of surviving and growing beyond 1 day in mice separate groups of BALB/C mice (4–6 weeks) were intravenously infected, as described in Example 4, with approximately $10^7$ cfu of either rBCG:pMH30-lux, rBCG:pMV261-lux, or rBCG:pMV361-lux. Spleens were harvested and assayed for luminescence and colony forming units immediately after infection, and at 1, 3, 7, 10, and 14 days post infection.

In vivo growth curves based on direct organ homogenate luminescence assays (RLU) paralleled growth curves based on organ CFUs. The relative differences in in vivo FFlux expression were evident among the three rBCG-lux strains in their respective RLU:CFU ratios. As observed in vitro, the rBCG:pMH30-luxlux strain exhibited substantially greater luminescence in vivo than either rBCG:pMV261lux (at least 5 fold) or rBCG:pMV361-lux (at least 10 fold). However, in contrast to in vitro data, in vivo growth curves based on colony forming units over this 14 day period were comparable for each of 3 rBCG-lux strains. This result was somewhat surprising and in contrast to in vitro growth rates where rBCG constructs containing extrachromosomal expression vectors appeared significantly attenuated. Organ RLUs and CFUs peaked at approximately 10 days and waned thereafter. Consistency between individual mouse organ RLUs and CFUs in each group was reasonable between 1 and 10 days (SD<15%) after which standard deviations increased markedly.

Example 6

In Vivo Evaluation of Drug Susceptibility Using Mycobacterial Reporter Strains

Because of its superior luminescence, rBCG:pMH30-lux was selected for further investigation to determine whether in vivo lux technology could be used to test drug susceptibilities in vivo. BALB/C mice were infected with approximately $10^7$ colony forming units of log phase rBCG:pMH30-lux lux, as described above, and daily drug treatment was initiated in separate mouse groups 1 day after infection with isoniazid (25 mg/kg) and ethambutol (125 mg/kg). Experimental drug PA1648.1 was also administered daily to three additional mouse groups at either 25 mg/kg, 5 mg/kg, and 1 mg/kg. Spleens were harvested from untreated control mice 1 day after infection (day 0 of drug treatment) and in control mice and drug treated groups 1, 3, 7, and 10 days following the initiation of treatment and luciferase assays were performed directly on spleen homogenates.

Figure 3A:
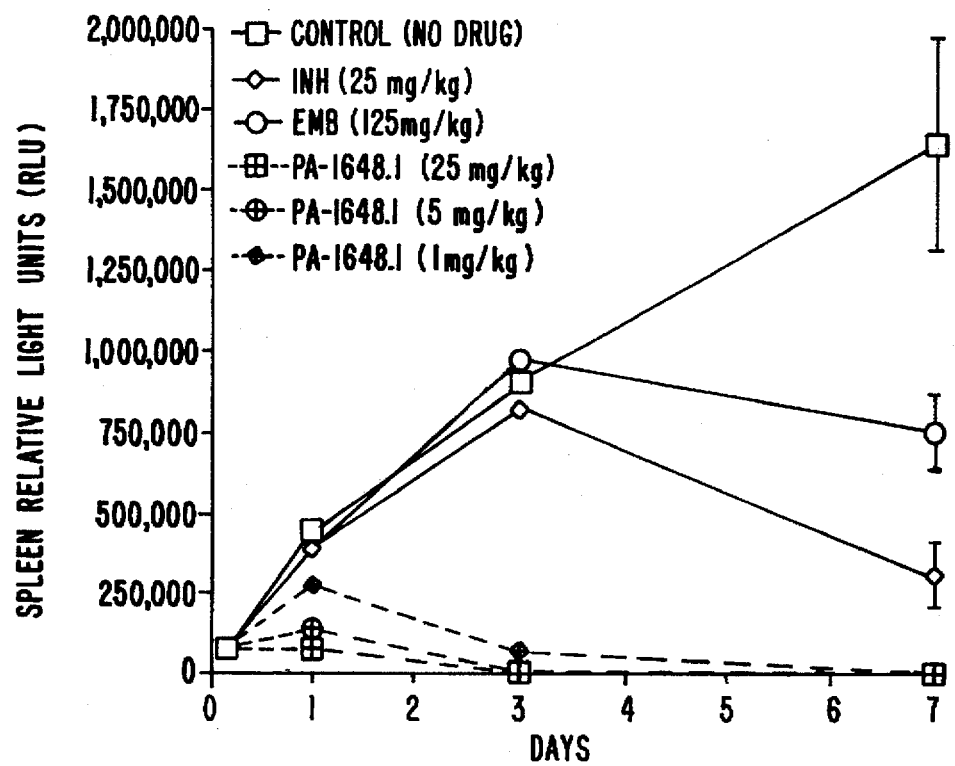
FIG. 3A and FIG. 3B show the results of an in vivo drug susceptibility for isoniazid (IHN), ethambutol (EMB) and PA-1648.1. Lux assays were performed utilizing rBCG:pMH30-lux, a BCG reporter strain comprising the pMH30-lux vector.
Figure 3B:
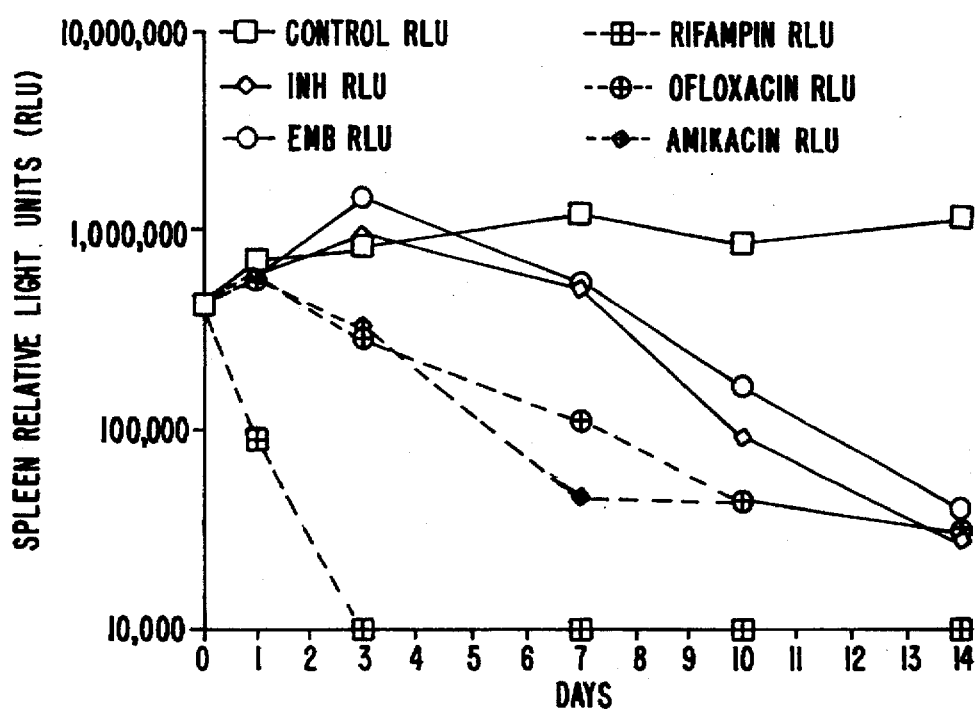

The results are illustrated in FIG. 3. In comparison to the untreated control groups, isoniazid and ethambutol treated groups exhibited reduced luminescence within 7 days of treatment initiation (50% and 30% reduction respectively). A total of reduction of 90% and 75% was observed for isoniazid and ethambutol after day 10 of treatment. PA1648.1 treated groups exhibited a more pronounced reduction in luminescence as early as 1 day after the initiation of treatment, indicating rapid in vivo activity for this rifampin derivative. A clear PA1648.1 dose dependant reduction in luminescence was also observed and treatment with PA1648.1 was terminated for all dose groups after the third daily dose as spleen luminescence was virtually undetectable in these groups. Increased luminescence was not observed in PA1648.1 groups at 4 or 7 days after treatment termination (days 7 or 10). Despite the relatively small mouse sample sizes for each time point, the observed reduction in rBCG-lux luminescence in drug treated groups was statistically significant at each time point indicating that in vivo antimycobacterial activity could be assayed by direct measurement of rBCG-lux luminescence reduction in spleens in comparison to untreated control groups.

As a further test of in vivo luminescence drug susceptibility testing, 5 drugs with different mechanisms of action and known in vivo antimycobacterial activity were selected for daily treatment of rBCG-lux infected animals. BALB/C mice were infected with approximately $10^7$ CFU of log phase rBCG:pMH30-lux and daily drug treatment was initiated in separate mouse groups 1 day after infection. In addition to the two cell wall active standard drugs isoniazid (INH) and ethambutol (EMB) tested in experiment 1, the transcriptional inhibitor rifampin (RIF), the quinolone DNA gyrase inhibitor ofloxacin (OFX) and the aminoglycoside translational inhibitor amikacin (AMK) were also tested using daily dosing of 20, 300, and 40 mg/kg respectively. As in experiment 1, spleens were harvested from untreated control mice 1 day after infection (day 0 of drug treatment) and in control mice and drug treated groups 1, 3, 7, and 10 days following the initiation of treatment and luciferase assays were performed directly on spleen homogenates. As in experiment 1, reduced lux activity was evident in the spleens of INH and EMB treated mice within 7 days of treatment while spleens from OFX and AMK treated mice exhibited substantially reduced lux activity in comparison to untreated control mice within 3 days of treatment initiation. As with the experimental PA1648.1 compound, spleens from rifampin treated mice exhibited reduced rBCG-lux luminescence within the first day of treatment. Thus, in vivo antimycobacterial activity was conveniently assayed by reduction in rBCG-lux luminescence in mouse spleens for 5 different drugs, each with different mechanisms of action, within 7–10 days of treatment initiation.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of quantifying mycobacteria in vivo, said method comprising the steps of:
   a) infecting a non-human animal with mycobacteria transfected with a vector comprising an FFlux reporter gene operably linked to a promoter such that the reporter gene is expressed at a level sufficient to allow detection of the reporter gene in tissue homogenates without lysis or concentration of said mycobacteria; and
   b) detecting the expression of said reporter gene in a tissue of said animal where the expression of the reporter gene indicates the quantity of mycobacteria present.

2. The method of claim 1 further comprising the step of administering an antimycobacterial composition to said animal after step (a) and before step (b) said method thereby determining the efficacy of said anti-mycobacterial composition against said mycobacteria in vivo.

3. The method of claim 1 further comprising the step of administering a prophylactic composition to said animal before step (a) said method thereby determining the efficacy of said prophylactic composition against said mycobacteria.

4. The method of claim 1, wherein said vector comprises a promoter selected from the group consisting of BCG:hsp60 and BCG:hsp70-tac.

5. The method of claim 4, wherein said vector is pMH30-lux.

6. The method of claim 1, wherein said reporter gene is expressed at levels at least 3 times greater than BCG:pMH261-lux when assayed in a luminometer.

7. The method of claim 1, wherein said reporter gene is FFlux in which an ATA codon is replaced with an ATC codon.

8. The method of claim 1, wherein said mycobacteria produce a luminescence level at least three times greater than a luminescence level produced by a BCG:pMV261-lux reporter strain, where said when said luminescence level is measured by contacting said mycobacteria and said BCG:pMV261-lux reporter strain with luciferin and detecting the resulting luminescence in a luminometer with said contacting and said detecting being under identical conditions for said mycobacteria and said BCG:pMV261-lux.

9. The method of claim 1, wherein said detecting comprises the steps of:
   removing a tissue from said animal;
   homogenizing said tissue to produce a homogenate;
   adding a solution comprising luciferin to said homogenate to produce luminescence; and
   detecting said luminescence.

10. The method of claim 9, wherein said homogenizing is in a solution comprising a buffer and a non-ionic detergent.

11. The method of claim 10 where said detecting is performed within about 1 to 14 days after commencing administration of the antimycobacterial compositions.

12. The method of claim 1, wherein said mycobacteria are selected from the group consisting of Mycobacterium tuberculosis, Mycobacterium intracellulare, Mycobacterium avium, Mycobacterium kansasii, Mycobacterium scrofulaceum, Mycobacterium bovis bacille Calmette-Guérin (BCG) and Mycobacterium leprae.

13. The method of claim 12, wherein said mycobacteria are Mycobacterium tuberculosis.

14. The method of claim 12, wherein said mycobacteria are Mycobacterium bovis bacille Calmette-Guérin (BCG).

15. The method of claim 1, wherein:
   said mycobacteria are Mycobacterium bovis bacille Calmette-Guérin (BCG);
   said vector is pMH30-lux;
   said reporter gene is FFLUx in which an ATA codon is replaced with an ATC codon; and
   said detecting comprises detecting luminescence produced by the mycobacteria in the presence of luciferin.

16. A method of quantifying mycobacteria in vitro, said method comprising the steps of:
   a) providing, in vitro, a mammalian cell containing one or more mycobacteria wherein said mycobacteria are transfected with a vector comprising an FFlux reporter gene operably linked to a promoter selected from the group consisting of BCG:hsp60 and BCG:hsp70-tac; and
   b) detecting the expression of the reporter gene in said mammalian cell where the expression of the reporter gene indicates the quantity of intracellular mycobacteria, said detecting being accomplished without lysis of said mycobacteria.

17. The method of claim 16 further comprising the step of administering an antimycobacterial composition to said cell before step (b) said method thereby determining the efficacy of said anti-mycobacterial composition against said mycobacteria.

18. The method of claim 16, wherein said detecting comprises the steps of:
   lysing said mammalian cell in a solution comprising a buffer and a detergent to produce a lysate;
   adding a solution comprising luciferin to said lysate to produce luminescence; and detecting said luminescence.

19. The method of claim 16, wherein said vector is selected from the group consisting of pMV261-lux, pMH30-lux and pMV361-lux.

20. A method of quantifying mycobacteria in vitro, said method comprising the steps of:
   a) providing a bacterial culture comprising infective mycobacteria wherein said mycobacteria are transfected with a vector comprising an FFlux reporter gene operably linked to a promoter selected from the group consisting of BCG:hsp60 and BCG:hsp70-tac;
   b) detecting the expression of the reporter gene in said bacterial culture where the expression of the reporter gene indicates the quantity of mycobacteria, said detecting being accomplished without lysis of said mycobacterium.

21. The method of claim 20 further comprising the step of administering an antimycobacterial composition to said mycobacteria before step (b) said method thereby determining the efficacy of said anti-mycobacterial composition against said mycobacteria.

22. The method of claim 20, wherein said detecting comprises the steps of:
   adding an aliquot of said bacterial culture to a solution comprising a buffer to produce a bacterial sample;
   adding a solution comprising luciferin to said bacterial sample to produce luminescence; and
   detecting said luminescence.

23. The method of claim 20, wherein said vector is selected from the group consisting of pMV261-lux, pMH30-lux and pMV361-lux.

24. The method of claim 20, wherein said reporter gene is an FFlux in which an ATA codon is replaced with an ATC codon.

25. An infective mycobacterial reporter strain, said strain comprising a mycobacterium, said mycobacterium being transfected with a vector expressing an FFlux reporter gene at a level sufficient to allow detection of said reporter gene without lysis or concentration of said mycobacterium.

26. The reporter strain of claim 25, wherein said reporter gene is an FFlux in which an ATA codon is replaced with an ATC codon.

27. The reporter strain of claim 26, wherein said FFlux is operably linked to a BCG:hsp70-tac promoter.

28. The reporter strain of claim 27, wherein said mycobacteria are selected from the group consisting of *Mycobacterium tuberculosis, Mycobacterium intracellulare, Mycobacterium avium, Mycobacterium kansasii, Mycobacterium scrofulaceum, Mycobacterium bovis, bacille* Calmette-Guérin (BCG) and *Mycobacterium leprae.*

29. The reporter strain of claim 28, wherein said mycobacteria are *Mycobacterium tuberculosis.*

30. The reporter strain of claim 28, wherein said mycobacteria are *bacille* Calmette-Guérin (BCG).

31. The reporter strain of claim 25 in which said vector is selected from the group consisting of pMV261-lux, pMH30-lux, and pMV361-lux.

32. The reporter strain of claim 31 in which said vector expresses the FFlux reporter gene at a level sufficient to allow detection of the reporter gene in organ homogenates without lysis or concentration of said mycobacteria.

33. The reporter strain of claim 32 in which said vector is pMH30-lux.

34. A vector comprising an FFlux reporter gene operably linked to a promoter such that infective mycobacteria transfected with the vector express the reporter gene at levels sufficient to permit detection without lysis or concentration of said mycobacteria.

35. The vector of claim 34, wherein said FFlux has an ATA codon replaced with an ATC codon.

36. The vector of claim 34, wherein said vector is pMH30-lux.

37. The vector of claim 34, wherein said vector is pMV361-lux.

38. The reporter strain of claim 20, wherein said mycobacteria are selected from the group consisting of *Mycobacterium tuberculosis, Mycobacterium intracellulare, Mycobacterium avium, Mycobacterium kansasii, Mycobacterium scrofulaceum, Mycobacterium bovis bacille* Calmette-Guérin and *Mycobacterium leprae.*

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (oligo)

( i x ) FEATURE:
        ( A ) NAME/KEY: misc_feature
        ( B ) LOCATION: 1..37
        ( D ) OTHER INFORMATION: /standard_name= "MCS2 5'"

( x i ) SEQUENCE DESCRIPTION: SEQ ID NO:1:

CTAGTCAGCT GCAGAATTCG AAGCTTAATT AATCGAT    3 7

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (oligo)

( i x ) FEATURE:
        ( A ) NAME/KEY: misc_feature
        ( B ) LOCATION: 1..37
        ( D ) OTHER INFORMATION: /standard_name= "MCS2 3'"

( x i ) SEQUENCE DESCRIPTION: SEQ ID NO:2:

CTAGATCGAT TAATTAAGCT TCGAATTCTG CAGCTGA    3 7

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (oligo)

( i x ) FEATURE:
        ( A ) NAME/KEY: misc_feature
        ( B ) LOCATION: 1..33

(D) OTHER INFORMATION: /standard_name= "T1T2 5'Bam"

(xi) SEQUENCE DESCRIPTION: SEQ ID NO:3:

CAGGATCCGA TGGTAGTGTG GGGTCTCCCC ATG       33

(2) INFORMATION FOR SEQ ID NO:4:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (oligo)

(ix) FEATURE:
            (A) NAME/KEY: misc_feature
            (B) LOCATION: 1..32
            (D) OTHER INFORMATION: /standard_name= "T1T2 3'Xba"

(xi) SEQUENCE DESCRIPTION: SEQ ID NO:4:

GCTCTAGATA TGACGACAGG AAGAGTTTGT AG       32

(2) INFORMATION FOR SEQ ID NO:5:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (oligo)

(ix) FEATURE:
            (A) NAME/KEY: misc_feature
            (B) LOCATION: 1..44
            (D) OTHER INFORMATION: /standard_name= "pPA208.MCS-5'"

(xi) SEQUENCE DESCRIPTION: SEQ ID NO:5:

CTAGATATCC ATGGATCCAG CGATGTCGAC GTAGTTAACG GTAC       44

(2) INFORMATION FOR SEQ ID NO:6:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (oligo)

(ix) FEATURE:
            (A) NAME/KEY: misc_feature
            (B) LOCATION: 1..36
            (D) OTHER INFORMATION: /standard_name= "pPA208.MCS-3'"

(xi) SEQUENCE DESCRIPTION: SEQ ID NO:6:

CGTTAACTAC GTCGACATCG CTGGATCCAT GGATAT       36

(2) INFORMATION FOR SEQ ID NO:7:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: DNA (oligo)

(ix) FEATURE:
            (A) NAME/KEY: misc_feature
            (B) LOCATION: 1..69

( D ) OTHER INFORMATION: /standard_name= "MOP 5'Xba"

( x i ) SEQUENCE DESCRIPTION: SEQ ID NO:7:

```
CTAGACCAGG CTTGACACTT TATGCTTCCG GCTCGTATAA TGTGTGGAAT TGTGAGCGCT      60

CACAATTCG                                                              69
```

( 2 ) INFORMATION FOR SEQ ID NO:8:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA (oligo)

( i x ) FEATURE:
        ( A ) NAME/KEY: misc_feature
        ( B ) LOCATION: 1..69
        ( D ) OTHER INFORMATION: /standard_name= "MOP 3'Bam"

( x i ) SEQUENCE DESCRIPTION: SEQ ID NO:8:

```
GATCCGAATT GTGAGCGCTC ACAATTCCAC ACATTATACG AGCCGGAAGC ATAAAGTGTC      60

AAGCCTGGT                                                              69
```

( 2 ) INFORMATION FOR SEQ ID NO:9:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (oligo)

( i x ) FEATURE:
        ( A ) NAME/KEY: misc_feature
        ( B ) LOCATION: 1..57
        ( D ) OTHER INFORMATION: /standard_name= "lux 5'BamHI"

( x i ) SEQUENCE DESCRIPTION: SEQ ID NO:9:

```
GCGGATCCAG GAGGAATCAC TCAATGGAAG ACGCCAAAAA CATCAAGAAA GGCCCGG        57
```

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (oligo)

( i x ) FEATURE:
        ( A ) NAME/KEY: misc_feature
        ( B ) LOCATION: 1..31
        ( D ) OTHER INFORMATION: /standard_name= "lux 3'Sal I"

( x i ) SEQUENCE DESCRIPTION: SEQ ID NO:10:

```
GCATGTCGAC GTCATCGCTG AATACAGTTA C                                    31
```

( 2 ) INFORMATION FOR SEQ ID NO:11:

( i ) SEQUENCE CHARACTERISTICS:
        ( A ) LENGTH: 4120 base pairs
        ( B ) TYPE: nucleic acid
        ( C ) STRANDEDNESS: single
        ( D ) TOPOLOGY: linear ( i i ) MOLECULE TYPE: DNA (plasmid)

( i x ) FEATURE:
    ( A ) NAME/KEY: misc_feature
    ( B ) LOCATION: 1..4120
    ( D ) OTHER INFORMATION: /standard_name= "plasmid pMV206"

( x i ) SEQUENCE DESCRIPTION: SEQ ID NO:11:

```
GCTAGCCAAC AAAGCGACGT TGTGTCTCAA AATCTCTGAT GTTACATTGC ACAAGATAAA      60
AATATATCAT CATGAACAAT AAAACTGTCT GCTTACATAA ACAGTAATAC AAGGGGTGTT     120
ATGAGCCATA TTCAACGGGA AACGTCTTGC TCGAGGCCGC GATTAAATTC CAACATGGAT     180
GCTGATTTAT ATGGGTATAA ATGGGCTCGC GATAATGTCG GGCAATCAGG TGCGACAATC     240
TATCGCTTGT ATGGGAAGCC CCATGCGCCA GAGTTGTTTC TGAAACATGG CAAAGGTAGC     300
GTTGCCAATG ATGTTACAGA TGAGATGGTC AGACTAAACT GGCTGACGGA ATTTATGCCT     360
CTTCCGACCA TCAAGCATTT TATCCGTACT CCTGATGATG CATGGTTACT CACCACTGCG     420
ATCCCCGGGA AAACAGCATT CCAGGTATTA GAAGAATATC CTGATTCAGG TGAAAATATT     480
GTTGATGCGC TGGCAGTGTT CCTGCGCCGG TTGCATTCGA TTCCTGTTTG TAATTGTCCT     540
TTTAACAGCG ATCGCGTATT TCGTCTCGCT CAGGCGCAAT CACGAATGAA TAACGGTTTG     600
GTTGATGCGA GTGATTTTGA TGACGAGCGT AATGGCTGGC CTGTTGAACA AGTCTGGAAA     660
GAAATGCATA ATCTTTTGCC ATTCTCACCG GATTCAGTCG TCACTCATGG TGATTTCTCA     720
CTTGATAACC TTATTTTTGA CGAGGGGAAA TTAATAGGTT GTATTGATGT TGGACGAGTC     780
GGAATCGCAG ACCGATACCA GGATCTTGCC ATCCTATGGA ACTGCCTCGG TGAGTTTTCT     840
CCTTCATTAC AGAAACGGCT TTTTCAAAAA TATGGTATTG ATAATCCTGA TATGAATAAA     900
TTGCAGTTTC ATTTGATGCT CGATGAGTTT TTCTAATCAG AATTGGTTAA TTGGTTGTAA     960
CACTGGCAGA GCATTACGCT GACTTGACGG GACGGCGGCT TGTTGAATA AATCGAACTT    1020
TTGCTGAGTT GAAGGATCAG ATCACGCATC TTCCCGACAA CGCAGACCGT TCCGTGGCAA    1080
AGCAAAAGTT CAAAATCACC AACTGGTCCA CCTACAACAA AGCTCTCATC AACCGTGGCT    1140
CCCTCACTTT CTGGCTGGAT GATGGGGCGA TTCAGGCCTG GTATGAGTCA GCAACACCTT    1200
CTTCACGAGG CAGACCTCAC TAGTTCCACT GAGCGTCAGA CCCCGTAGAA AAGATCAAAG    1260
GATCTTCTTG AGATCCTTTT TTTCTGCGCG TAATCTGCTG CTTGCAAACA AAAAAACCAC    1320
CGCTACCAGC GGTGGTTTGT TTGCCGGATC AAGAGCTACC AACTCTTTTT CCGAAGGTAA    1380
CTGGCTTCAG CAGAGCGCAG ATACCAAATA CTGTCCTTCT AGTGTAGCCG TAGTTAGGCC    1440
ACCACTTCAA GAACTCTGTA GCACCGCCTA CATACCTCGC TCTGCTAATC CTGTTACCAG    1500
TGGCTGCTGC CAGTGGCGAT AAGTCGTGTC TTACCGGGTT GGACTCAAGA CGATAGTTAC    1560
CGGATAAGGC GCAGCGGTCG GGCTGAACGG GGGGTTCGTG CACACAGCCC AGCTTGGAGC    1620
GAACGACCTA CACCGAACTG AGATACCTAC AGCGTGAGCA TTGAGAAAGC GCCACGCTTC    1680
CCGAAGGGAG AAAGGCGGAC AGGTATCCGG TAAGCGGCAG GGTCGGAACA GGAGAGCGCA    1740
CGAGGGAGCT TCCAGGGGGA AACGCCTGGT ATCTTTATAG TCCTGTCGGG TTTCGCCACC    1800
TCTGACTTGA GCGTCGATTT TTGTGATGCT CGTCAGGGGG GCGGAGCCTA TGGAAAAACG    1860
CCAGCAACGC GGCCTTTTTA CGGTTCCTGG CCTTTTGCTG GCCTTTTGCT CACATGTTCT    1920
TTCCTGCGTT ATCCCCTGAT TCTGTGGATA ACCGTATTAC CGCCTTTGAG TGAGCTGATA    1980
CCGCTCGCCG CAGCCGAACG ACCGAGCGCA ACGCGTGCGG CCGCACGCGT GAGCCCACCA    2040
GCTCCGTAAG TTCGGGCGCT GTGTGGCTCG TACCCGCGCA TTCAGGCGGC AGGGGGTCTA    2100
ACGGGTCTAA GGCGGCGTGT ACGGCCGCCA CAGCGGCTCT CAGCGGCCCG GAAACGTCCT    2160
```

| | | | | | | |
|---|---|---|---|---|---|---|
| CGAAACGACG | CATGTGTTCC | TCCTGGTTGG | TACAGGTGGT | TGGGGGTGCT | CGGCTGTCGC | 2220 |
| TGGTGTTCCA | CCACCAGGGC | TCGACGGGAG | AGCGGGGGAG | TGTGCAGTTG | TGGGGTGGCC | 2280 |
| CCTCAGCGAA | ATATCTGACT | TGGAGCTCGT | GTCGGACCAT | ACACCGGTGA | TTAATCGTGG | 2340 |
| TCTACTACCA | AGCGTGAGCC | ACGTCGCCGA | CGAATTTGAG | CAGCTCTGGC | TGCCGTACTG | 2400 |
| GCCGCTGGCA | AGCGACGATC | TGCTCGAGGG | GATCTACCGC | CAAAGCCGCG | CGTCGGCCCT | 2460 |
| AGGCCGCCGG | TACATCGAGG | CGAACCCAAC | AGCGCTGGCA | AACCTGCTGG | TCGTGGACGT | 2520 |
| AGACCATCCA | GACGCAGCGC | TCCGAGCGCT | CAGCGCCCGG | GGGTCCCATC | CGCTGCCCAA | 2580 |
| CGCGATCGTG | GGCAATCGCG | CCAACGGCCA | CGCACACGCA | GTGTGGGCAC | TCAACGCCCC | 2640 |
| TGTTCCACGC | ACCGAATACG | CGCGGCGTAA | GCCGCTCGCA | TACATGGCGG | CGTGCGCCGA | 2700 |
| AGGCCTTCGG | CGCGCCGTCG | ATGGCGACCG | CAGTTACTCA | GGCCTCATGA | CCAAAAACCC | 2760 |
| CGGCCACATC | GCCTGGGAAA | CGGAATGGCT | CCACTCAGAT | CTCTACACAC | TCAGCCACAT | 2820 |
| CGAGGCCGAG | CTCGGCGCGA | ACATGCCACC | GCCGCGCTGG | CGTCAGCAGA | CCACGTACAA | 2880 |
| AGCGGCTCCG | ACGCCGCTAG | GGCGGAATTG | CGCACTGTTC | GATTCCGTCA | GGTTGTGGGC | 2940 |
| CTATCGTCCC | GCCCTCATGC | GGATCTACCT | GCCGACCCGG | AACGTGGACG | GACTCGGCCG | 3000 |
| CGCGATCTAT | GCCGAGTGCC | ACGCGCGAAA | CGCCGAATTT | CCGTGCAACG | ACGTGTGTCC | 3060 |
| CGGACCGCTA | CCGGACAGCG | AGGTCCGCGC | CATCGCCAAC | AGCATTTGGC | GTTGGATCAC | 3120 |
| AACCAAGTCG | CGCATTTGGG | CGGACGGGAT | CGTGGTCTAC | GAGGCCACAC | TCAGTGCGCG | 3180 |
| CCAGTCGGCC | ATCTCGCGGA | AGGGCGCAGC | AGCGCGCACG | GCGGCGAGCA | CAGTTGCGCG | 3240 |
| GCGCGCAAAG | TCCGCGTCAG | CCATGCATGG | AGGCATTGCT | ATGAGCGACG | GCTACAGCGA | 3300 |
| CGGCTACAGC | GACGGCTACA | ACCGGCAGCC | GACTGTCCGC | AAAAAGCGGC | GCGTGACCGC | 3360 |
| CGCCGAAGGC | GCTCGAATCA | CCGGACTATC | CGAACGCCAC | GTCGTCCGGC | TCGTGGCGCA | 3420 |
| GGAACGCAGC | GAGTGGCTCG | CCGAGCAGGC | TGCACGCCGC | GAACGCATCC | GCGCCTATCA | 3480 |
| CGACGACGAG | GGCCACTCTT | GGCCGCAAAC | GGCCAAACAT | TTCGGGCTGC | ATCTGGACAC | 3540 |
| CGTTAAGCGA | CTCGGCTATC | GGGCGAGGAA | AGAGCGTGCG | GCAGAACAGG | AAGCGGCTCA | 3600 |
| AAAGGCCCAC | AACGAAGCCG | ACAATCCACC | GCTGTTCTAA | CGCAATTGGG | GAGCGGGTGT | 3660 |
| CGCGGGGGTT | CCGTGGGGGG | TTCCGTTGCA | ACGGGTCGGA | CAGGTAAAAG | TCCTGGTAGA | 3720 |
| CGCTAGTTTT | CTGGTTTGGG | CCATGCCTGT | CTCGTTGCGT | GTTTCGTTGC | GCCCGTTTTG | 3780 |
| AATACCAGCC | AGACGAGACG | GGGTTCTACG | AATCTTGGTC | GATACCAAGC | CATTTCCGCT | 3840 |
| GAATATCGGG | GAGCTCACCG | CCAGAATCGG | TGGTTGTGGT | GATGTACGTG | GCGAACTCCG | 3900 |
| TTGTAGTGTT | GTGGTGGCAT | CCGTGGCGCG | GCCGCGGTAC | CAGATCTTTA | AATCTAGATA | 3960 |
| TCCATGGATC | CAGCTGCAGA | ATTCGAAGCT | TATCGATGTC | GACGTAGTTA | ACTAGCGTAC | 4020 |
| GATCGACTGC | CAGGCATCAA | ATAAAACGAA | AGGCTCAGTC | GAAAGACTGG | GCCTTTCGTT | 4080 |
| TTATCTGTTG | TTTGTCCGGC | CATCATGGCC | GCGGTGATCA | | | 4120 |

( 2 ) INFORMATION FOR SEQ ID NO:12:

( i ) SEQUENCE CHARACTERISTICS:
        ( A ) LENGTH: 6047 base pairs
        ( B ) TYPE: nucleic acid
        ( C ) STRANDEDNESS: single
        ( D ) TOPOLOGY: linear ( i i ) MOLECULE TYPE: DNA (plasmid)

( i x ) FEATURE:
        ( A ) NAME/KEY: misc_feature
        ( B ) LOCATION: 1..6047

(D) OTHER INFORMATION: /standard_name= "plasmid pMH30-lux"

(xi) SEQUENCE DESCRIPTION: SEQ ID NO:12:

| | | | | | |
|---|---|---|---|---|---|
| GCTAGCCAAC | AAAGCGACGT | TGTGTCTCAA | AATCTCTGAT | GTTACATTGC | ACAAGATAAA | 60
| AATATATCAT | CATGAACAAT | AAAACTGTCT | GCTTACATAA | ACAGTAATAC | AAGGGGTGTT | 120
| ATGAGCCATA | TTCAACGGGA | AACGTCTTGC | TCGAGGCCGC | GATTAAATTC | CAACATGGAT | 180
| GCTGATTTAT | ATGGGTATAA | ATGGGCTCGC | GATAATGTCG | GGCAATCAGG | TGCGACAATC | 240
| TATCGCTTGT | ATGGGAAGCC | CCATGCGCCA | GAGTTGTTTC | TGAAACATGG | CAAAGGTAGC | 300
| GTTGCCAATG | ATGTTACAGA | TGAGATGGTC | AGACTAAACT | GGCTGACGGA | ATTTATGCCT | 360
| CTTCCGACCA | TCAAGCATTT | TATCCGTACT | CCTGATGATG | CATGGTTACT | CACCACTGCG | 420
| ATCCCCGGGA | AAACAGCATT | CCAGGTATTA | GAAGAATATC | CTGATTCAGG | TGAAAATATT | 480
| GTTGATGCGC | TGGCAGTGTT | CCTGCGCCGG | TTGCATTCGA | TTCCTGTTTG | TAATTGTCCT | 540
| TTTAACAGCG | ATCGCGTATT | TCGTCTCGCT | CAGGCGCAAT | CACGAATGAA | TAACGGTTTG | 600
| GTTGATGCGA | GTGATTTTGA | TGACGAGCGT | AATGGCTGGC | CTGTTGAACA | AGTCTGGAAA | 660
| GAAATGCATA | ATCTTTTGCC | ATTCTCACCG | GATTCAGTCG | TCACTCATGG | TGATTTCTCA | 720
| CTTGATAACC | TTATTTTTGA | CGAGGGGAAA | TTAATAGGTT | GTATTGATGT | TGGACGAGTC | 780
| GGAATCGCAG | ACCGATACCA | GGATCTTGCC | ATCCTATGGA | ACTGCCTCGG | TGAGTTTTCT | 840
| CCTTCATTAC | AGAAACGGCT | TTTTCAAAAA | TATGGTATTG | ATAATCCTGA | TATGAATAAA | 900
| TTGCAGTTTC | ATTTGATGCT | CGATGAGTTT | TTCTAATCAG | AATTGGTTAA | TTGGTTGTAA | 960
| CACTGGCAGA | GCATTACGCT | GACTTGACGG | GACGGCGGCT | TTGTTGAATA | AATCGAACTT | 1020
| TTGCTGAGTT | GAAGGATCAG | ATCACGCATC | TTCCCGACAA | CGCAGACCGT | TCCGTGGCAA | 1080
| AGCAAAAGTT | CAAAATCACC | AACTGGTCCA | CCTACAACAA | AGCTCTCATC | AACCGTGGCT | 1140
| CCCTCACTTT | CTGGCTGGAT | GATGGGGCGA | TTCAGGCCTG | GTATGAGTCA | GCAACACCTT | 1200
| CTTCACGAGG | CAGACCTCAC | TAGTCAGCTG | CAGAATTCGA | AGCTTAATTA | ATCGATCTAG | 1260
| TTCCACTGAG | CGTCAGACCC | CGTAGAAAAG | ATCAAAGGAT | CTTCTTGAGA | TCCTTTTTTT | 1320
| CTGCGCGTAA | TCTGCTGCTT | GCAAACAAAA | AAACCACCGC | TACCAGCGGT | GGTTTGTTTG | 1380
| CCGGATCAAG | AGCTACCAAC | TCTTTTTCCG | AAGGTAACTG | GCTTCAGCAG | AGCGCAGATA | 1440
| CCAAATACTG | TCCTTCTAGT | GTAGCCGTAG | TTAGGCCACC | ACTTCAAGAA | CTCTGTAGCA | 1500
| CCGCCTACAT | ACCTCGCTCT | GCTAATCCTG | TTACCAGTGG | CTGCTGCCAG | TGGCGATAAG | 1560
| TCGTGTCTTA | CCGGGTTGGA | CTCAAGACGA | TAGTTACCGG | ATAAGGCGCA | GCGGTCGGGC | 1620
| TGAACGGGGG | GTTCGTGCAC | ACAGCCCAGC | TTGGAGCGAA | CGACCTACAC | CGAACTGAGA | 1680
| TACCTACAGC | GTGAGCATTG | AGAAAGCGCC | ACGCTTCCCG | AAGGGAGAAA | GGCGGACAGG | 1740
| TATCCGGTAA | GCGGCAGGGT | CGGAACAGGA | GAGCGCACGA | GGGAGCTTCC | AGGGGGAAAC | 1800
| GCCTGGTATC | TTTATAGTCC | TGTCGGGTTT | CGCCACCTCT | GACTTGAGCG | TCGATTTTTG | 1860
| TGATGCTCGT | CAGGGGGGCG | GAGCCTATGG | AAAAACGCCA | GCAACGCGGC | CTTTTTACGG | 1920
| TTCCTGGCCT | TTTGCTGGCC | TTTTGCTCAC | ATGTTCTTTC | CTGCGTTATC | CCCTGATTCT | 1980
| GTGGATAACC | GTATTACCGC | CTTTGAGTGA | GCTGATACCG | CTCGCCGCAG | CCGAACGACC | 2040
| GAGCGCAACG | CGTGAGCCCA | CCAGCTCCGT | AAGTTCGGGC | GCTGTGTGGC | TCGTACCCGC | 2100
| GCATTCAGGC | GGCAGGGGGT | CTAACGGGTC | TAAGGCGGCG | TGTACGGCCG | CCACAGCGGC | 2160
| TCTCAGCGGC | CCGGAAACGT | CCTCGAAACG | ACGCATGTGT | TCCTCCTGGT | TGGTACAGGT | 2220
| GGTTGGGGGT | GCTCGGCTGT | CGCTGGTGTT | CCACCACCAG | GGCTCGACGG | GAGAGCGGGG | 2280

| | | | | | |
|---|---|---|---|---|---|
| GAGTGTGCAG | TTGTGGGGTG | GCCCCTCAGC | GAAATATCTG | ACTTGGAGCT | CGTGTCGGAC | 2340 |
| CATACACCGG | TGATTAATCG | TGGTCTACTA | CCAAGCGTGA | GCCACGTCGC | CGACGAATTT | 2400 |
| GAGCAGCTCT | GGCTGCCGTA | CTGGCCGCTG | GCAAGCGACG | ATCTGCTCGA | GGGGATCTAC | 2460 |
| CGCCAAAGCC | GCGCGTCGGC | CCTAGGCCGC | CGGTACATCG | AGGCGAACCC | AACAGCGCTG | 2520 |
| GCAAACCTGC | TGGTCGTGGA | CGTAGACCAT | CCAGACGCAG | CGCTCCGAGC | GCTCAGCGCC | 2580 |
| CGGGGGTCCC | ATCCGCTGCC | CAACGCGATC | GTGGGCAATC | GCGCCAACGG | CCACGCACAC | 2640 |
| GCAGTGTGGG | CACTCAACGC | CCCTGTTCCA | CGCACCGAAT | ACGCGCGGCG | TAAGCCGCTC | 2700 |
| GCATACATGG | CGGCGTGCGC | CGAAGGCCTT | CGGCGCGCCG | TCGATGGCGA | CCGCAGTTAC | 2760 |
| TCAGGCCTCA | TGACCAAAAA | CCCCGGCCAC | ATCGCCTGGG | AAACGGAATG | GCTCCACTCA | 2820 |
| GATCTCTACA | CACTCAGCCA | CATCGAGGCC | GAGCTCGGCG | CGAACATGCC | ACCGCCGCGC | 2880 |
| TGGCGTCAGC | AGACCACGTA | CAAAGCGGCT | CCGACGCCGC | TAGGGCGGAA | TTGCGCACTG | 2940 |
| TTCGATTCCG | TCAGGTTGTG | GGCCTATCGT | CCCGCCCTCA | TGCGGATCTA | CCTGCCGACC | 3000 |
| CGGAACGTGG | ACGGACTCGG | CCGCGCGATC | TATGCCGAGT | GCCACGCGCG | AAACGCCGAA | 3060 |
| TTTCCGTGCA | ACGACGTGTG | TCCCGGACCG | CTACCGGACA | GCGAGGTCCG | CGCCATCGCC | 3120 |
| AACAGCATTT | GGCGTTGGAT | CACAACCAAG | TCGCGCATTT | GGGCGGACGG | GATCGTGGTC | 3180 |
| TACGAGGCCA | CACTCAGTGC | GCGCCAGTCG | GCCATCTCGC | GGAAGGGCGC | AGCAGCGCGC | 3240 |
| ACGGCGGCGA | GCACAGTTGC | GCGGCGCGCA | AAGTCCGCGT | CAGCCATGCA | TGGAGGCATT | 3300 |
| GCTATGAGCG | ACGGCTACAG | CGACGGCTAC | AGCGACGGCT | ACAACCGGCA | GCCGACTGTC | 3360 |
| CGCAAAAAGC | GGCGCGTGAC | CGCCGCCGAA | GGCGCTCGAA | TCACCGGACT | ATCCGAACGC | 3420 |
| CACGTCGTCC | GGCTCGTGGC | GCAGGAACGC | AGCGAGTGGC | TCGCCGAGCA | GGCTGCACGC | 3480 |
| CGCGAACGCA | TCCGCGCCTA | TCACGACGAC | GAGGGCCACT | CTTGGCCGCA | AACGGCCAAA | 3540 |
| CATTTCGGGC | TGCATCTGGA | CACCGTTAAG | CGACTCGGCT | ATCGGGCGAG | GAAAGAGCGT | 3600 |
| GCGGCAGAAC | AGGAAGCGGC | TCAAAAGGCC | CACAACGAAG | CCGACAATCC | ACCGCTGTTC | 3660 |
| TAACGCAATT | GGGGAGCGGG | TGTCGCGGGG | GTTCCGTGGG | GGGTTCCGTT | GCAACGGGTC | 3720 |
| GGACAGGTAA | AAGTCCTGGT | AGACGCTAGT | TTTCTGGTTT | GGGCCATGCC | TGTCTCGTTG | 3780 |
| CGTGTTTCGT | TGCGCCCGTT | TTGAATACCA | GCCAGACGAG | ACGGGGTTCT | ACGAATCTTG | 3840 |
| GTCGATACCA | AGCCATTTCC | GCTGAATATC | GGGGAGCTCA | CCGCCAGAAT | CGGTGGTTGT | 3900 |
| GGTGATGTAC | GTGGCGAACT | CCGTTGTAGT | GTTGTGGTGG | CATCCGTGGC | GCGGCCGCGG | 3960 |
| TACCGTTAAC | TACGTCGACA | TCGCTGACGT | CATCGCTGAA | TACAGTTACA | TTTTACAATT | 4020 |
| TGGACTTTCC | GCCCTTCTTG | GCCTTTATGA | GGATCTCTCT | GATTTTTCTT | GCGTCGAGTT | 4080 |
| TTCCGGTAAG | ACCTTTCGGT | ACTTCGTCCA | CAAACACAAC | TCCTCCGCGC | AACTTTTTCG | 4140 |
| CGGTTGTTAC | TTGACTGGCG | ACGTAATCCA | CGATCTCTTT | TTCCGTCATC | GTCTTTCCGT | 4200 |
| GCTCCAAAAC | AACAACGGCG | GCGGGAAGTT | CACCGGCGTC | ATCGTCGGGA | AGACCTGCCA | 4260 |
| CGCCCGCGTC | GAAGATGTTG | GGGTGTTGTA | ACAATATCGA | TTCCAATTCA | GCGGGGGCCA | 4320 |
| CCTGATATCC | TTTGTATTTA | ATTAAAGACT | TCAAGCGGTC | AACTATGAAG | AAGTGTTCGT | 4380 |
| CTTCGTCCCA | GTAAGCTATG | TCTCCAGAAT | GTAGCCATCC | ATCCTTGTCA | ATCAAGGCGT | 4440 |
| TGGTCGCTTC | CGGATTGTTT | ACATAACCGG | ACATAATCAT | AGGTCCTCTG | ACACATAATT | 4500 |
| CGCCTCTCTG | ATTAACGCCC | AGCGTTTTCC | CGGTATCCAG | ATCCACAACC | TTCGCTTCAA | 4560 |
| AAAATGGAAC | AACTTTACCG | ACCGCGCCCG | GTTTATCATC | CCCCTCGGGT | GTAATCAGAA | 4620 |
| TAGCTGATGT | AGTCTCAGTG | AGCCCATATC | CTTGTCGTAT | CCCTGGAAGA | TGGAAGCGTT | 4680 |

```
TTGCAACCGC TTCCCCGACT TCTTTCGAAA GAGGTGCGCC CCCAGAAGCA ATTTCGTGTA    4740

AATTAGATAA ATCGTATTTG TCAATCAGAG TGCTTTTGGC GAAGAATGAA AATAGGGTTG    4800

GTACTAGCAA CGCACTTTGA ATTTTGTAAT CCTGAAGGGA TCGTAAAAAC AGCTCTTCTT    4860

CAAATCTATA CATTAAGACG ACTCGAAATC CACATATCAA ATATCCGAGT GTAGTAAACA    4920

TTCCAAAACC GTGATGGAAT GGAACAACAC TTAAAATCGC AGTATCCGGA ATGATTTGAT    4980

TGCCAAAAAT AGGATCTCTG GCATGCGAGA ATCTGACGCA GGCAGTTCTA TGCGGAAGGG    5040

CCACACCCTT AGGTAACCCA GTAGATCCAG AGGAATTCAT TATCAGTGCA ATTGTTTTGT    5100

CACGATCAAA GGACTCTGGT ACAAAATCGT ATTCATTAAA ACCGGGAGGT AGATGAGATG    5160

TGACGAACGT GTACATCGAC TGAAATCCCT GGTAATCCGT TTAGAATCC  ATGATAATAA    5220

TTTTCTGGAT TATTGGTAAT TTTTTTTGCA CGTTCAAAAT TTTTGCAAC  CCCTTTTTGG    5280

AAACAAACAC TACGGTAGGC TGCGAAATGT TCATACTGTT GAGCAATTCA CGTTCATTAT    5340

AAATGTCGTT CGCGGGCGCA ACTGCAACTC CGATAAATAA CGCGCCCAAC ACCGGCATAA    5400

AGAATTGAAG AGAGTTTTCA CTGCATACGA CGATTCTGTG ATTTGTATTC AGCCCATATC    5460

GTTTCATAGC TTCTGCCAAC CGAACGGACA TTTCGAAGTA TTCCGCGTAC GTGATGTTCA    5520

CCTCGATATG TGCATCTGTA AAAGCAATTG TTCCAGGAAC CAGGGCGTAT CTCTTCATAG    5580

CCTTATGCAG TTGCTCTCCA GCGGTTCCAT CCTCTAGAGG ATAGAATGGC GCCGGGCCTT    5640

TCTTGATGTT TTTGGCGTCT TCCATTGAGT GATTCCTCCT GGATCCGAAT TGTGAGCGCT    5700

CACAATTCCA CACATTATAC GAGCCGGAAG CATAAAGTGT CAAGCCTGGT CTAGATATGA    5760

CGACAGGAAG AGTTTGTAGA AACGCAAAAA GGCCATCCGT CAGGATGGCC TTCTGCTTAA    5820

TTTGATGCCT GGCAGTTTAT GGCGGGCGTC CTGCCCGCCA CCCTCCGGGC CGTTGCTTCG    5880

CAACGTTCAA ATCCGCTCCC GGCGGATTTG TCCTACTCAG GAGAGCGTTC ACCGACAAAC    5940

AACAGATAAA ACGAAAGGCC CAGTCTTTCG ACTGAGCCTT TCGTTTTATT TGATGCCTGG    6000

CAGTTCCCTA CTCTCGCATG GGGAGACCCC ACACTACCAT CTGATCC               6047
```

( 2 ) INFORMATION FOR SEQ ID NO:13:

( i ) SEQUENCE CHARACTERISTICS:
        ( A ) LENGTH: 4505 base pairs
        ( B ) TYPE: nucleic acid
        ( C ) STRANDEDNESS: single
        ( D ) TOPOLOGY: linear ( i i ) MOLECULE TYPE: DNA (plasmid)

( i x ) FEATURE:
        ( A ) NAME/KEY: misc_feature
        ( B ) LOCATION: 1..4505
        ( D ) OTHER INFORMATION: /standard_name= "plasmid pMV261"

( x i ) SEQUENCE DESCRIPTION: SEQ ID NO:13:

```
GCTAGCCAAC AAAGCGACGT TGTGTCTCAA AATCTCTGAT GTTACATTGC ACAAGATAAA      60

AATATATCAT CATGAACAAT AAAACTGTCT GCTTACATAA ACAGTAATAC AAGGGGTGTT     120

ATGAGCCATA TTCAACGGGA AACGTCTTGC TCGAGGCCGC GATTAAATTC CAACATGGAT     180

GCTGATTTAT ATGGGTATAA ATGGGCTCGC GATAATGTCG GCAATCAGG  TGCGACAATC     240

TATCGCTTGT ATGGGAAGCC CCATGCGCCA GAGTTGTTTC TGAAACATGG CAAAGGTAGC     300

GTTGCCAATG ATGTTACAGA TGAGATGGTC AGACTAAACT GGCTGACGGA ATTTATGCCT     360

CTTCCGACCA TCAAGCATTT TATCCGTACT CCTGATGATG CATGGTTACT CACCACTGCG     420

ATCCCCGGGA AAACAGCATT CCAGGTATTA GAAGAATATC CTGATTCAGG TGAAAATATT     480
```

| | | | | | |
|---|---|---|---|---|---|
| GTTGATGCGC | TGGCAGTGTT | CCTGCGCCGG | TTGCATTCGA | TTCCTGTTTG | TAATTGTCCT | 540
| TTTAACAGCG | ATCGCGTATT | TCGTCTCGCT | CAGGCGCAAT | CACGAATGAA | TAACGGTTTG | 600
| GTTGATGCGA | GTGATTTTGA | TGACGAGCGT | AATGGCTGGC | CTGTTGAACA | AGTCTGGAAA | 660
| GAAATGCATA | ATCTTTTGCC | ATTCTCACCG | GATTCAGTCG | TCACTCATGG | TGATTCTCA | 720
| CTTGATAACC | TTATTTTTGA | CGAGGGGAAA | TTAATAGGTT | GTATTGATGT | TGGACGAGTC | 780
| GGAATCGCAG | ACCGATACCA | GGATCTTGCC | ATCCTATGGA | ACTGCCTCGG | TGAGTTTTCT | 840
| CCTTCATTAC | AGAAACGGCT | TTTTCAAAAA | TATGGTATTG | ATAATCCTGA | TATGAATAAA | 900
| TTGCAGTTTC | ATTTGATGCT | CGATGAGTTT | TTCTAATCAG | AATTGGTTAA | TTGGTTGTAA | 960
| CACTGGCAGA | GCATTACGCT | GACTTGACGG | GACGGCGGCT | TTGTTGAATA | AATCGAACTT | 1020
| TTGCTGAGTT | GAAGGATCAG | ATCACGCATC | TTCCCGACAA | CGCAGACCGT | TCCGTGGCAA | 1080
| AGCAAAAGTT | CAAAATCACC | AACTGGTCCA | CCTACAACAA | AGCTCTCATC | AACCGTGGCT | 1140
| CCCTCACTTT | CTGGCTGGAT | GATGGGGCGA | TTCAGGCCTG | GTATGAGTCA | GCAACACCTT | 1200
| CTTCACGAGG | CAGACCTCAC | TAGTTCCACT | GAGCGTCAGA | CCCCGTAGAA | AGATCAAAG | 1260
| GATCTTCTTG | AGATCCTTTT | TTTCTGCGCG | TAATCTGCTG | CTTGCAAACA | AAAAAACCAC | 1320
| CGCTACCAGC | GGTGGTTTGT | TTGCCGGATC | AAGAGCTACC | AACTCTTTTT | CCGAAGGTAA | 1380
| CTGGCTTCAG | CAGAGCGCAG | ATACCAAATA | CTGTCCTTCT | AGTGTAGCCG | TAGTTAGGCC | 1440
| ACCACTTCAA | GAACTCTGTA | GCACCGCCTA | CATACCTCGC | TCTGCTAATC | CTGTTACCAG | 1500
| TGGCTGCTGC | CAGTGGCGAT | AAGTCGTGTC | TTACCGGGTT | GGACTCAAGA | CGATAGTTAC | 1560
| CGGATAAGGC | GCAGCGGTCG | GGCTGAACGG | GGGGTTCGTG | CACACAGCCC | AGCTTGGAGC | 1620
| GAACGACCTA | CACCGAACTG | AGATACCTAC | AGCGTGAGCA | TTGAGAAAGC | GCCACGCTTC | 1680
| CCGAAGGGAG | AAAGGCGGAC | AGGTATCCGG | TAAGCGGCAG | GGTCGGAACA | GGAGAGCGCA | 1740
| CGAGGGAGCT | TCCAGGGGGA | AACGCCTGGT | ATCTTTATAG | TCCTGTCGGG | TTTCGCCACC | 1800
| TCTGACTTGA | GCGTCGATTT | TTGTGATGCT | CGTCAGGGGG | GCGGAGCCTA | TGGAAAAACG | 1860
| CCAGCAACGC | GGCCTTTTTA | CGGTTCCTGG | CCTTTTGCTG | GCCTTTTGCT | CACATGTTCT | 1920
| TTCCTGCGTT | ATCCCCTGAT | TCTGTGGATA | ACCGTATTAC | CGCCTTTGAG | TGAGCTGATA | 1980
| CCGCTCGCCG | CAGCCGAACG | ACCGAGCGCA | ACGCGTGCGG | CCGCACGCGT | GAGCCCACCA | 2040
| GCTCCGTAAG | TTCGGGCGCT | GTGTGGCTCG | TACCCGCGCA | TTCAGGCGGC | AGGGGGTCTA | 2100
| ACGGGTCTAA | GGCGGCGTGT | ACGGCCGCCA | CAGCGGCTCT | CAGCGGCCCG | GAAACGTCCT | 2160
| CGAAACGACG | CATGTGTTCC | TCCTGGTTGG | TACAGGTGGT | TGGGGGTGCT | CGGCTGTCGC | 2220
| TGGTGTTCCA | CCACCAGGGC | TCGACGGGAG | AGCGGGGAG | TGTGCAGTTG | TGGGGTGGCC | 2280
| CCTCAGCGAA | ATATCTGACT | TGGAGCTCGT | GTCGGACCAT | ACACCGGTGA | TTAATCGTGG | 2340
| TCTACTACCA | AGCGTGAGCC | ACGTCGCCGA | CGAATTTGAG | CAGCTCTGGC | TGCCGTACTG | 2400
| GCCGCTGGCA | AGCGACGATC | TGCTCGAGGG | GATCTACCGC | CAAAGCCGCG | CGTCGGCCCT | 2460
| AGGCCGCCGG | TACATCGAGG | CGAACCCAAC | AGCGCTGGCA | AACCTGCTGG | TCGTGGACGT | 2520
| AGACCATCCA | GACGCAGCGC | TCCGAGCGCT | CAGCGCCCGG | GGGTCCCATC | CGCTGCCCAA | 2580
| CGCGATCGTG | GGCAATCGCG | CCAACGGCCA | CGCACACGCA | GTGTGGGCAC | TCAACGCCCC | 2640
| TGTTCCACGC | ACCGAATACG | CGCGGCGTAA | GCCGCTCGCA | TACATGGCGG | CGTGCGCCGA | 2700
| AGGCCTTCGG | CGCGCCGTCG | ATGGCGACCG | CAGTTACTCA | GGCCTCATGA | CCAAAAACCC | 2760
| CGGCCACATC | GCCTGGGAAA | CGGAATGGCT | CCACTCAGAT | CTCTACACAC | TCAGCCACAT | 2820
| CGAGGCCGAG | CTCGGCGCGA | ACATGCCACC | GCCGCGCTGG | CGTCAGCAGA | CCACGTACAA | 2880

-continued

| | | | | | |
|---|---|---|---|---|---|
| AGCGGCTCCG | ACGCCGCTAG | GGCGGAATTG | CGCACTGTTC | GATTCCGTCA | GGTTGTGGGC | 2940 |
| CTATCGTCCC | GCCCTCATGC | GGATCTACCT | GCCGACCCGG | AACGTGGACG | GACTCGGCCG | 3000 |
| CGCGATCTAT | GCCGAGTGCC | ACGCGCGAAA | CGCCGAATTT | CCGTGCAACG | ACGTGTGTCC | 3060 |
| CGGACCGCTA | CCGGACAGCG | AGGTCCGCGC | CATCGCCAAC | AGCATTTGGC | GTTGGATCAC | 3120 |
| AACCAAGTCG | CGCATTTGGG | CGGACGGGAT | CGTGGTCTAC | GAGGCCACAC | TCAGTGCGCG | 3180 |
| CCAGTCGGCC | ATCTCGCGGA | AGGGCGCAGC | AGCGCGCACG | GCGGCGAGCA | CAGTTGCGCG | 3240 |
| GCGCGCAAAG | TCCGCGTCAG | CCATGCATGG | AGGCATTGCT | ATGAGCGACG | GCTACAGCGA | 3300 |
| CGGCTACAGC | GACGGCTACA | ACCGGCAGCC | GACTGTCCGC | AAAAAGCGGC | GCGTGACCGC | 3360 |
| CGCCGAAGGC | GCTCGAATCA | CCGGACTATC | CGAACGCCAC | GTCGTCCGGC | TCGTGGCGCA | 3420 |
| GGAACGCAGC | GAGTGGCTCG | CCGAGCAGGC | TGCACGCCGC | GAACGCATCC | GCGCCTATCA | 3480 |
| CGACGACGAG | GGCCACTCTT | GGCCGCAAAC | GGCCAAACAT | TTCGGGCTGC | ATCTGGACAC | 3540 |
| CGTTAAGCGA | CTCGGCTATC | GGGCGAGGAA | AGAGCGTGCG | GCAGAACAGG | AAGCGGCTCA | 3600 |
| AAAGGCCCAC | AACGAAGCCG | ACAATCCACC | GCTGTTCTAA | CGCAATTGGG | GAGCGGGTGT | 3660 |
| CGCGGGGGTT | CCGTGGGGGG | TTCCGTTGCA | ACGGGTCGGA | CAGGTAAAAG | TCCTGGTAGA | 3720 |
| CGCTAGTTTT | CTGGTTTGGG | CCATGCCTGT | CTCGTTGCGT | GTTTCGTTGC | GCCCGTTTTG | 3780 |
| AATACCAGCC | AGACGAGACG | GGGTTCTACG | AATCTTGGTC | GATACCAAGC | CATTTCCGCT | 3840 |
| GAATATCGGG | GAGCTCACCG | CCAGAATCGG | TGGTTGTGGT | GATGTACGTG | GCGAACTCCG | 3900 |
| TTGTAGTGTT | GTGGTGGCAT | CCGTGGCGCG | GCCGCGGTAC | CAGATCTTTA | AATCTAGAGG | 3960 |
| TGACCACAAC | GACGCGCCCG | CTTTGATCGG | GGACGTCTGC | GGCCGACCAT | TTACGGGTCT | 4020 |
| TGTTGTCGTT | GGCGGTCATG | GGCCGAACAT | ACTCACCCGG | ATCGGAGGGC | CGAGGACAAG | 4080 |
| GTCGAACGAG | GGGCATGACC | CGGTGCGGGG | CTTCTTGCAC | TCGGCATAGG | CGAGTGCTAA | 4140 |
| GAATAACGTT | GGCACTCGCG | ACCGGTGAGT | CGTAGGTCGG | GACGGTGAGG | CCAGGCCCGT | 4200 |
| CGTCGCAGCG | AGTGGCAGCG | AGGACAACTT | GAGCCGTCCG | TCGCGGGCAC | TGCGCCCGGC | 4260 |
| CAGCGTAAGT | AGCGGGGTTG | CCGTCACCCG | GTGACCCCCG | GTTTCATCCC | CGATCCGGAG | 4320 |
| GAATCACTTC | GCAATGGCCA | AGACAATTGC | GGATCCAGCT | GCAGAATTCG | AAGCTTATCG | 4380 |
| ATGTCGACGT | AGTTAACTAG | CGTACGATCG | ACTGCCAGGC | ATCAAATAAA | ACGAAAGGCT | 4440 |
| CAGTCGAAAG | ACTGGGCCTT | TCGTTTTATC | TGTTGTTTGT | CCGGCCATCA | TGGCCGCGGT | 4500 |
| GATCA | | | | | | 4505 |

( 2 ) INFORMATION FOR SEQ ID NO:14:

( i ) SEQUENCE CHARACTERISTICS:
        ( A ) LENGTH: 3993 base pairs
        ( B ) TYPE: nucleic acid
        ( C ) STRANDEDNESS: single
        ( D ) TOPOLOGY: linear ( i i ) MOLECULE TYPE: DNA (plasmid)

( i x ) FEATURE:
        ( A ) NAME/KEY: misc_feature
        ( B ) LOCATION: 1..3993
        ( D ) OTHER INFORMATION: /standard_name= "plasmid pMV306"

( x i ) SEQUENCE DESCRIPTION: SEQ ID NO:14:

| | | | | | |
|---|---|---|---|---|---|
| GCTAGCCAAC | AAAGCGACGT | TGTGTCTCAA | AATCTCTGAT | GTTACATTGC | ACAAGATAAA | 60 |
| AATATATCAT | CATGAACAAT | AAAACTGTCT | GCTTACATAA | ACAGTAATAC | AAGGGGTGTT | 120 |
| ATGAGCCATA | TTCAACGGGA | AACGTCTTGC | TCGAGGCCGC | GATTAAATTC | CAACATGGAT | 180 |

```
GCTGATTTAT ATGGGTATAA ATGGGCTCGC GATAATGTCG GGCAATCAGG TGCGACAATC    240
TATCGCTTGT ATGGGAAGCC CCATGCGCCA GAGTTGTTTC TGAAACATGG CAAAGGTAGC    300
GTTGCCAATG ATGTTACAGA TGAGATGGTC AGACTAAACT GGCTGACGGA ATTTATGCCT    360
CTTCCGACCA TCAAGCATTT TATCCGTACT CCTGATGATG CATGGTTACT CACCACTGCG    420
ATCCCCGGGA AAACAGCATT CCAGGTATTA GAAGAATATC CTGATTCAGG TGAAAATATT    480
GTTGATGCGC TGGCAGTGTT CCTGCGCCGG TTGCATTCGA TTCCTGTTTG TAATTGTCCT    540
TTTAACAGCG ATCGCGTATT TCGTCTCGCT CAGGCGCAAT CACGAATGAA TAACGGTTTG    600
GTTGATGCGA GTGATTTTGA TGACGAGCGT AATGGCTGGC CTGTTGAACA AGTCTGGAAA    660
GAAATGCATA ATCTTTTGCC ATTCTCACCG GATTCAGTCG TCACTCATGG TGATTTCTCA    720
CTTGATAACC TTATTTTTGA CGAGGGGAAA TTAATAGGTT GTATTGATGT TGGACGAGTC    780
GGAATCGCAG ACCGATACCA GGATCTTGCC ATCCTATGGA ACTGCCTCGG TGAGTTTTCT    840
CCTTCATTAC AGAAACGGCT TTTTCAAAAA TATGGTATTG ATAATCCTGA TATGAATAAA    900
TTGCAGTTTC ATTTGATGCT CGATGAGTTT TTCTAATCAG AATTGGTTAA TTGGTTGTAA    960
CACTGGCAGA GCATTACGCT GACTTGACGG GACGGCGGCT TTGTTGAATA AATCGAACTT   1020
TTGCTGAGTT GAAGGATCAG ATCACGCATC TTCCCGACAA CGCAGACCGT TCCGTGGCAA   1080
AGCAAAAGTT CAAAATCACC AACTGGTCCA CCTACAACAA AGCTCTCATC AACCGTGGCT   1140
CCCTCACTTT CTGGCTGGAT GATGGGGCGA TTCAGGCCTG GTATGAGTCA GCAACACCTT   1200
CTTCACGAGG CAGACCTCAC TAGTTCCACT GAGCGTCAGA CCCCGTAGAA AAGATCAAAG   1260
GATCTTCTTG AGATCCTTTT TTTCTGCGCG TAATCTGCTG CTTGCAAACA AAAAAACCAC   1320
CGCTACCAGC GGTGGTTTGT TTGCCGGATC AAGAGCTACC AACTCTTTTT CCGAAGGTAA   1380
CTGGCTTCAG CAGAGCGCAG ATACCAAATA CTGTCCTTCT AGTGTAGCCG TAGTTAGGCC   1440
ACCACTTCAA GAACTCTGTA GCACCGCCTA CATACCTCGC TCTGCTAATC CTGTTACCAG   1500
TGGCTGCTGC CAGTGGCGAT AAGTCGTGTC TTACCGGGTT GGACTCAAGA CGATAGTTAC   1560
CGGATAAGGC GCAGCGGTCG GGCTGAACGG GGGGTTCGTG CACACAGCCC AGCTTGGAGC   1620
GAACGACCTA CACCGAACTG AGATACCTAC AGCGTGAGCA TTGAGAAAGC GCCACGCTTC   1680
CCGAAGGGAG AAAGGCGGAC AGGTATCCGG TAAGCGGCAG GGTCGGAACA GGAGAGCGCA   1740
CGAGGGAGCT TCCAGGGGGA AACGCCTGGT ATCTTTATAG TCCTGTCGGG TTTCGCCACC   1800
TCTGACTTGA GCGTCGATTT TGTGATGCT CGTCAGGGGG GCGGAGCCTA TGGAAAAACG   1860
CCAGCAACGC GGCCTTTTTA CGGTTCCTGG CCTTTTGCTG GCCTTTGCT CACATGTTCT   1920
TTCCTGCGTT ATCCCCTGAT TCTGTGGATA ACCGTATTAC CGCCTTTGAG TGAGCTGATA   1980
CCGCTCGCCG CAGCCGAACG ACCGAGCGCA ACGCGTGCGG CCGCGGTACC AGATCTTTAA   2040
ATCTAGATAT CCATGGATCC AGCTGCAGAA TTCGAAGCTT ATCGATGTCG ACGTAGTTAA   2100
CTAGCGTACG ATCGACTGCC AGGCATCAAA TAAAACGAAA GGCTCAGTCG AAAGACTGGG   2160
CCTTTCGTTT TATCTGTTGT TTGTCCGGCC ATCATGGCCG CGGTGATCAC TAGAGCCGTG   2220
AACGACAGGG CGAACGCCAG CCCGCCGACG GCGAGGGTTC CGACCGCTGC AACTCCCGGT   2280
GCAACCTTGT CCCGGTCTAT TCTCTTCACT GCACCAGCTC CAATCTGGTG TGAATGCCCC   2340
TCGTCTGTTC GCGCAGGCGG GGGGCTCTAT TCGTTTGTCA GCATCGAAAG TAGCCAGATC   2400
AGGGATGCGT TGCAACCGCG TATGCCCAGG TCAGAAGAGT CGCACAAGAG TTGCAGACCC   2460
CTGGAAAGAA AAATGGCCAG AGGGCGAAAA CACCCTCTGA CCAGCGGAGC GGGCGACGGG   2520
AATCGAACCC GCGTAGCTAG TTTGGAAGAA TGGGTGTCTG CCGACCACAT ATGGGCCGGT   2580
```

-continued

| | | | | | |
|---|---|---|---|---|---|
| CAAGATAGGT | TTTTACCCCC | TCTCGGCTGC | ATCCTCTAAG | TGGAAAGAAA | TTGCAGGTCG | 2640 |
| TAGAAGCGCG | TTGAAGCCTG | AGAGTTGCAC | AGGAGTTGCA | ACCCGGTAGC | CTTGTTCACG | 2700 |
| ACGAGAGGAG | ACCTAGTTGG | CACGTCGCGG | ATGGGGATCG | CTGAAGACTC | AGCGCAGCGG | 2760 |
| GAGGATCCAA | GCCTCATACG | TCAACCCGCA | GGACGGTGTG | AGGTACTACG | CGCTGCAGAC | 2820 |
| CTACGACAAC | AAGATGGACG | CCGAAGCCTG | GCTCGCGGGC | GAGAAGCGGC | TCATCGAGAT | 2880 |
| GGAGACCTGG | ACCCCTCCAC | AGGACCGGGC | GAAGAAGGCA | GCCGCCAGCG | CCATCACGCT | 2940 |
| GGAGGAGTAC | ACCCGGAAGT | GGCTCGTGGA | GCGCGACCTC | GCAGACGGCA | CCAGGGATCT | 3000 |
| GTACAGCGGG | CACGCGGAGC | GCCGCATCTA | CCCGGTGCTA | GGTGAAGTGG | CGGTCACAGA | 3060 |
| GATGACGCCA | GCTCTGGTGC | GTGCGTGGTG | GGCCGGGATG | GGTAGGAAGC | ACCCGACTGC | 3120 |
| CCGCCGGCAT | GCCTACAACG | TCCTCCGGGC | GGTGATGAAC | ACAGCGGTCG | AGGACAAGCT | 3180 |
| GATCGCAGAG | AACCCGTGCC | GGATCGAGCA | GAAGGCAGCC | GATGAGCGCG | ACGTAGAGGC | 3240 |
| GCTGACGCCT | GAGGAGCTGG | ACATCGTCGC | CGCTGAGATC | TTCGAGCACT | ACCGGATCGC | 3300 |
| GGCATACATC | CTGGCGTGGA | CGAGCCTCCG | GTTCGGAGAG | CTGATCGAGC | TTCGCCGCAA | 3360 |
| GGACATCGTG | GACGACGGCA | TGACGATGAA | GCTCCGGGTG | CGCCGTGGCG | CTTCCCGCGT | 3420 |
| GGGGAACAAG | ATCGTCGTTG | GCAACGCCAA | GACCGTCCGG | TCGAAGCGTC | CTGTGACGGT | 3480 |
| TCCGCCTCAC | GTCGCGGAGA | TGATCCGAGC | GCACATGAAG | GACCGTACGA | AGATGAACAA | 3540 |
| GGGCCCCGAG | GCATTCCTGG | TGACCACGAC | GCAGGGCAAC | CGGCTGTCGA | AGTCCGCGTT | 3600 |
| CACCAAGTCG | CTGAAGCGTG | GCTACGCCAA | GATCGGTCGG | CCGGAACTCC | GCATCCACGA | 3660 |
| CCTCCGCGCT | GTCGGCGCTA | CGTTCGCCGC | TCAGGCAGGT | GCGACGACCA | AGGAGCTGAT | 3720 |
| GGCCCGTCTC | GGTCACACGA | CTCCTAGGAT | GGCGATGAAG | TACCAGATGG | CGTCTGAGGC | 3780 |
| CCGCGACGAG | GCTATCGCTG | AGGCGATGTC | CAAGCTGGCC | AAGACCTCCT | GAAACGCAAA | 3840 |
| AAGCCCCCCT | CCCAAGGACA | CTGAGTCCTA | AGAGGGGGG | TTTCTTGTCA | GTACGCGAAG | 3900 |
| AACCACGCCT | GGCCGCGAGC | GCCAGCACCG | CCGCTCTGTG | CGGAGACCTG | GGCACCAGCC | 3960 |
| CCGCCGCCGC | CAGGAGCATT | GCCGTTCCCG | CCA | | | 3993 |

( 2 ) INFORMATION FOR SEQ ID NO:15:

( i ) SEQUENCE CHARACTERISTICS:
        ( A ) LENGTH: 4296 base pairs
        ( B ) TYPE: nucleic acid
        ( C ) STRANDEDNESS: single
        ( D ) TOPOLOGY: linear ( i i ) MOLECULE TYPE: DNA (plasmid)

( i x ) FEATURE:
        ( A ) NAME/KEY: misc_feature
        ( B ) LOCATION: 1..4296
        ( D ) OTHER INFORMATION: /standard_name= "plasmid pMH28"

( x i ) SEQUENCE DESCRIPTION: SEQ ID NO:15:

| | | | | | |
|---|---|---|---|---|---|
| GCTAGCCAAC | AAAGCGACGT | TGTGTCTCAA | AATCTCTGAT | GTTACATTGC | ACAAGATAAA | 60 |
| AATATATCAT | CATGAACAAT | AAAACTGTCT | GCTTACATAA | ACAGTAATAC | AAGGGGTGTT | 120 |
| ATGAGCCATA | TTCAACGGGA | AACGTCTTGC | TCGAGGCCGC | GATTAAATTC | CAACATGGAT | 180 |
| GCTGATTTAT | ATGGGTATAA | ATGGGCTCGC | GATAATGTCG | GGCAATCAGG | TGCGACAATC | 240 |
| TATCGCTTGT | ATGGGAAGCC | CCATGCGCCA | GAGTTGTTTC | TGAAACATGG | CAAAGGTAGC | 300 |
| GTTGCCAATG | ATGTTACAGA | TGAGATGGTC | AGACTAAACT | GGCTGACGGA | ATTTATGCCT | 360 |
| CTTCCGACCA | TCAAGCATTT | TATCCGTACT | CCTGATGATG | CATGGTTACT | CACCACTGCG | 420 |

| | | | | | | |
|---|---|---|---|---|---|---|
| ATCCCCGGGA | AAACAGCATT | CCAGGTATTA | GAAGAATATC | CTGATTCAGG | TGAAAATATT | 480 |
| GTTGATGCGC | TGGCAGTGTT | CCTGCGCCGG | TTGCATTCGA | TTCCTGTTTG | TAATTGTCCT | 540 |
| TTTAACAGCG | ATCGCGTATT | TCGTCTCGCT | CAGGCGCAAT | CACGAATGAA | TAACGGTTTG | 600 |
| GTTGATGCGA | GTGATTTTGA | TGACGAGCGT | AATGGCTGGC | CTGTTGAACA | AGTCTGGAAA | 660 |
| GAAATGCATA | ATCTTTTGCC | ATTCTCACCG | GATTCAGTCG | TCACTCATGG | TGATTTCTCA | 720 |
| CTTGATAACC | TTATTTTTGA | CGAGGGGAAA | TTAATAGGTT | GTATTGATGT | TGGACGAGTC | 780 |
| GGAATCGCAG | ACCGATACCA | GGATCTTGCC | ATCCTATGGA | ACTGCCTCGG | TGAGTTTTCT | 840 |
| CCTTCATTAC | AGAAACGGCT | TTTTCAAAAA | TATGGTATTG | ATAATCCTGA | TATGAATAAA | 900 |
| TTGCAGTTTC | ATTTGATGCT | CGATGAGTTT | TTCTAATCAG | AATTGGTTAA | TTGGTTGTAA | 960 |
| CACTGGCAGA | GCATTACGCT | GACTTGACGG | GACGGCGGCT | TTGTTGAATA | AATCGAACTT | 1020 |
| TTGCTGAGTT | GAAGGATCAG | ATCACGCATC | TTCCCGACAA | CGCAGACCGT | TCCGTGGCAA | 1080 |
| AGCAAAAGTT | CAAAATCACC | AACTGGTCCA | CCTACAACAA | AGCTCTCATC | AACCGTGGCT | 1140 |
| CCCTCACTTT | CTGGCTGGAT | GATGGGGCGA | TTCAGGCCTG | GTATGAGTCA | GCAACACCTT | 1200 |
| CTTCACGAGG | CAGACCTCAC | TAGTCAGCTG | CAGAATTCGA | AGCTTAATTA | ATCGATCTAG | 1260 |
| TTCCACTGAG | CGTCAGACCC | CGTAGAAAAG | ATCAAAGGAT | CTTCTTGAGA | TCCTTTTTTT | 1320 |
| CTGCGCGTAA | TCTGCTGCTT | GCAAACAAAA | AAACCACCGC | TACCAGCGGT | GGTTTGTTTG | 1380 |
| CCGGATCAAG | AGCTACCAAC | TCTTTTTCCG | AAGGTAACTG | GCTTCAGCAG | AGCGCAGATA | 1440 |
| CCAAATACTG | TCCTTCTAGT | GTAGCCGTAG | TTAGGCCACC | ACTTCAAGAA | CTCTGTAGCA | 1500 |
| CCGCCTACAT | ACCTCGCTCT | GCTAATCCTG | TTACCAGTGG | CTGCTGCCAG | TGGCGATAAG | 1560 |
| TCGTGTCTTA | CCGGGTTGGA | CTCAAGACGA | TAGTTACCGG | ATAAGGCGCA | GCGGTCGGGC | 1620 |
| TGAACGGGGG | GTTCGTGCAC | ACAGCCCAGC | TTGGAGCGAA | CGACCTACAC | CGAACTGAGA | 1680 |
| TACCTACAGC | GTGAGCATTG | AGAAAGCGCC | ACGCTTCCCG | AAGGGAGAAA | GGCGGACAGG | 1740 |
| TATCCGGTAA | GCGGCAGGGT | CGGAACAGGA | GAGCGCACGA | GGGAGCTTCC | AGGGGGAAAC | 1800 |
| GCCTGGTATC | TTTATAGTCC | TGTCGGGTTT | CGCCACCTCT | GACTTGAGCG | TCGATTTTTG | 1860 |
| TGATGCTCGT | CAGGGGGGCG | GAGCCTATGG | AAAAACGCCA | GCAACGCGGC | CTTTTTACGG | 1920 |
| TTCCTGGCCT | TTTGCTGGCC | TTTTGCTCAC | ATGTTCTTTC | CTGCGTTATC | CCCTGATTCT | 1980 |
| GTGGATAACC | GTATTACCGC | CTTTGAGTGA | GCTGATACCG | CTCGCCGCAG | CCGAACGACC | 2040 |
| GAGCGCAACG | CGTGAGCCCA | CCAGCTCCGT | AAGTTCGGGC | GCTGTGTGGC | TCGTACCCGC | 2100 |
| GCATTCAGGC | GGCAGGGGGT | CTAACGGGTC | TAAGGCGGCG | TGTACGGCCG | CCACAGCGGC | 2160 |
| TCTCAGCGGC | CCGGAAACGT | CCTCGAAACG | ACGCATGTGT | TCCTCCTGGT | TGGTACAGGT | 2220 |
| GGTTGGGGGT | GCTCGGCTGT | CGCTGGTGTT | CCACCACCAG | GGCTCGACGG | GAGAGCGGGG | 2280 |
| GAGTGTGCAG | TTGTGGGGTG | GCCCCTCAGC | GAAATATCTG | ACTTGGAGCT | CGTGTCGGAC | 2340 |
| CATACACCGG | TGATTAATCG | TGGTCTACTA | CCAAGCGTGA | GCCACGTCGC | CGACGAATTT | 2400 |
| GAGCAGCTCT | GGCTGCCGTA | CTGGCCGCTG | GCAAGCGACG | ATCTGCTCGA | GGGGATCTAC | 2460 |
| CGCCAAAGCC | GCGCGTCGGC | CCTAGGCCGC | CGGTACATCG | AGGCGAACCC | AACAGCGCTG | 2520 |
| GCAAACCTGC | TGGTCGTGGA | CGTAGACCAT | CCAGACGCAG | CGCTCCGAGC | GCTCAGCGCC | 2580 |
| CGGGGGTCCC | ATCCGCTGCC | CAACGCGATC | GTGGGCAATC | GCGCCAACGG | CCACGCACAC | 2640 |
| GCAGTGTGGG | CACTCAACGC | CCCTGTTCCA | CGCACCGAAT | ACGCGCGGCG | TAAGCCGCTC | 2700 |
| GCATACATGG | CGGCGTGCGC | CGAAGGCCTT | CGGCGCGCCG | TCGATGGCGA | CCGCAGTTAC | 2760 |
| TCAGGCCTCA | TGACCAAAAA | CCCCGGCCAC | ATCGCCTGGG | AAACGGAATG | GCTCCACTCA | 2820 |

| | | | | | |
|---|---|---|---|---|---|
| GATCTCTACA | CACTCAGCCA | CATCGAGGCC | GAGCTCGGCG | CGAACATGCC | ACCGCCGCGC | 2880 |
| TGGCGTCAGC | AGACCACGTA | CAAAGCGGCT | CCGACGCCGC | TAGGGCGGAA | TTGCGCACTG | 2940 |
| TTCGATTCCG | TCAGGTTGTG | GGCCTATCGT | CCCGCCCTCA | TGCGGATCTA | CCTGCCGACC | 3000 |
| CGGAACGTGG | ACGGACTCGG | CCGCGCGATC | TATGCCGAGT | GCCACGCGCG | AAACGCCGAA | 3060 |
| TTTCCGTGCA | ACGACGTGTG | TCCCGGACCG | CTACCGGACA | GCGAGGTCCG | CGCCATCGCC | 3120 |
| AACAGCATTT | GGCGTTGGAT | CACAACCAAG | TCGCGCATTT | GGGCGGACGG | GATCGTGGTC | 3180 |
| TACGAGGCCA | CACTCAGTGC | GCGCCAGTCG | GCCATCTCGC | GGAAGGGCGC | AGCAGCGCGC | 3240 |
| ACGGCGGCGA | GCACAGTTGC | GCGGCGCGCA | AAGTCCGCGT | CAGCCATGCA | TGGAGGCATT | 3300 |
| GCTATGAGCG | ACGGCTACAG | CGACGGCTAC | AGCGACGGCT | ACAACCGGCA | GCCGACTGTC | 3360 |
| CGCAAAAAGC | GGCGCGTGAC | CGCCGCCGAA | GGCGCTCGAA | TCACCGGACT | ATCCGAACGC | 3420 |
| CACGTCGTCC | GGCTCGTGGC | GCAGGAACGC | AGCGAGTGGC | TCGCCGAGCA | GGCTGCACGC | 3480 |
| CGCGAACGCA | TCCGCGCCTA | TCACGACGAC | GAGGGCCACT | CTTGGCCGCA | AACGGCCAAA | 3540 |
| CATTTCGGGC | TGCATCTGGA | CACCGTTAAG | CGACTCGGCT | ATCGGGCGAG | GAAAGAGCGT | 3600 |
| GCGGCAGAAC | AGGAAGCGGC | TCAAAAGGCC | CACAACGAAG | CCGACAATCC | ACCGCTGTTC | 3660 |
| TAACGCAATT | GGGGAGCGGG | TGTCGCGGGG | GTTCCGTGGG | GGGTTCCGTT | GCAACGGGTC | 3720 |
| GGACAGGTAA | AAGTCCTGGT | AGACGCTAGT | TTTCTGGTTT | GGGCCATGCC | TGTCTCGTTG | 3780 |
| CGTGTTTCGT | TGCGCCCGTT | TTGAATACCA | GCCAGACGAG | ACGGGGTTCT | ACGAATCTTG | 3840 |
| GTCGATACCA | AGCCATTTCC | GCTGAATATC | GGGGAGCTCA | CCGCCAGAAT | CGGTGGTTGT | 3900 |
| GGTGATGTAC | GTGGCGAACT | CCGTTGTAGT | GTTGTGGTGG | CATCCGTGGC | GCGGCCGCGG | 3960 |
| TACCGTTAAC | TACGTCGACA | TCGCTGGATC | CATGGATATC | TAGATATGAC | GACAGGAAGA | 4020 |
| GTTTGTAGAA | ACGCAAAAAG | GCCATCCGTC | AGGATGGCCT | TCTGCTTAAT | TTGATGCCTG | 4080 |
| GCAGTTTATG | GCGGGCGTCC | TGCCCGCCAC | CCTCCGGGCC | GTTGCTTCGC | AACGTTCAAA | 4140 |
| TCCGCTCCCG | GCGGATTTGT | CCTACTCAGG | AGAGCGTTCA | CCGACAAACA | ACAGATAAAA | 4200 |
| CGAAAGGCCC | AGTCTTTCGA | CTGAGCCTTT | CGTTTATTT | GATGCCTGGC | AGTTCCCTAC | 4260 |
| TCTCGCATGG | GGAGACCCCA | CACTACCATC | TGATCC | | | 4296 |

( 2 ) INFORMATION FOR SEQ ID NO:16:

( i ) SEQUENCE CHARACTERISTICS:
        ( A ) LENGTH: 4352 base pairs
        ( B ) TYPE: nucleic acid
        ( C ) STRANDEDNESS: single
        ( D ) TOPOLOGY: linear ( i i ) MOLECULE TYPE: DNA (plasmid)

( i x ) FEATURE:
        ( A ) NAME/KEY: misc_feature
        ( B ) LOCATION: 1..4352
        ( D ) OTHER INFORMATION: /standard_name= "plasmid pMH29"

( x i ) SEQUENCE DESCRIPTION: SEQ ID NO:16:

| | | | | | |
|---|---|---|---|---|---|
| GCTAGCCAAC | AAAGCGACGT | TGTGTCTCAA | AATCTCTGAT | GTTACATTGC | ACAAGATAAA | 60 |
| AATATATCAT | CATGAACAAT | AAAACTGTCT | GCTTACATAA | ACAGTAATAC | AAGGGGTGTT | 120 |
| ATGAGCCATA | TTCAACGGGA | AACGTCTTGC | TCGAGGCCGC | GATTAAATTC | CAACATGGAT | 180 |
| GCTGATTTAT | ATGGGTATAA | ATGGGCTCGC | GATAATGTCG | GGCAATCAGG | TGCGACAATC | 240 |
| TATCGCTTGT | ATGGGAAGCC | CCATGCGCCA | GAGTTGTTTC | TGAAACATGG | CAAAGGTAGC | 300 |
| GTTGCCAATG | ATGTTACAGA | TGAGATGGTC | AGACTAAACT | GGCTGACGGA | ATTTATGCCT | 360 |

```
CTTCCGACCA TCAAGCATTT TATCCGTACT CCTGATGATG CATGGTTACT CACCACTGCG    420
ATCCCCGGGA AAACAGCATT CCAGGTATTA GAAGAATATC CTGATTCAGG TGAAAATATT    480
GTTGATGCGC TGGCAGTGTT CCTGCGCCGG TTGCATTCGA TTCCTGTTTG TAATTGTCCT    540
TTTAACAGCG ATCGCGTATT TCGTCTCGCT CAGGCGCAAT CACGAATGAA TAACGGTTTG    600
GTTGATGCGA GTGATTTTGA TGACGAGCGT AATGGCTGGC CTGTTGAACA AGTCTGGAAA    660
GAAATGCATA ATCTTTTGCC ATTCTCACCG GATTCAGTCG TCACTCATGG TGATTTCTCA    720
CTTGATAACC TTATTTTTGA CGAGGGGAAA TTAATAGGTT GTATTGATGT TGGACGAGTC    780
GGAATCGCAG ACCGATACCA GGATCTTGCC ATCCTATGGA ACTGCCTCGG TGAGTTTTCT    840
CCTTCATTAC AGAAACGGCT TTTTCAAAAA TATGGTATTG ATAATCCTGA TATGAATAAA    900
TTGCAGTTTC ATTTGATGCT CGATGAGTTT TTCTAATCAG AATTGGTTAA TTGGTTGTAA    960
CACTGGCAGA GCATTACGCT GACTTGACGG GACGGCGGCT TTGTTGAATA AATCGAACTT   1020
TTGCTGAGTT GAAGGATCAG ATCACGCATC TTCCCGACAA CGCAGACCGT TCCGTGGCAA   1080
AGCAAAAGTT CAAAATCACC AACTGGTCCA CCTACAACAA AGCTCTCATC AACCGTGGCT   1140
CCCTCACTTT CTGGCTGGAT GATGGGGCGA TTCAGGCCTG GTATGAGTCA GCAACACCTT   1200
CTTCACGAGG CAGACCTCAC TAGTCAGCTG CAGAATTCGA AGCTTAATTA ATCGATCTAG   1260
TTCCACTGAG CGTCAGACCC CGTAGAAAAG ATCAAAGGAT CTTCTTGAGA TCCTTTTTTT   1320
CTGCGCGTAA TCTGCTGCTT GCAAACAAAA AAACCACCGC TACCAGCGGT GGTTTGTTTG   1380
CCGGATCAAG AGCTACCAAC TCTTTTTCCG AAGGTAACTG GCTTCAGCAG AGCGCAGATA   1440
CCAAATACTG TCCTTCTAGT GTAGCCGTAG TTAGGCCACC ACTTCAAGAA CTCTGTAGCA   1500
CCGCCTACAT ACCTCGCTCT GCTAATCCTG TTACCAGTGG CTGCTGCCAG TGGCGATAAG   1560
TCGTGTCTTA CCGGGTTGGA CTCAAGACGA TAGTTACCGG ATAAGGCGCA GCGGTCGGGC   1620
TGAACGGGGG GTTCGTGCAC ACAGCCCAGC TTGGAGCGAA CGACCTACAC CGAACTGAGA   1680
TACCTACAGC GTGAGCATTG AGAAAGCGCC ACGCTTCCCG AAGGGAGAAA GGCGGACAGG   1740
TATCCGGTAA GCGGCAGGGT CGGAACAGGA GAGCGCACGA GGGAGCTTCC AGGGGGAAAC   1800
GCCTGGTATC TTTATAGTCC TGTCGGGTTT CGCCACCTCT GACTTGAGCG TCGATTTTTG   1860
TGATGCTCGT CAGGGGGGCG GAGCCTATGG AAAAACGCCA GCAACGCGGC CTTTTTACGG   1920
TTCCTGGCCT TTTGCTGGCC TTTTGCTCAC ATGTTCTTTC CTGCGTTATC CCCTGATTCT   1980
GTGGATAACC GTATTACCGC CTTTGAGTGA GCTGATACCG CTCGCCGCAG CCGAACGACC   2040
GAGCGCAACG CGTGAGCCCA CCAGCTCCGT AAGTTCGGGC GCTGTGTGGC TCGTACCCGC   2100
GCATTCAGGC GGCAGGGGGT CTAACGGGTC TAAGGCGGCG TGTACGGCCG CCACAGCGGC   2160
TCTCAGCGGC CCGGAAACGT CCTCGAAACG ACGCATGTGT TCCTCCTGGT TGGTACAGGT   2220
GGTTGGGGGT GCTCGGCTGT CGCTGGTGTT CCACCACCAG GGCTCGACGG GAGAGCGGGG   2280
GAGTGTGCAG TTGTGGGGTG GCCCCTCAGC GAAATATCTG ACTTGGAGCT CGTGTCGGAC   2340
CATACACCGG TGATTAATCG TGGTCTACTA CCAAGCGTGA GCCACGTCGC CGACGAATTT   2400
GAGCAGCTCT GGCTGCCGTA CTGGCCGCTG GCAAGCGACG ATCTGCTCGA GGGGATCTAC   2460
CGCCAAAGCC GCGCGTCGGC CCTAGGCCGC CGGTACATCG AGGCGAACCC AACAGCGCTG   2520
GCAAACCTGC TGGTCGTGGA CGTAGACCAT CCAGACGCAG CGCTCCGAGC GCTCAGCGCC   2580
CGGGGGTCCC ATCCGCTGCC CAACGCGATC GTGGGCAATC GCGCCAACGG CCACGCACAC   2640
GCAGTGTGGG CACTCAACGC CCCTGTTCCA CGCACCGAAT ACGCGCGGCG TAAGCCGCTC   2700
GCATACATGG CGGCGTGCGC CGAAGGCCTT CGGCGCGCCG TCGATGGCGA CCGCAGTTAC   2760
```

| | | | | | |
|---|---|---|---|---|---|
| TCAGGCCTCA | TGACCAAAAA | CCCCGGCCAC | ATCGCCTGGG | AAACGGAATG | GCTCCACTCA | 2820 |
| GATCTCTACA | CACTCAGCCA | CATCGAGGCC | GAGCTCGGCG | CGAACATGCC | ACCGCCGCGC | 2880 |
| TGGCGTCAGC | AGACCACGTA | CAAAGCGGCT | CCGACGCCGC | TAGGGCGGAA | TTGCGCACTG | 2940 |
| TTCGATTCCG | TCAGGTTGTG | GGCCTATCGT | CCCGCCCTCA | TGCGGATCTA | CCTGCCGACC | 3000 |
| CGGAACGTGG | ACGGACTCGG | CCGCGCGATC | TATGCCGAGT | GCCACGCGCG | AAACGCCGAA | 3060 |
| TTTCCGTGCA | CGACGTGTG | TCCCGGACCG | CTACCGGACA | GCGAGGTCCG | CGCCATCGCC | 3120 |
| AACAGCATTT | GGCGTTGGAT | CACAACCAAG | TCGCGCATTT | GGGCGGACGG | GATCGTGGTC | 3180 |
| TACGAGGCCA | CACTCAGTGC | GCGCCAGTCG | GCCATCTCGC | GGAAGGGCGC | AGCAGCGCGC | 3240 |
| ACGGCGGCGA | GCACAGTTGC | GCGGCGCGCA | AAGTCCGCGT | CAGCCATGCA | TGGAGGCATT | 3300 |
| GCTATGAGCG | ACGGCTACAG | CGACGGCTAC | AGCGACGGCT | ACAACCGGCA | GCCGACTGTC | 3360 |
| CGCAAAAAGC | GGCGCGTGAC | CGCCGCCGAA | GGCGCTCGAA | TCACCGGACT | ATCCGAACGC | 3420 |
| CACGTCGTCC | GGCTCGTGGC | GCAGGAACGC | AGCGAGTGGC | TCGCCGAGCA | GGCTGCACGC | 3480 |
| CGCGAACGCA | TCCGCGCCTA | TCACGACGAC | GAGGGCCACT | CTTGGCCGCA | AACGGCCAAA | 3540 |
| CATTTCGGGC | TGCATCTGGA | CACCGTTAAG | CGACTCGGCT | ATCGGGCGAG | GAAAGAGCGT | 3600 |
| GCGGCAGAAC | AGGAAGCGGC | TCAAAAGGCC | CACAACGAAG | CCGACAATCC | ACCGCTGTTC | 3660 |
| TAACGCAATT | GGGGAGCGGG | TGTCGCGGGG | GTTCCGTGGG | GGGTTCCGTT | GCAACGGGTC | 3720 |
| GGACAGGTAA | AAGTCCTGGT | AGACGCTAGT | TTTCTGGTTT | GGGCCATGCC | TGTCTCGTTG | 3780 |
| CGTGTTTCGT | TGCGCCCGTT | TTGAATACCA | GCCAGACGAG | ACGGGGTTCT | ACGAATCTTG | 3840 |
| GTCGATACCA | AGCCATTTCC | GCTGAATATC | GGGGAGCTCA | CCGCCAGAAT | CGGTGGTTGT | 3900 |
| GGTGATGTAC | GTGGCGAACT | CCGTTGTAGT | GTTGTGGTGG | CATCCGTGGC | GCGGCCGCGG | 3960 |
| TACCGTTAAC | TACGTCGACA | TCGCTGGATC | CGAATTGTGA | GCGCTCACAA | TTCCACACAT | 4020 |
| TATACGAGCC | GGAAGCATAA | AGTGTCAAGC | CTGGTCTAGA | TATGACGACA | GGAAGAGTTT | 4080 |
| GTAGAAACGC | AAAAAGGCCA | TCCGTCAGGA | TGGCCTTCTG | CTTAATTTGA | TGCCTGGCAG | 4140 |
| TTTATGGCGG | GCGTCCTGCC | CGCCACCCTC | CGGGCCGTTG | CTTCGCAACG | TTCAAATCCG | 4200 |
| CTCCCGGCGG | ATTTGTCCTA | CTCAGGAGAG | CGTTCACCGA | CAAACAACAG | ATAAAACGAA | 4260 |
| AGGCCCAGTC | TTTCGACTGA | GCCTTTCGTT | TTATTTGATG | CCTGGCAGTT | CCCTACTCTC | 4320 |
| GCATGGGGAG | ACCCCACACT | ACCATCTGAT | CC | | | 4352 |

( 2 ) INFORMATION FOR SEQ ID NO:17:

( i ) SEQUENCE CHARACTERISTICS:
        ( A ) LENGTH: 6171 base pairs
        ( B ) TYPE: nucleic acid
        ( C ) STRANDEDNESS: single
        ( D ) TOPOLOGY: linear ( i i ) MOLECULE TYPE: DNA (plasmid)

( i x ) FEATURE:
        ( A ) NAME/KEY: misc_feature
        ( B ) LOCATION: 1..6171
        ( D ) OTHER INFORMATION: /standard_name= "plasmid
        pMV261- lux"

( x i ) SEQUENCE DESCRIPTION: SEQ ID NO:17:

| | | | | | |
|---|---|---|---|---|---|
| GCTAGCCAAC | AAAGCGACGT | TGTGTCTCAA | AATCTCTGAT | GTTACATTGC | ACAAGATAAA | 60 |
| AATATATCAT | CATGAACAAT | AAAACTGTCT | GCTTACATAA | ACAGTAATAC | AAGGGGTGTT | 120 |
| ATGAGCCATA | TTCAACGGGA | AACGTCTTGC | TCGAGGCCGC | GATTAAATTC | CAACATGGAT | 180 |
| GCTGATTTAT | ATGGGTATAA | ATGGGCTCGC | GATAATGTCG | GGCAATCAGG | TGCGACAATC | 240 |

```
TATCGCTTGT ATGGGAAGCC CCATGCGCCA GAGTTGTTTC TGAAACATGG CAAAGGTAGC      300
GTTGCCAATG ATGTTACAGA TGAGATGGTC AGACTAAACT GGCTGACGGA ATTTATGCCT      360
CTTCCGACCA TCAAGCATTT TATCCGTACT CCTGATGATG CATGGTTACT CACCACTGCG      420
ATCCCCGGGA AAACAGCATT CCAGGTATTA GAAGAATATC CTGATTCAGG TGAAAATATT      480
GTTGATGCGC TGGCAGTGTT CCTGCGCCGG TTGCATTCGA TTCCTGTTTG TAATTGTCCT      540
TTTAACAGCG ATCGCGTATT TCGTCTCGCT CAGGCGCAAT CACGAATGAA TAACGGTTTG      600
GTTGATGCGA GTGATTTTGA TGACGAGCGT AATGGCTGGC CTGTTGAACA AGTCTGGAAA      660
GAAATGCATA ATCTTTTGCC ATTCTCACCG GATTCAGTCG TCACTCATGG TGATTTCTCA      720
CTTGATAACC TTATTTTTGA CGAGGGGAAA TTAATAGGTT GTATTGATGT TGGACGAGTC      780
GGAATCGCAG ACCGATACCA GGATCTTGCC ATCCTATGGA ACTGCCTCGG TGAGTTTTCT      840
CCTTCATTAC AGAAACGGCT TTTTCAAAAA TATGGTATTG ATAATCCTGA TATGAATAAA      900
TTGCAGTTTC ATTTGATGCT CGATGAGTTT TTCTAATCAG AATTGGTTAA TTGGTTGTAA      960
CACTGGCAGA GCATTACGCT GACTTGACGG GACGGCGGCT TTGTTGAATA AATCGAACTT     1020
TTGCTGAGTT GAAGGATCAG ATCACGCATC TTCCCGACAA CGCAGACCGT TCCGTGGCAA     1080
AGCAAAAGTT CAAAATCACC AACTGGTCCA CCTACAACAA AGCTCTCATC AACCGTGGCT     1140
CCCTCACTTT CTGGCTGGAT GATGGGGCGA TTCAGGCCTG GTATGAGTCA GCAACACCTT     1200
CTTCACGAGG CAGACCTCAC TAGTTCCACT GAGCGTCAGA CCCCGTAGAA AAGATCAAAG     1260
GATCTTCTTG AGATCCTTTT TTTCTGCGCG TAATCTGCTG CTTGCAAACA AAAAAACCAC     1320
CGCTACCAGC GGTGGTTTGT TTGCCGGATC AAGAGCTACC AACTCTTTTT CCGAAGGTAA     1380
CTGGCTTCAG CAGAGCGCAG ATACCAAATA CTGTCCTTCT AGTGTAGCCG TAGTTAGGCC     1440
ACCACTTCAA GAACTCTGTA GCACCGCCTA CATACCTCGC TCTGCTAATC CTGTTACCAG     1500
TGGCTGCTGC CAGTGGCGAT AAGTCGTGTC TTACCGGGTT GGACTCAAGA CGATAGTTAC     1560
CGGATAAGGC GCAGCGGTCG GGCTGAACGG GGGGTTCGTG CACACAGCCC AGCTTGGAGC     1620
GAACGACCTA CACCGAACTG AGATACCTAC AGCGTGAGCA TTGAGAAAGC GCCACGCTTC     1680
CCGAAGGGAG AAAGGCGGAC AGGTATCCGG TAAGCGGCAG GGTCGGAACA GGAGAGCGCA     1740
CGAGGGAGCT TCCAGGGGGA AACGCCTGGT ATCTTTATAG TCCTGTCGGG TTTCGCCACC     1800
TCTGACTTGA GCGTCGATTT TTGTGATGCT CGTCAGGGGG CGGAGCCTA TGGAAAAACG     1860
CCAGCAACGC GGCCTTTTTA CGGTTCCTGG CCTTTTGCTG GCCTTTGCT CACATGTTCT      1920
TTCCTGCGTT ATCCCCTGAT TCTGTGGATA ACCGTATTAC CGCCTTTGAG TGAGCTGATA     1980
CCGCTCGCCG CAGCCGAACG ACCGAGCGCA ACGCGTGCGG CCGCACGCGT GAGCCCACCA     2040
GCTCCGTAAG TTCGGGCGCT GTGTGGCTCG TACCCGCGCA TTCAGGCGGC AGGGGGTCTA     2100
ACGGGTCTAA GGCGGCGTGT ACGGCCGCCA CAGCGGCTCT CAGCGGCCCG GAAACGTCCT     2160
CGAAACGACG CATGTGTTCC TCCTGGTTGG TACAGGTGGT TGGGGTGCT CGGCTGTCGC      2220
TGGTGTTCCA CCACCAGGGC TCGACGGGAG AGCGGGGGAG TGTGCAGTTG TGGGGTGGCC     2280
CCTCAGCGAA ATATCTGACT TGGAGCTCGT GTCGGACCAT ACACCGGTGA TTAATCGTGG     2340
TCTACTACCA AGCGTGAGCC ACGTCGCCGA CGAATTTGAG CAGCTCTGGC TGCCGTACTG     2400
GCCGCTGGCA AGCGACGATC TGCTCGAGGG GATCTACCGC CAAAGCCGCG CGTCGGCCCT     2460
AGGCCGCCGG TACATCGAGG CGAACCCAAC AGCGCTGGCA AACCTGCTGG TCGTGGACGT     2520
AGACCATCCA GACGCAGCGC TCCGAGCGCT CAGCGCCCGG GGTCCCATC CGCTGCCCAA      2580
CGCGATCGTG GGCAATCGCG CCAACGGCCA CGCACACGCA GTGTGGGCAC TCAACGCCCC     2640
```

```
TGTTCCACGC ACCGAATACG CGCGGCGTAA GCCGCTCGCA TACATGGCGG CGTGCGCCGA   2700
AGGCCTTCGG CGCGCCGTCG ATGGCGACCG CAGTTACTCA GGCCTCATGA CCAAAAACCC   2760
CGGCCACATC GCCTGGGAAA CGGAATGGCT CCACTCAGAT CTCTACACAC TCAGCCACAT   2820
CGAGGCCGAG CTCGGCGCGA ACATGCCACC GCCGCGCTGG CGTCAGCAGA CCACGTACAA   2880
AGCGGCTCCG ACGCCGCTAG GGCGGAATTG CGCACTGTTC GATTCCGTCA GGTTGTGGGC   2940
CTATCGTCCC GCCCTCATGC GGATCTACCT GCCGACCCGG AACGTGGACG GACTCGGCCG   3000
CGCGATCTAT GCCGAGTGCC ACGCGCGAAA CGCCGAATTT CCGTGCAACG ACGTGTGTCC   3060
CGGACCGCTA CCGGACAGCG AGGTCCGCGC CATCGCCAAC AGCATTTGGC GTTGGATCAC   3120
AACCAAGTCG CGCATTTGGG CGGACGGGAT CGTGGTCTAC GAGGCCACAC TCAGTGCGCG   3180
CCAGTCGGCC ATCTCGCGGA AGGGCGCAGC AGCGCGCACG GCGGCGAGCA CAGTTGCGCG   3240
GCGCGCAAAG TCCGCGTCAG CCATGCATGG AGGCATTGCT ATGAGCGACG GCTACAGCGA   3300
CGGCTACAGC GACGGCTACA ACCGGCAGCC GACTGTCCGC AAAAAGCGGC GCGTGACCGC   3360
CGCCGAAGGC GCTCGAATCA CCGGACTATC CGAACGCCAC GTCGTCCGGC TCGTGGCGCA   3420
GGAACGCAGC GAGTGGCTCG CCGAGCAGGC TGCACGCCGC GAACGCATCC GCGCCTATCA   3480
CGACGACGAG GGCCACTCTT GGCCGCAAAC GGCCAAACAT TTCGGGCTGC ATCTGGACAC   3540
CGTTAAGCGA CTCGGCTATC GGGCGAGGAA AGAGCGTGCG GCAGAACAGG AAGCGGCTCA   3600
AAAGGCCCAC AACGAAGCCG ACAATCCACC GCTGTTCTAA CGCAATTGGG GAGCGGGTGT   3660
CGCGGGGGTT CCGTGGGGGG TTCCGTTGCA ACGGGTCGGA CAGGTAAAAG TCCTGGTAGA   3720
CGCTAGTTTT CTGGTTTGGG CCATGCCTGT CTCGTTGCGT GTTCGTTGC GCCCGTTTTG    3780
AATACCAGCC AGACGAGACG GGGTTCTACG AATCTTGGTC GATACCAAGC CATTTCCGCT   3840
GAATATCGGG GAGCTCACCG CCAGAATCGG TGGTTGTGGT GATGTACGTG GCGAACTCCG   3900
TTGTAGTGTT GTGGTGGCAT CCGTGGCGCG CCGCGGTAC CAGATCTTTA AATCTAGAGG    3960
TGACCACAAC GACGCGCCCG CTTTGATCGG GGACGTCTGC GGCCGACCAT TTACGGGTCT   4020
TGTTGTCGTT GGCGGTCATG GGCCGAACAT ACTCACCCGG ATCGGAGGGC CGAGGACAAG   4080
GTCGAACGAG GGGCATGACC CGGTGCGGGG CTTCTTGCAC TCGGCATAGG CGAGTGCTAA   4140
GAATAACGTT GGCACTCGCG ACCGGTGAGT CGTAGGTCGG GACGGTGAGG CCAGGCCCGT   4200
CGTCGCAGCG AGTGGCAGCG AGGACAACTT GAGCCGTCCG TCGCGGGCAC TGCGCCCGGC   4260
CAGCGTAAGT AGCGGGGTTG CCGTCACCCG GTGACCCCCG GTTTCATCCC CGATCCGGAG   4320
GAATCACTTC GCAATGGCCA AGACAATTGC GGATCCAGGA GGAATCACTC AATGGAAGAC   4380
GCCAAAAACA TCAAGAAAGG CCCGGCGCCA TTCTATCCTC TAGAGGATGG AACCGCTGGA   4440
GAGCAACTGC ATAAGGCTAT GAAGAGATAC GCCCTGGTTC CTGGAACAAT GCTTTTACA    4500
GATGCACATA TCGAGGTGAA CATCACGTAC GCGGAATACT TCGAAATGTC CGTTCGGTTG   4560
GCAGAAGCTA TGAAACGATA TGGGCTGAAT ACAAATCACA GAATCGTCGT ATGCAGTGAA   4620
AACTCTCTTC AATTCTTTAT GCCGGTGTTG GGCGCGTTAT TTATCGGAGT TGCAGTTGCG   4680
CCCGCGAACG ACATTTATAA TGAACGTGAA TTGCTCAACA GTATGAACAT TTCGCAGCCT   4740
ACCGTAGTGT TTGTTTCCAA AAAGGGGTTG CAAAAAATTT TGAACGTGCA AAAAAAATTA   4800
CCAATAATCC AGAAAATTAT TATCATGGAT TCTAAAACGG ATTACCAGGG ATTTCAGTCG   4860
ATGTACACGT TCGTCACATC TCATCTACCT CCCGGTTTTA ATGAATACGA TTTTGTACCA   4920
GAGTCCTTTG ATCGTGACAA AACAATTGCA CTGATAATGA ATTCCTCTGG ATCTACTGGG   4980
TTACCTAAGG GTGTGGCCCT TCCGCATAGA ACTGCCTGCG TCAGATTCTC GCATGCCAGA   5040
```

-continued

| | | | | | | |
|---|---|---|---|---|---|---|
| GATCCTATTT | TTGGCAATCA | AATCATTCCG | GATACTGCGA | TTTTAAGTGT | TGTTCCATTC | 5100 |
| CATCACGGTT | TTGGAATGTT | TACTACACTC | GGATATTTGA | TATGTGGATT | TCGAGTCGTC | 5160 |
| TTAATGTATA | GATTTGAAGA | AGAGCTGTTT | TTACGATCCC | TTCAGGATTA | CAAAATTCAA | 5220 |
| AGTGCGTTGC | TAGTACCAAC | CCTATTTTCA | TTCTTCGCCA | AAAGCACTCT | GATTGACAAA | 5280 |
| TACGATTTAT | CTAATTTACA | CGAAATTGCT | TCTGGGGGCG | CACCTCTTTC | GAAAGAAGTC | 5340 |
| GGGGAAGCGG | TTGCAAAACG | CTTCCATCTT | CCAGGGATAC | GACAAGGATA | TGGGCTCACT | 5400 |
| GAGACTACAT | CAGCTATTCT | GATTACACCC | GAGGGGGATG | ATAAACCGGG | CGCGGTCGGT | 5460 |
| AAAGTTGTTC | CATTTTTTGA | AGCGAAGGTT | GTGGATCTGG | ATACCGGGAA | AACGCTGGGC | 5520 |
| GTTAATCAGA | GAGGCGAATT | ATGTGTCAGA | GGACCTATGA | TTATGTCCGG | TTATGTAAAC | 5580 |
| AATCCGGAAG | CGACCAACGC | CTTGATTGAC | AAGGATGGAT | GGCTACATTC | TGGAGACATA | 5640 |
| GCTTACTGGG | ACGAAGACGA | ACACTTCTTC | ATAGTTGACC | GCTTGAAGTC | TTTAATTAAA | 5700 |
| TACAAAGGAT | ATCAGGTGGC | CCCCGCTGAA | TTGGAATCGA | TATTGTTACA | ACACCCCAAC | 5760 |
| ATCTTCGACG | CGGGCGTGGC | AGGTCTTCCC | GACGATGACG | CCGGTGAACT | TCCCGCCGCC | 5820 |
| GTTGTTGTTT | TGGAGCACGG | AAAGACGATG | ACGGAAAAAG | AGATCGTGGA | TTACGTCGCC | 5880 |
| AGTCAAGTAA | CAACCGCGAA | AAAGTTGCGC | GGAGGAGTTG | TGTTTGTGGA | CGAAGTACCG | 5940 |
| AAAGGTCTTA | CCGGAAAACT | CGACGCAAGA | AAAATCAGAG | AGATCCTCAT | AAAGGCCAAG | 6000 |
| AAGGGCGGAA | AGTCCAAATT | GTAAAATGTA | ACTGTATTCA | GCGATGACGT | CGACGTAGTT | 6060 |
| AACTAGCGTA | CGATCGACTG | CCAGGCATCA | AATAAAACGA | AAGGCTCAGT | CGAAAGACTG | 6120 |
| GGCCTTTCGT | TTATCTGTT | GTTTGTCCGG | CCATCATGGC | CGCGGTGATC | A | 6171 |

( 2 ) INFORMATION FOR SEQ ID NO:18:

( i ) SEQUENCE CHARACTERISTICS:
        ( A ) LENGTH: 6044 base pairs
        ( B ) TYPE: nucleic acid
        ( C ) STRANDEDNESS: single
        ( D ) TOPOLOGY: linear ( i i ) MOLECULE TYPE: DNA (plasmid)

( i x ) FEATURE:
        ( A ) NAME/KEY: misc_feature
        ( B ) LOCATION: 1..6044
        ( D ) OTHER INFORMATION: /standard_name= "plasmid
        pMV361- lux"

( x i ) SEQUENCE DESCRIPTION: SEQ ID NO:18:

| | | | | | | |
|---|---|---|---|---|---|---|
| GCTAGCCAAC | AAAGCGACGT | TGTGTCTCAA | AATCTCTGAT | GTTACATTGC | ACAAGATAAA | 60 |
| AATATATCAT | CATGAACAAT | AAAACTGTCT | GCTTACATAA | ACAGTAATAC | AAGGGGTGTT | 120 |
| ATGAGCCATA | TTCAACGGGA | AACGTCTTGC | TCGAGGCCGC | GATTAAATTC | CAACATGGAT | 180 |
| GCTGATTTAT | ATGGGTATAA | ATGGGCTCGC | GATAATGTCG | GCAATCAGG | TGCGACAATC | 240 |
| TATCGCTTGT | ATGGGAAGCC | CCATGCGCCA | GAGTTGTTTC | TGAAACATGG | CAAAGGTAGC | 300 |
| GTTGCCAATG | ATGTTACAGA | TGAGATGGTC | AGACTAAACT | GGCTGACGGA | ATTTATGCCT | 360 |
| CTTCCGACCA | TCAAGCATTT | TATCCGTACT | CCTGATGATG | CATGGTTACT | CACCACTGCG | 420 |
| ATCCCCGGGA | AAACAGCATT | CCAGGTATTA | GAAGAATATC | CTGATTCAGG | TGAAAATATT | 480 |
| GTTGATGCGC | TGGCAGTGTT | CCTGCGCCGG | TTGCATTCGA | TTCCTGTTTG | TAATTGTCCT | 540 |
| TTTAACAGCG | ATCGCGTATT | TCGTCTCGCT | CAGGCGCAAT | CACGAATGAA | TAACGGTTTG | 600 |
| GTTGATGCGA | GTGATTTTGA | TGACGAGCGT | AATGGCTGGC | CTGTTGAACA | AGTCTGGAAA | 660 |

```
GAAATGCATA ATCTTTTGCC ATTCTCACCG GATTCAGTCG TCACTCATGG TGATTTCTCA    720
CTTGATAACC TTATTTTTGA CGAGGGGAAA TTAATAGGTT GTATTGATGT TGGACGAGTC    780
GGAATCGCAG ACCGATACCA GGATCTTGCC ATCCTATGGA ACTGCCTCGG TGAGTTTTCT    840
CCTTCATTAC AGAAACGGCT TTTTCAAAAA TATGGTATTG ATAATCCTGA TATGAATAAA    900
TTGCAGTTTC ATTTGATGCT CGATGAGTTT TTCTAATCAG AATTGGTTAA TTGGTTGTAA    960
CACTGGCAGA GCATTACGCT GACTTGACGG GACGGCGGCT TGTTGAATA AATCGAACTT    1020
TTGCTGAGTT GAAGGATCAG ATCACGCATC TTCCCGACAA CGCAGACCGT TCCGTGGCAA    1080
AGCAAAAGTT CAAAATCACC AACTGGTCCA CCTACAACAA AGCTCTCATC AACCGTGGCT    1140
CCCTCACTTT CTGGCTGGAT GATGGGCGA TTCAGGCCTG GTATGAGTCA GCAACACCTT    1200
CTTCACGAGG CAGACCTCAC TAGTTCCACT GAGCGTCAGA CCCCGTAGAA AAGATCAAAG    1260
GATCTTCTTG AGATCCTTTT TTTCTGCGCG TAATCTGCTG CTTGCAAACA AAAAAACCAC    1320
CGCTACCAGC GGTGGTTTGT TGCCGGATC AAGAGCTACC AACTCTTTTT CCGAAGGTAA    1380
CTGGCTTCAG CAGAGCGCAG ATACCAAATA CTGTCCTTCT AGTGTAGCCG TAGTTAGGCC    1440
ACCACTTCAA GAACTCTGTA GCACCGCCTA CATACCTCGC TCTGCTAATC CTGTTACCAG    1500
TGGCTGCTGC CAGTGGCGAT AAGTCGTGTC TTACCGGGTT GGACTCAAGA CGATAGTTAC    1560
CGGATAAGGC GCAGCGGTCG GGCTGAACGG GGGGTTCGTG CACACAGCCC AGCTTGGAGC    1620
GAACGACCTA CACCGAACTG AGATACCTAC AGCGTGAGCA TTGAGAAAGC GCCACGCTTC    1680
CCGAAGGGAG AAAGGCGGAC AGGTATCCGG TAAGCGGCAG GGTCGGAACA GGAGAGCGCA    1740
CGAGGGAGCT TCCAGGGGGA AACGCCTGGT ATCTTTATAG TCCTGTCGGG TTTCGCCACC    1800
TCTGACTTGA GCGTCGATTT TTGTGATGCT CGTCAGGGGG GCGGAGCCTA TGGAAAAACG    1860
CCAGCAACGC GGCCTTTTTA CGGTTCCTGG CCTTTTGCTG GCCTTTGCT CACATGTTCT    1920
TTCCTGCGTT ATCCCCTGAT TCTGTGGATA ACCGTATTAC CGCCTTTGAG TGAGCTGATA    1980
CCGCTCGCCG CAGCCGAACG ACCGAGCGCA ACGCGTGCGG CCGCGGTACC AGATCTTTAA    2040
ATCTAGAGGT GACCACAACG ACGCGCCCGC TTTGATCGGG GACGTCTGCG GCCGACCATT    2100
TACGGGTCTT GTTGTCGTTG GCGGTCATGG GCCGAACATA CTCACCCGGA TCGGAGGGCC    2160
GAGGACAAGG TCGAACGAGG GGCATGACCC GGTGCGGGGC TTCTTGCACT CGGCATAGGC    2220
GAGTGCTAAG AATAACGTTG GCACTCGCGA CCGGTGAGTC GTAGGTCGGG ACGGTGAGGC    2280
CAGGCCCGTC GTCGCAGCGA GTGGCAGCGA GGACAACTTG AGCCGTCCGT CGCGGGCACT    2340
GCGCCGGCC AGCGTAAGTA GCGGGGTTGC CGTCACCCGG TGACCCCGG TTTCATCCCC    2400
GATCCGGAGG AATCACTTCG CAATGGCCAA GACAATTGCG GATCCAGGAG GAATCACTCA    2460
ATGGAAGACG CCAAAAACAT CAAGAAAGGC CCGGCGCCAT TCTATCCTCT AGAGGATGGA    2520
ACCGCTGGAG AGCAACTGCA TAAGGCTATG AAGAGATACG CCCTGGTTCC TGGAACAATT    2580
GCTTTTACAG ATGCACATAT CGAGGTGAAC ATCACGTACG CGGAATACTT CGAAATGTCC    2640
GTTCGGTTGG CAGAAGCTAT GAAACGATAT GGGCTGAATA CAAATCACAG AATCGTCGTA    2700
TGCAGTGAAA ACTCTCTTCA ATTCTTTATG CCGGTGTTGG GCGCGTTATT TATCGGAGTT    2760
GCAGTTGCGC CCGCGAACGA CATTTATAAT GAACGTGAAT TGCTCAACAG TATGAACATT    2820
TCGCAGCCTA CCGTAGTGTT TGTTTCCAAA AAGGGGTTGC AAAAAATTTT GAACGTGCAA    2880
AAAAAATTAC CAATAATCCA GAAAATTATT ATCATGGATT CTAAAACGGA TTACCAGGGA    2940
TTTCAGTCGA TGTACACGTT CGTCACATCT CATCTACCTC CCGGTTTTAA TGAATACGAT    3000
TTTGTACCAG AGTCCTTTGA TCGTGACAAA ACAATTGCAC TGATAATGAA TTCCTCTGGA    3060
```

```
TCTACTGGGT TACCTAAGGG TGTGGCCCTT CCGCATAGAA CTGCCTGCGT CAGATTCTCG    3120
CATGCCAGAG ATCCTATTTT TGGCAATCAA ATCATTCCGG ATACTGCGAT TTTAAGTGTT    3180
GTTCCATTCC ATCACGGTTT TGGAATGTTT ACTACACTCG GATATTTGAT ATGTGGATTT    3240
CGAGTCGTCT TAATGTATAG ATTTGAAGAA GAGCTGTTTT TACGATCCCT TCAGGATTAC    3300
AAAATTCAAA GTGCGTTGCT AGTACCAACC CTATTTTCAT TCTTCGCCAA AAGCACTCTG    3360
ATTGACAAAT ACGATTTATC TAATTTACAC GAAATTGCTT CTGGGGGCGC ACCTCTTTCG    3420
AAAGAAGTCG GGGAAGCGGT TGCAAAACGC TTCCATCTTC CAGGGATACG ACAAGGATAT    3480
GGGCTCACTG AGACTACATC AGCTATTCTG ATTACACCCG AGGGGGATGA TAAACCGGGC    3540
GCGGTCGGTA AAGTTGTTCC ATTTTTTGAA GCGAAGGTTG TGGATCTGGA TACCGGGAAA    3600
ACGCTGGGCG TTAATCAGAG AGGCGAATTA TGTGTCAGAG GACCTATGAT TATGTCCGGT    3660
TATGTAAACA ATCCGGAAGC GACCAACGCC TTGATTGACA AGGATGGATG GCTACATTCT    3720
GGAGACATAG CTTACTGGGA CGAAGACGAA CACTTCTTCA TAGTTGACCG CTTGAAGTCT    3780
TTAATTAAAT ACAAAGGATA TCAGGTGGCC CCCGCTGAAT TGGAATCGAT ATTGTTACAA    3840
CACCCCAACA TCTTCGACGC GGGCGTGGCA GGTCTTCCCG ACGATGACGC CGGTGAACTT    3900
CCCGCCGCCG TTGTTGTTTT GGAGCACGGA AAGACGATGA CGGAAAAAGA GATCGTGGAT    3960
TACGTCGCCA GTCAAGTAAC AACCGCGAAA AAGTTGCGCG GAGGAGTTGT GTTTGTGGAC    4020
GAAGTACCGA AAGGTCTTAC CGGAAAACTC GACGCAAGAA AAATCAGAGA GATCCTCATA    4080
AAGGCCAAGA AGGGCGGAAA GTCCAAATTG TAAAATGTAA CTGTATTCAG CGATGACGTC    4140
GACGTAGTTA ACTAGCGTAC GATCGACTGC CAGGCATCAA ATAAAACGAA AGGCTCAGTC    4200
GAAAGACTGG GCCTTTCGTT TTATCTGTTG TTTGTCCGGC CATCATGGCC GCGGTGATCA    4260
CTAGAGCCGT GAACGACAGG GCGAACGCCA GCCCGCCGAC GGCGAGGGTT CCGACCGCTG    4320
CAACTCCCGG TGCAACCTTG TCCCGGTCTA TTCTCTTCAC TGCACCAGCT CCAATCTGGT    4380
GTGAATGCCC CTCGTCTGTT CGCGCAGGCG GGGGGCTCTA TTCGTTTGTC AGCATCGAAA    4440
GTAGCCAGAT CAGGGATGCG TTGCAACCGC GTATGCCCAG GTCAGAAGAG TCGCACAAGA    4500
GTTGCAGACC CCTGGAAAGA AAAATGGCCA GAGGGCGAAA ACACCCTCTG ACCAGCGGAG    4560
CGGGCGACGG GAATCGAACC CGCGTAGCTA GTTTGGAAGA ATGGGTGTCT GCCGACCACA    4620
TATGGGCCGG TCAAGATAGG TTTTTACCCC CTCTCGGCTG CATCCTCTAA GTGGAAAGAA    4680
ATTGCAGGTC GTAGAAGCGC GTTGAAGCCT GAGAGTTGCA CAGGAGTTGC AACCCGGTAG    4740
CCTTGTTCAC GACGAGAGGA GACCTAGTTG GCACGTCGCG GATGGGGATC GCTGAAGACT    4800
CAGCGCAGCG GGAGGATCCA AGCCTCATAC GTCAACCCGC AGGACGGTGT GAGGTACTAC    4860
GCGCTGCAGA CCTACGACAA CAAGATGGAC GCCGAAGCCT GGCTCGCGGG CGAGAAGCGG    4920
CTCATCGAGA TGGAGACCTG GACCCCTCCA CAGGACCGGG CGAAGAAGGC AGCCGCCAGC    4980
GCCATCACGC TGGAGGAGTA CACCCGGAAG TGGCTCGTGG AGCGCGACCT CGCAGACGGC    5040
ACCAGGGATC TGTACAGCGG GCACGCGGAG CGCCGCATCT ACCCGGTGCT AGGTGAAGTG    5100
GCGGTCACAG AGATGACGCC AGCTCTGGTG CGTGCGTGGT GGGCCGGGAT GGGTAGGAAG    5160
CACCCGACTG CCCGCCGGCA TGCCTACAAC GTCCTCCGGG CGGTGATGAA CACAGCGGTC    5220
GAGGACAAGC TGATCGCAGA GAACCCGTGC CGGATCGAGC AGAAGGCAGC CGATGAGCGC    5280
GACGTAGAGG CGCTGACGCC TGAGGAGCTG GACATCGTCG CCGCTGAGAT CTTCGAGCAC    5340
TACCGGATCG CGGCATACAT CCTGGCGTGG ACGAGCCTCC GGTTCGGAGA GCTGATCGAG    5400
CTTCGCCGCA AGGACATCGT GGACGACGGC ATGACGATGA AGCTCCGGGT GCGCCGTGGC    5460
```

-continued

| | | | | | | |
|---|---|---|---|---|---|---|
| GCTTCCCGCG | TGGGGAACAA | GATCGTCGTT | GGCAACGCCA | AGACCGTCCG | GTCGAAGCGT | 5520 |
| CCTGTGACGG | TTCCGCCTCA | CGTCGCGGAG | ATGATCCGAG | CGCACATGAA | GGACCGTACG | 5580 |
| AAGATGAACA | AGGGCCCCGA | GGCATTCCTG | GTGACCACGA | CGCAGGGCAA | CCGGCTGTCG | 5640 |
| AAGTCCGCGT | TCACCAAGTC | GCTGAAGCGT | GGCTACGCCA | AGATCGGTCG | GCCGGAACTC | 5700 |
| CGCATCCACG | ACCTCCGCGC | TGTCGGCGCT | ACGTTCGCCG | CTCAGGCAGG | TGCGACGACC | 5760 |
| AAGGAGCTGA | TGGCCCGTCT | CGGTCACACG | ACTCCTAGGA | TGGCGATGAA | GTACCAGATG | 5820 |
| GCGTCTGAGG | CCCGCGACGA | GGCTATCGCT | GAGGCGATGT | CCAAGCTGGC | CAAGACCTCC | 5880 |
| TGAAACGCAA | AAAGCCCCCC | TCCCAAGGAC | ACTGAGTCCT | AAAGAGGGGG | GTTTCTTGTC | 5940 |
| AGTACGCGAA | GAACCACGCC | TGGCCGCGAG | CGCCAGCACC | GCCGCTCTGT | GCGGAGACCT | 6000 |
| GGGCACCAGC | CCCGCCGCCG | CCAGGAGCAT | TGCCGTTCCC | GCCA | | 6044 |